(12) United States Patent
Grant et al.

(10) Patent No.: US 12,167,965 B2
(45) Date of Patent: Dec. 17, 2024

(54) LIQUID COLLAGEN BIOINKS AND METHODS TO MAKE AND USE COLLAGEN STRUCTURES

(71) Applicant: The Curators of the University of Missouri, Columbia, MO (US)

(72) Inventors: Sheila Grant, Columbia, MO (US); Colten Snider, Columbia, MO (US); David Grant, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 253 days.

(21) Appl. No.: 17/643,046

(22) Filed: Dec. 7, 2021

(65) Prior Publication Data
US 2022/0175534 A1    Jun. 9, 2022

Related U.S. Application Data

(60) Provisional application No. 63/122,149, filed on Dec. 7, 2020.

(51) Int. Cl.
| | |
|---|---|
| *A61F 2/30* | (2006.01) |
| *B33Y 10/00* | (2015.01) |
| *B33Y 70/10* | (2020.01) |
| *B33Y 80/00* | (2015.01) |
| *B82Y 5/00* | (2011.01) |
| *B82Y 40/00* | (2011.01) |
| *C08L 89/00* | (2006.01) |

(52) U.S. Cl.
CPC ............ *A61F 2/30* (2013.01); *B33Y 70/10* (2020.01); *B33Y 80/00* (2014.12); *C08L 89/00* (2013.01); *A61F 2002/30062* (2013.01); *A61F 2310/00371* (2013.01); *B33Y 10/00* (2014.12); *B82Y 5/00* (2013.01); *B82Y 40/00* (2013.01)

(58) Field of Classification Search
CPC .............. A61F 2/30; A61F 2002/30062; A61F 2310/00371; C08L 89/00; B33Y 80/00; B33Y 70/10; B33Y 10/00; B82Y 5/00; B82Y 40/00
See application file for complete search history.

(56) References Cited

U.S. PATENT DOCUMENTS

| | | | |
|---|---|---|---|
| 4,090,887 A | 5/1978 | Marquisee et al. | |
| 8,658,214 B2 | 2/2014 | Rodriguez et al. | |
| 8,765,182 B2 | 7/2014 | Day et al. | |
| 2004/0211316 A1* | 10/2004 | Collins | .................. C10L 1/328 |
| | | | 95/153 |
| 2006/0013886 A1 | 1/2006 | Wu et al. | |

(Continued)

OTHER PUBLICATIONS 103 as being unpatentable over Jabbari et al. (US 20080206308 A1) in combination with Washing Microspheres, TechNote 203 of Bangs Laboratory, Mar. 15, 2017. (Year: 2017).*

(Continued)

*Primary Examiner* — Blessing M Fubara
(74) *Attorney, Agent, or Firm* — Stinson LLP

(57) ABSTRACT

The present disclosure provides collagen bioink compositions and chemically uncrosslinked and crosslinked collagen structures including collagen microparticles and scaffolds. Also provided are methods of their fabrication and use. Applications for using these collagen structures include treatments of damaged tissue, particularly those caused by osteoarthritis.

17 Claims, 42 Drawing Sheets

(56) References Cited

U.S. PATENT DOCUMENTS

| | | | | |
|---|---|---|---|---|
| 2007/0275871 A1* | 11/2007 | Sadeghi | ............... | A61P 19/02 |
| | | | | 530/397 |
| 2008/0206308 A1* | 8/2008 | Jabbari | ............... | A61L 27/56 |
| | | | | 514/23 |
| 2011/0200591 A1* | 8/2011 | Bisgaard-Frantzen | ............... | |
| | | | | A23C 9/206 |
| | | | | 530/387.3 |

OTHER PUBLICATIONS

Mathieu, M, et al., "Induction of mesenchymal stem cell differentiation and cartilage formation by cross-linker-free collagen microspheres", Eur Cell Mater. Sep. 2, 2014; 28:82-96; discussion 96-7. (16 pgs).

Yao, L, et al., "Collagen microsphere serving as a cell carrier supports oligodendrocyte progenitor cell growth and differentiation for neurite myelination in vitro", Stem Cell Res Ther. 2013;4(5):109. (8 pgs).

Berndt, M, et al., "Fabrication and characterization of microspheres encapsulating astrocytes for neural regeneration", ACS Biomater Sci Eng. 2017;3(7): 1313-1321. doi:10.1021/acsbiomaterials. 6b00229 (21 pgs).

Chan, OCM, et al., "Fabrication of nano-fibrous collagen microspheres for protein delivery and effects of photochemical crosslinking on release kinetics", J Control Release. Jul. 14, 2008;129(2):135-43. doi: 10.1016/j.conrel.2008.04.011 (10 pgs).

Asghar, S., et al., "A facile approach for crosslinker free nano self assembly of protein for anti-tumor drug delivery: Factors' optimization, characterization and in vitro evaluation", European Journal of Pharmaceutical Sciences, vol. 63., Oct. 15, 2014, pp. 53-62 (11 pgs).

Webster TJ, et al., "Specific proteins mediate enhanced osteoblast adhesion on nanophase ceramics", J Biomed Mater Res 2000;51:475-483, Jun. 28, 2000 (9 pgs).

Price RL, et al., "Osteoblast function on nanophase alumina materials: Influence of chemistry, phase, and topography", Journal of Biomedical Materials Research Part A 2003;67A:1284-1293, Dec. 15, 2003 (10 pgs).

Webster TJ, et al., "Increased osteoblast adhesion on nanophase metals: Ti, Ti6A14V, and CoCrMo", Biomaterials 2004;25:4731-4739, Aug. 2004 (9 pgs).

Park GE, et al., "Accelerated chondrocyte functions on NaOH-treated PLGA scaffolds", Biomaterials 2005;26:3075-3082, Jun. 2005 (8 pgs).

Thapa A, et al., "Polymers with nano-dimensional surface features enhance bladder smooth muscle cell adhesion", Journal of Biomedical Materials Research Part A 2003;67(4):1374-1383, Dec. 1, 2003 (10 pgs).

Christenson EM, et al., "Nanobiomaterial applications in orthopedics", Journal of Orthopaedic Research 2007;25:11-22 (12 pgs).

Hsu, S-H, et al., "Biocompatibility of poly(ether)urethane-gold nanocomposites", J. Biomedical Materials Research Part A, Dec. 15, 2006, 79(4), 759-770 (12 pgs).

\* cited by examiner

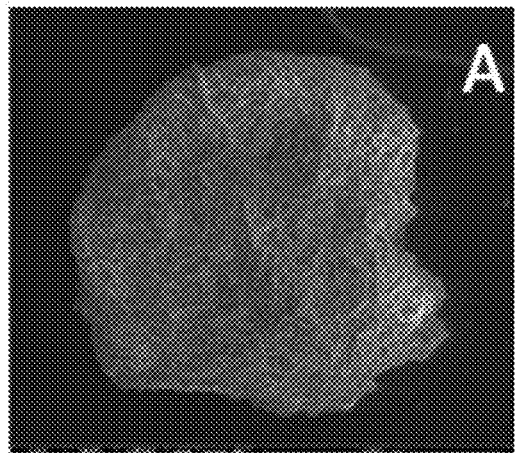
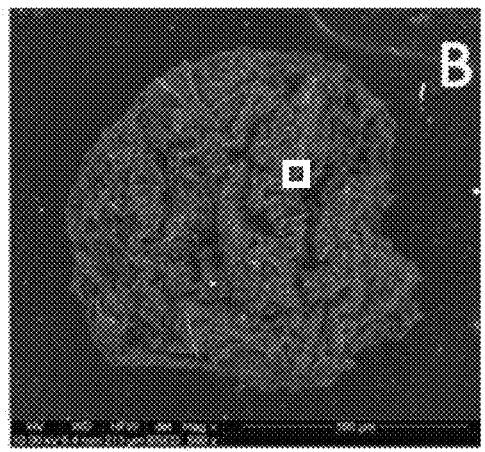
Figure 10A
Figure 10B
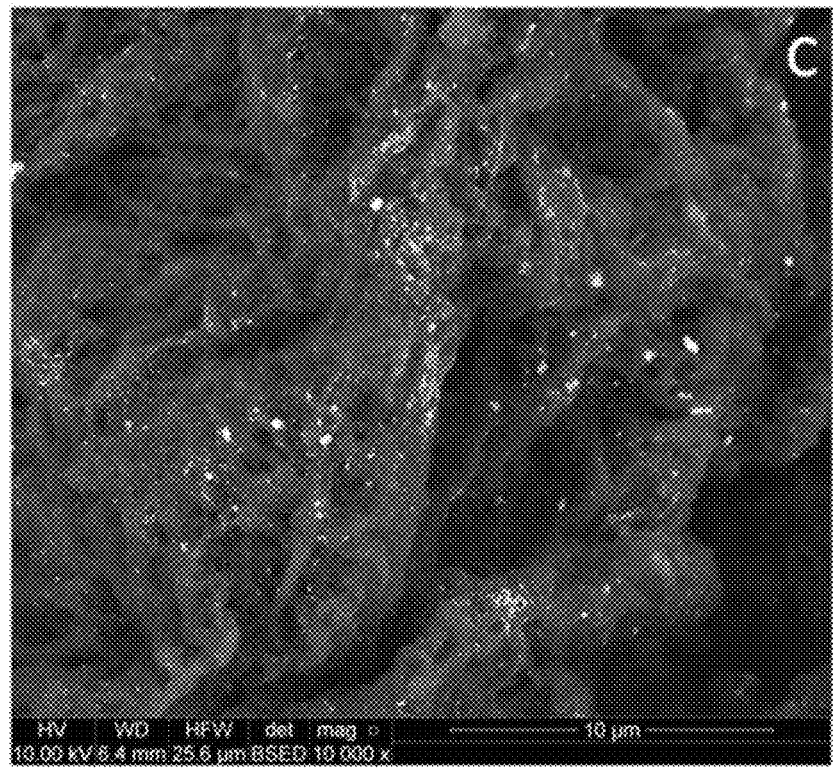
Figure 10C

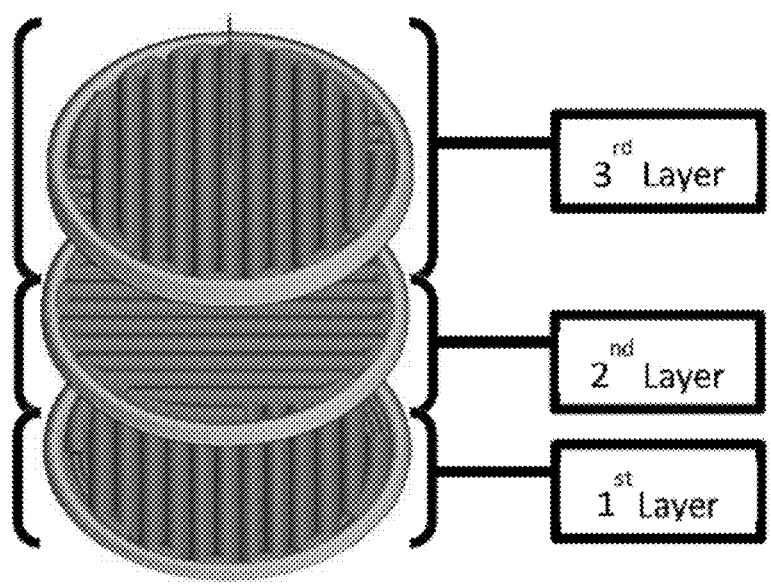
Figure 24
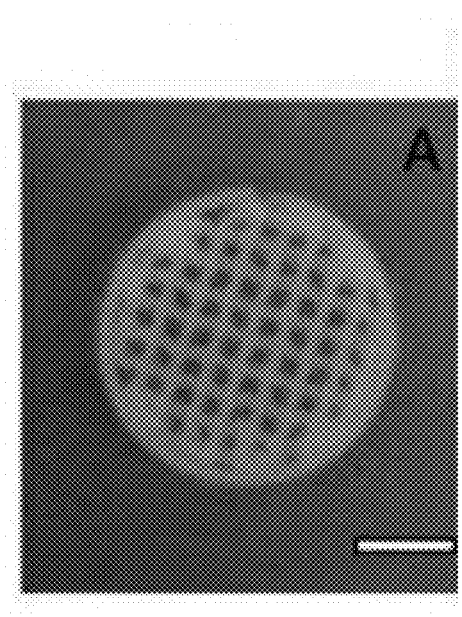 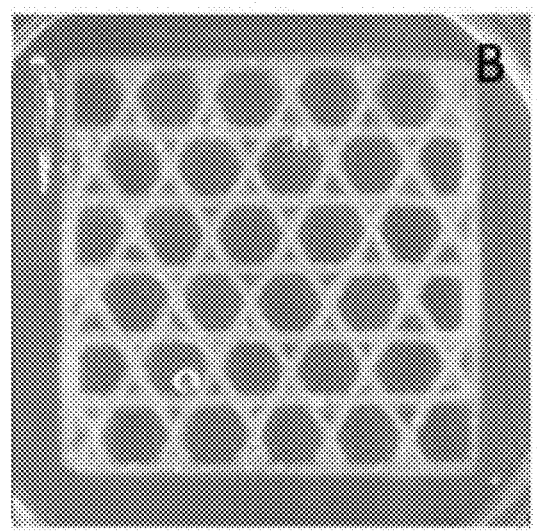
Figure 25A　　　　　　　　　　Figure 25B

LIQUID COLLAGEN BIOINKS AND METHODS TO MAKE AND USE COLLAGEN STRUCTURES

REFERENCE TO RELATED APPLICATIONS

This application claims the benefit of U.S. Provisional Patent Application No. 63/122,149, filed Dec. 7, 2020, the entire disclosure of which is incorporated herein by reference.

STATEMENT REGARDING FEDERALLY SPONSORED RESEARCH OR DEVELOPMENT

None.

FIELD OF INVENTION

The present disclosure relates to collagen bioink compositions and collagen structures, methods of fabrication, and applications thereof. More specifically, the present disclosure relates to chemically uncrosslinked and crosslinked collagen structures including collagen microparticles and scaffolds and their use in treating damaged tissue, particularly damaged tissue caused by osteoarthritis.

BACKGROUND OF INVENTION

Osteoarthritis (OA) is a joint degenerative disease affecting the entire joint structure wherein the disorder occurs in the articular cartilage, calcified cartilage, subchondral cortical and trabecular bone, joint capsular tissues, and synovium. Over time, bone-on-bone articulation arises, which can be debilitating to people who suffer from this disease hampering everyday activities. The articular cartilage is a specialized extracellular matrix mainly composed of type II collagen, helping to aid articulation and ease regular impacts imposed on the joint. Articulation is eased through a boundary layer of lubricin found at the interface of the synovial fluid and articular cartilage surface. Impacts imposed on the joint are eased through the meshwork of the ECM with a composition of a number of large and small proteoglycans along with aggrecan. OA progression over time can be difficult to determine with factors like age, sex, genetics, ethnicity, activity level, trauma, and alignment. Post-traumatic OA (PTOA) is a joint degenerative disease that arises from joint trauma leading to the same outcome of OA.

Symptomatic OA is defined as pain, aching, stiffness, and disability in a joint along with radiographic evident OA through the use of magnetic resonance imaging or other imaging devices. About 27 million people in the United States aged 25 or older have a clinical diagnosis of OA. PTOA is largely a lower extremity issue with most PTOA occurring in the ankle, knee, and hip. Approximately 12% of all symptomatic OA are PTOA cases. Direct costs of treating PTOA are estimated to exceed $3 billion annually, and 10% of all cases of knee OA arise from a PTOA event. People who injure their meniscus and/or their anterior cruciate ligament (ACL) commonly develop PTOA as well. It is estimated that 13% of isolated ACL injuries and up to 48% with ACL and meniscal injuries develop PTOA. In cases of ankle OA, studies have suggested up to 78% are PTOA related. PTOA of the hip accounts for 2% of all OA cases. Within the military population, the number of hip PTOA cases increases to 20%.

Collagen microparticles (CMs) are a specifically manufactured biomaterial derived from collagen and shaped into a spherical form. CMs are generally on the order of a few microns to a few hundred microns. A few different techniques have been developed to manufacture CMs. The most common techniques to manufacture CMs are by micropipetting and emulsion. In the micropipetting technique, collagen is pipetted onto a parafilm lined Petri dish and placed in a 37° C. environment until the collagen has gelated. This technique is not without its limitations. Creating a large cohort of CMs can be difficult as it requires multiple pipetting cycles to produce CMs, which can be time consuming and laborious. Also, CMs produced with this method are large with CM diameters ranging from 300 μm to 1,000 μm. This leaves no flexibility in size manipulation below 300 μm. If injectability is the intent of manufacturing CMs then the micropipetting technique is not a viable method. The other alternative to micropipetting is an emulsion. An emulsion is a method of manufacturing CMs by immersing collagen into an oil-based solution and adding a high shear rate. This shear force creates individual droplets of collagen within the oil solution. Gelation of collagen through heating or chemical crosslinking is usually used to crosslink the individual collagen droplets to form a CM. A drawback of manufacturing CMs by emulsion is its high shear rate. If CMs are intended to be loaded with cells for specific applications the micropipetting technique may be favored over emulsion due to the much more delicate nature of manufacturing through micropipetting.

In the originally reported the method of micropipetting CMs, the authors encapsulated human mesenchymal stem cells (MSCs) within CMs and were able to show maintenance of an hMSC phenotype while hMSCs were encapsulated. They also observed the development of vasculature two days after hMSC-CMs were subcutaneously implanted into NOD/SCID mice. Other works with micropipetted CMs include development for damaged articular cartilage and nucleus pulposus. One such study was able to develop zonal regions of articular cartilage through the stacking of osteogenic and chondrogenic CM subunits to reproduce a chondrogenic layer, calcified cartilage zone, and an underlying osteogenic layer over a 5-week period with rabbit MSCs.

As mentioned previously, CMs manufactured through emulsion can be on the order of tens of microns. This makes them more applicable for injection therapies. Some work with emulsion reports the use of chemical crosslinking to form stable CMs. Some of the reported chemical crosslinkers include 1-ethyl-3-[3-dimethylaminopropyl]carbodiimide (EDC)/N-hydroxysuccinimide (NHS), WSC, HMIDC, and glutaraldehyde. Other work has described the use of no chemical crosslinkers. Loading of CMs with bioactive agents to elicit a particular biologic response is an important factor in aiding the recovery of a lacking biologic system. The addition of TGF-B3 to CMs has been reported. MSCs were added to the TGF-B3 loaded CMs and adherence of the MSCs to the CMs was observed. MSCs chondrogenically differentiated and the MSC-CM clusters formed a tissue resembling cartilage with collagen II and aggrecan expression although cells became hypertrophic and calcification became an issue with the clusters. BMP-2 loaded CMs tuned for long-term release as a possible hard tissue regeneration tool has also been reported.

While the use of collagen-based ink for 3D printing is a relatively young discipline, there are possible advantages. Using a tissue-based material like collagen, the most prominent structural protein in the body, to print constructs allows the construction of more personalized materials that are specific to an individual patient's needs. Many factors of printing with tissue ink like diameter, stiffness, and porosity can be tuned to affected tissue sites to promote quicker integration times of native tissue. Cells can also be integrated within the collagen matrix to provide a personalized, living tissue. Materials printed with cells integrated within the printed matrix are termed bioinks. However, the printing of collagen-based tissues is not trivial. Methods of modifying either the collagen solution or the solution the collagen is printed into have been investigated to improve printing reproducibility, resolution, and fidelity.

Many different collagen-based bioinks have been prepared for printing. With collagen bioinks, there are a few different methods to either fibrilize or crosslink the printed tissue to form a rigid structure. With most collagen bioinks today, they are prepared in such a way that when introduced into a new solution that has an increased temperature or pH it triggers fibrilization of the collagen, which forms the structure. Preparation of these collagen bioinks can involve the neutralization of collagen with pH neutral solutions like cellular media or phosphate-buffered saline. Other works that crosslink collagen bioinks include chemical crosslinkers, such as genipin, thrombin used in collagen/fibrin inks, calcium chloride used in collagen/alginate inks, and ultraviolet light. Of the collagen bioinks, additives can be introduced to direct specific events when the scaffold is applied to the targeted site. One such study studied the use of a collagen type I and tricalcium phosphate ink loaded with human adipose-derived stem cells (hASCs). It was able to demonstrate differentiation of the hASCs through the osteogenic lineage in situ leading to potential applications in bone tissue regeneration.

Others have investigated the use of different solutions to print collagen bioinks into, these are called "printing baths." Printing into water alone can be challenging due to the inherent unpredictability of collagen through reproducibility, resolution, and fidelity. The use of thermoreversible support baths are of particular interest due to the difficulty in printing collagen directly into a fluid like water or cellular media. Initial work in 2015 developed freeform reversible embedding of suspended hydrogels (FRESH) thermoreversible support bath solution. The solution is composed of gelatin microparticles. By printing into a solution of gelatin microparticles this allows the bath to act as a rigid material at low shear stresses and act as a fluid at high shear stresses. At the extrusion site of the needle tip, the collagen bioink is injected into the bath and held stable whereas the needle tip easily moves through the bath solution to create the printed material. Senior et al also developed suspended layer additive manufacturing (SLAM). This technique is similar to the FRESH support bath solution but agarose microparticles compose the bath solution rather than gelatin. These solutions are not without their drawbacks. To remove the printed material from the FRESH solution the whole solution has to be heated to the liquid transition temperature of gelatin and then undergo washing to remove gelatin from the scaffold. While this is a relatively easy process as the transition temperature is around 37° C. at 37° C. this will not negatively impact a collagen-based material, remnant gelatin is a large concern with the FRESH process. The agarose transition temperature is much higher at around 90° C. so melting the agarose is not an option since at 90° C. collagen-based materials will denature at such temperatures. Therefore, washing the collagen materials is the only option to remove the agarose from the scaffold. Remnant agarose is much more of a concern with the SLAM technique relative to using the FRESH technique.

The core of developing a collagen bioink material is in its ability to be utilized in specific applications. Many different applications of collagen bioinks have been utilized today. Cartilage, skin, bone, cornea, heart valve, and neuron regeneration have all been investigated as possible avenues for collagen printed bioink scaffolds. Of course, each application will utilize cells specific to that region's native cell type like the integration of chondrocyte cells for cartilaginous printed scaffolds. One of the more unique applications of collagen bioink being 3D printed used FRESH printing of collagen bioink focused on the reproduction of a functional heart. It was able to achieve a functional scaled ventricle model with synchronized contractions along with a functional tri-leaflet heart valve and reproduction of an anatomically scaled heart using CT imaging.

Current techniques to mitigate progression of PTOA are lacking. Pain management and articular function are the focus of treatment today without addressing the progressive degradation of PTOA. The regeneration of native articular tissue is another aspect of PTOA not addressed today. Some treatments like microfractures and autologous chondrocyte implantation, and osteochondral grafting help to stimulate regeneration of tissue at damaged sites albeit with mixed results. With microfracturing, the regenerated tissue does cover the damage it also is not ideal as the tissue formed is not as stable and can degrade more quickly which becomes a problem in the future for patients. The ability to mitigate catabolic factors that progress PTOA over time is essential if establishment of new native articular tissues are to be successfully achieved. One goal of this work was to develop a targeted injectable based therapeutic to mitigate progression of PTOA and a delivery technique of autologous stem cells to regenerate native cartilage after mitigation of PTOA progression. CMs provide an easily injectable material that can be loaded with known PTOA mitigating, anti-inflammatory, or cells and can be conjugated with targeting antibodies that can bind to damaged cartilage regions.

SUMMARY OF INVENTION

The disclosure provides a collagen bioink composition, chemically uncrosslinked and crosslinked collagen structures including collagen microparticles and scaffolds, and methods of their fabrication and use.

In one aspect, the inventive composition collagen bioink composition comprising collagen, a polar solvent, and a stabilizing divalent ion chelating agent, wherein the collagen bioink fibrilizes when introduced into a printing solution substantially free of a crosslinker is described.

Another aspect of the disclosure is a chemically uncrosslinked collagen structure, wherein the structure comprises the collagen bioink composition after fibrilization in a printing solution substantially free of a crosslinker.

Another aspect of the disclosure is a chemically crosslinked collagen structure, wherein the structure comprises the collagen bioink composition after fibrilization in a printing solution and after crosslinking. The chemically crosslinked collagen structure can optionally be crosslinked to an antibody, a peptide, an aptamer, a functionalized nanoparticle, or a combination thereof.

Yet another aspect of the disclosure is a pharmaceutical composition comprising a plurality of collagen microparticles made from the collagen bioink composition.

In another aspect, the disclosure is directed to a method to fabricate a collagen bioink composition, the method comprising: precipitating collagen from a collagen solution; centrifuging the precipitated collagen solution until a collagen pellet is formed; isolating the collagen pellet from the supernatant of the precipitated collagen solution; dissolving the collagen pellet in a polar solvent to make a collagen solution; placing the collagen solution in a dialysis cassette; immersing the dialysis cassette in a dialysis solution comprising a divalent ion chelating agent and water with a pH of 7.5; and removing the collagen bioink composition from the dialysis cassette is described.

In yet another aspect, a method to fabricate chemically uncrosslinked collagen microparticles is described, wherein the method comprises: combining an oil and either sorbitan monooleate or sorbitan monostearate and stirring to create the printing solution; adding a collagen bioink composition dropwise to the printing solution to create a combined solution; stirring the combined solution; increasing the temperature of the combined solution to 37° C. while continuing stirring; and centrifuging the combined solution to collect the microparticles, wherein the combined solution is substantially free of crosslinker.

A further aspect of the invention is a method to 3D print a chemically uncrosslinked collagen structure, wherein the method comprises: filling a bioprinter print cartridge of a 3D printer with the collagen bioink composition; and positioning the collagen bioink composition through a 4° C. printhead into a printing solution in a programmed shape of the structure.

Another aspect of the invention is a method to fabricate a chemically uncrosslinked collagen structure, the method comprising: filling a syringe of an electrospinning system with a collagen bioink composition; and electrospinning the collagen bioink composition into a printing solution filled metal container to generate the collagen structure, wherein the collagen bioink composition and the printing solution are substantially free of crosslinker.

Yet another aspect of the invention is a method to fabricate a chemically crosslinked collagen structure, wherein the method comprises incubating a chemically uncrosslinked collagen microparticles or structure with a crosslinker and optionally an antibody, a peptide, an aptamer, a functionalized nanoparticle, or a combination thereof.

Further provided is a method of using a collagen structure for tissue engineering, wherein the structure is placed in proximity to cells or a tissue, wherein the cells or tissue attach to and grow on the structure.

Another aspect disclosed is a method of treating damaged tissue in a subject in need thereof comprising placing a collagen structure within the subject in proximity to the damaged tissue.

Yet another disclosed aspect is a method of treating osteoarthritis comprising administering an effective amount of a pharmaceutical composition comprising a plurality of collagen microparticles to a subject in need thereof by injection into the affected area.

BRIEF DESCRIPTION OF DRAWINGS

FIG. 10A is a scanning electron micrograph of a CM conjugated with AuNPs at 600×.

FIG. 10B is a backscatter electron micrograph of a CM conjugated with AuNPs at 600×.

FIG. 10C is a backscatter electron micrograph of a CM conjugated with AuNPs at 10,000×, which shows a magnified portion of FIG. 10B.

FIG. 24 depicts a Slic3r computer generated sliced diagram of a 6 mm×0.8 mm scaffold.

FIG. 25A depicts a 3D printed 6 mm×0.8 mm cylinder collagen scaffold printed in water using the Cellink BioX printer.

FIG. 25B depicts a 3D printed 20 mm×20 mm×1 mm rectangular collagen scaffold printed in an agarose microparticle solution using the Cellink BioX printer.

DETAILED DESCRIPTION OF INVENTION

Figure 1:
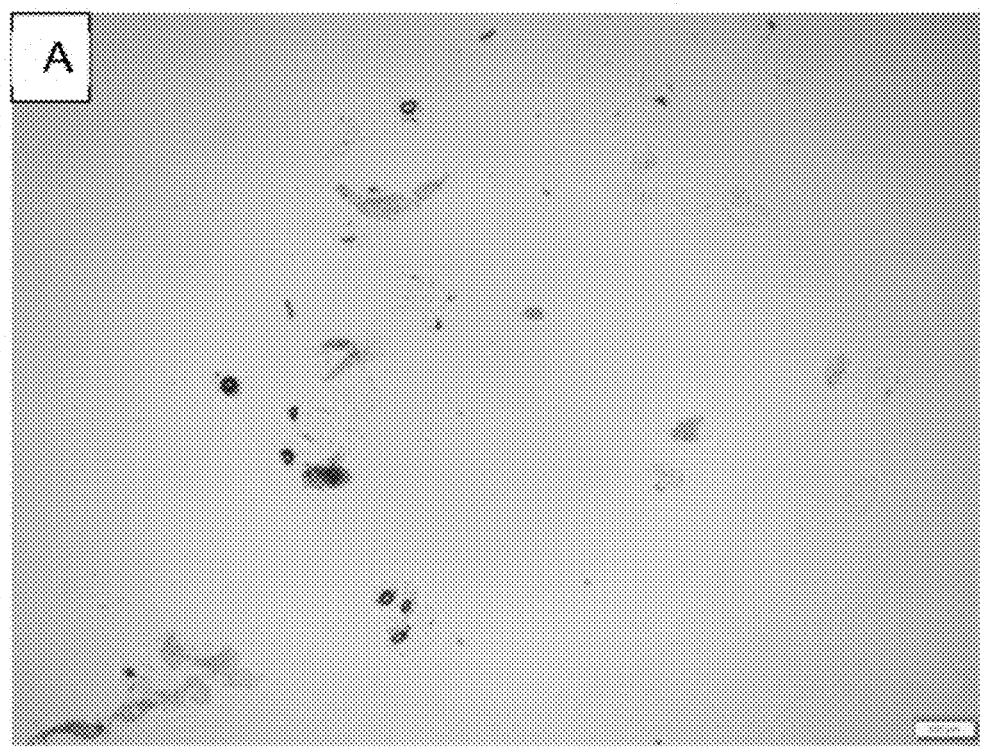
FIG. 1 depicts 4× microscopy images of sonicated CMPs using light microscopy.

Fabrication of a liquid collagen solution that fibrilizes when introduced into ionic solutions or introduced into physiologic temperatures was the genesis of this work. Exploiting the unique fibrilizing characteristics of the liquid collagen was of peak interest. Fabrication of this liquid collagen into CMs and the ability to 3D print with it as well were the most appreciable for the material and were further investigated in the following chapters.

An objective of this work was to develop, characterize, and optimize a technique to fabricate CMs that are suitable for intraarticular injection for treatment of PTOA. Initial work was performed to determine best techniques to fabricate uniform CMs with collagen fibril formation. To achieve uniform CMs multiple techniques of fabrication were investigated such as water in oil emulsion, water in water emulsion, and probe sonication. Water in oil emulsion was tapped due to its ease of reproducibility. Multiple oils and surfactants were studied to see how the liquid collagen interacted. Chemical crosslinking while in emulsion was also evaluated to conjugate nanoparticles such as gold. Gold nanoparticles are known free radical scavengers that reduce reactive oxygen species. Light microscopy was used to observe the CMs fabricated. Scanning electron microscopy (SEM), polarized light microscopy, and FTIR analysis was used to determine fibril formation of the of the collagen within the CMs. Fibril formation provides evidence of a stable collagen structure at physiologic temperatures and also emulates a native tissue network. Work then progressed into general in vitro testing to help determine biocompatibility of CMs. A WST-1 assay was utilized to determine biocompatibility of CMs and identify if length of emulsion also played a role in biocompatibility. Finally, more application-based testing of CMs as a PTOA treatment were investigated. Specific binding of CMs loaded with anti-inflammatory agents is of peak interest. Conjugation of collagen type II antibodies (CIIMAb) to CMs was investigated using fluorescent imaging. Ex vivo studies of CIIMAb-CMs exposed to damaged porcine cartilage were performed to verify specific binding of CIIMAb-CMs to damaged cartilage sites. Testing to determine CMs proclivity to mitigate PTOA progression through ROS mitigation was examined. In vitro work exposing chondrocyte cells to procatabolic factors observed in a PTOA environment were studied with anti-inflammatory loaded CMs.

Another objective of this work was to develop and characterize a technique to 3D print with the liquid collagen solution. Significant work on optimizing the parameters of printing the material were investigated along with solutions in which the liquid collagen could be printed into were also of interest. The goal of this work was to print reproducible collagen scaffolds. A BioX extrusion based 3D printer by Cellink was utilized in this work along with a custom built printer. As mentioned previously, initial work to determine optimal extrusion rate and printing speed were tested through visual inspection under a microscope to examine collagen diameters. Rates that provided uniform diameters were chosen due to making the most reproducible scaffold. Various printing solutions were also investigated. Printing into agarose microparticles provides better support and resolution of printed scaffolds but also include more washing to remove agarose off of the scaffold. Printing parameters also have to be adjusted depending on each solution printed into. In vitro work was also performed with the printed scaffolds. It became evident crosslinking of the scaffolds prior to in vitro work would be necessary to maintain the structural integrity of the scaffold. Genipin crosslinking was not only used to chemically crosslink the scaffolds but to also conjugate gold nanoparticles. Work was also performed to coat the collagen scaffolds with laminin to aid cellular attachment. Biocompatibility analysis was performed with the printed scaffolds.

Multiple biomaterials have been described in this disclosure. Decellularized porcine diaphragm extracellular matrix was homogenized and supplemented with various biomodulatory agents. It was developed as an injectable material with possible applications in mitigation of posttraumatic osteoarthritis (PTOA). Optimizing polycaprolactone and lecithin electrospun nanofibers for increased reproducibility was studied. A neutral pH liquid porcine collagen type I solution was developed for two separate projects including development of collagen microparticles (CMs) and 3D printed scaffolds. The CMs were fabricated by emulsifying the liquid collagen solution in a water-in-oil emulsion. Characterization of the CMs through electron microscopy, Fourier transform infrared spectroscopy analysis, differential scanning calorimetry, and biocompatibility analysis were conducted. The CMs were then investigated as a potential targeted PTOA mitigating agents by conjugating targeting antibodies on CMs to bind to damaged articular cartilage. CMs were also laden with mesenchymal stem cell and studied in culture over 2 weeks. The targeted CMs successfully bound to damaged cartilage and were able to mitigate reactive oxygen species production from interleukin-1beta stimulated human chondrocyte cells with addition of anti-inflammatory agent, curcumin. Finally, use of the developed liquid collagen as a potential bioink for 3D printing was investigated.

Posttraumatic osteoarthritis (PTOA) is a particular form of osteoarthritis where an acute injury leads to damage of the articular cartilage, subchondral bone, affects joint articulation, and can also create joint instability. PTOA is commonly found in young, healthy, and typically more active patients due to PTOA occurring from factors like a meniscal tear, ACL rupture, ankle instability, shoulder dislocation, and patellar dislocation. As of 2005, PTOA comes at a cost of $3 billion annually. The results presented herein demonstrate a unique method to fabricate a liquid collagen solution that can easily fibrilize under increased thermal conditions or when immersed in ionic solutions. The liquid collagen was found to be useful for the fabrication of Collagen Microparticles (CM). The CMs have the potential to be an injectable material for mitigating the progression of PTOA and may have applications in tissue regeneration. The liquid collagen also has valuable applications in additive manufacturing techniques for the development of collagen-based scaffolds.

This disclosure describes work towards the fabrication of biomaterials suitable for in vivo use. Characterization and optimization of injectable homogenized extracellular matrix constructs, electrospun PCL/lecithin scaffolds, CMs, and 3D printed collagen scaffolds were all reported in this work. The fabrication of homogenized extracellular matrix constructs and therapeutic/targeting CMs shows their individual potentials as injectable therapeutics for PTOA applications. Work on improving PCL/lecithin electrospun scaffolds reproducibility was achieved. Finally, early-stage development of collagen-based additive manufacturing 3D printing was conducted with evidence provided for scaffolds integration with fibroblast cells and human stromal cells for potential future work in organ development. More analysis needs to be conducted with respect to each project for direction into in vivo evaluations. Each project is at the forefront of biomaterials innovation development and could provide therapeutic treatments for patients in the future.

The present disclosure provides improved collagen microparticles that be delivered via injection to various tissue repair sites.

The advantage of injectable collagen microparticles over conventional ECM implant materials are that they i) can conform to the repair site (such as wound bed or defect) to allow complete coverage and contact with the repair site; and ii) can be injected through hypodermic syringes or cannulas to the site of the fracture (or ligament/tendon tear) without open surgery, reducing the risk of infection during operation. Particularly, an injectable collagen microparticle-antibody conjugation with optional gold nanoparticles has been developed for musculoskeletal tissue engineering applications.

The present disclosure further provides a general fabrication method for the abovementioned injectable collagen microparticles. When metallic nanoparticles, such as gold and silver, are employed, the fabrication method may further include the optional functionalizing step before the aforesaid conjugating step. The optional functionalizing step comprises functionalizing preselected nanoparticles with surface functional groups capable of bonding the collagen microparticles and/or tissue.

Collagen Bioink Compositions and Methods of Fabrication

One aspect of the disclosure is a collagen bioink composition. The collagen bioink composition can comprise collagen, a polar solvent, and a stabilizing divalent ion chelating agent, wherein the collagen bioink composition fibrilizes when introduced into a printing solution substantially free of a crosslinker.

The stabilizing divalent ion chelating agent can be ethylenediaminetetraacetic acid (EDTA) or ethylene glycol tetraacetic acid (EGTA).

Alternatively, the stabilizing divalent ion chelating agent can be replaced with a different chelating agent selected from the group consisting of L-glutamic acid, N,N-diacetic acid, tetrasodium salt, sodium phytate, and combinations thereof.

The pH of collagen bioink composition is preferably 7.5.

The collagen can be any type of collagen, but preferred collagen types are collagen type I, II, III, and IV. The liquid collagen of the collagen bioink composition is a quasi-state collagen.

The collagen bioink composition can further comprise nanoparticles. These nanoparticles can be any nanoparticles as described herein.

The collagen bioink composition can further comprise an anti-inflammatory agent. The anti-inflammatory agent can be selected from the group consisting of epigallocatechin-gallate (EGCG), curcumin, onion extract, pycnogenol, willow bark extract, *Boswellia serrata* resin, resveratrol, *Uncaria tomentosa* extract, capsaicin, and combinations thereof.

For fibrillization of the collagen bioink composition to occur, the printing solution can have a pH of 7.0 to 7.5 and a temperature of 30° C. to 40° C., preferably 37° C. The printing solution can comprise cell culture medium, water, phosphate buffered saline, or a combination thereof.

Another aspect of the disclosure is a method to fabricate a collagen bioink composition described herein, wherein the method comprises: precipitating collagen from a collagen solution; centrifuging the precipitated collagen solution until a collagen pellet is formed; isolating the collagen pellet from the supernatant of the precipitated collagen solution; dissolving the collagen pellet in a polar solvent to make a collagen solution; placing the collagen solution in a dialysis cassette; immersing the dialysis cassette in a dialysis solution comprising a divalent ion chelating agent and water with a pH of 7.5; and removing the collagen bioink composition from the dialysis cassette.

The polar solvent can be glacial acetic acid, ethanol, methanol, acetone, acetonitrile, or a combination thereof. The glacial acetic acid can be 0.5 M glacial acetic acid.

The collagen of the collagen solution is preferably at a concentration of from about 0.25 to about 50 mg/mL. The collagen can be precipitated with sodium chloride. The sodium chloride can be from about 0.5M to about 3M sodium chloride, preferably about 1.04 M sodium chloride. The molecular weight cut off of the collagent can vary from 5 kD to 30 kD.

The divalent ion chelating agent can comprise ethylenediaminetetraacetic acid (EDTA) or ethylene glycol tetraacetic acid (EGTA). The dialysis solution can comprise 5 mg/mL to 80 mg/mL of divalent ion chelating agent in water.

The pH of the dialysis solution is maintained at about 7.5 daily until the pH no longer fluctuates from 7.5.

The dialysis solution can further comprise nanoparticles, an anti-inflammatory agent, or a combination thereof. The nanoparticles can be any nanoparticle as described elsewhere herein.

Preferred anti-inflammatory agents include epigallocatechin-gallate (EGCG), curcumin, onion extract, pycnogenol, willow bark extract, *Boswellia serrata* resin, resveratrol, *Uncaria tomentosa* extract, and capsaicin.

Collagen Structures

The collagen bioink composition described herein can be used to fabricate collagen structures. Collagen structures are made by fibrilizing the collagen bioink composition in a printing solution. The collagen structures can comprise chemically uncrosslinked or crosslinked collagen structures. The collagen structures can contain collagen fibrils throughout the structure. The collagen structures can further comprise nanoparticles. The collagen structures can be nontoxic and/or biocompatible. The collagen structure can comprise a collagen scaffold or a plurality of collagen microparticles.

The collagen scaffold can be patterned to comprise a plurality of layers and/or to include a plurality of holes. The collagen scaffold can be a variety of shapes, including a cylinder or a rectangle.

The chemically uncrosslinked collagen structures are made in a composition substantially free of crosslinker. The collagen structure can alternatively comprise a plurality of collagen microparticles. The microparticles can have one dimension be from about 1 µm to about 500 µm. The microparticles preferably have one dimension of about 5 µm to 280 µm. The microparticles preferably have a standard deviation in diameter of from about 10 µm to about 50 µm.

A microparticle is a particle with each dimension ranging from 1 µm to 1000 µm. Preferably, the microparticle does not have sharp edges and is a regular shape such as a rod or sphere. A rod's aspect ratio is the ratio of its major axis to its minor axis, and the ratio can range from 1.1 to 40:1. The major axis of the rod can preferably range from 1-10 µm, and the minor axis of the rod can range from 0.25-1 µm in diameter. In a most preferred embodiment, the microparticle is a microsphere.

The collagen microparticles can be injectable. The injectable microparticles can have the denaturation temperature of the microparticles increase upon conjugation with a nanoparticle as compared to collagen microparticles not conjugated with a nanoparticle. The injectable collagen microparticles can have an extrusion force measured in a 22-gauge cannula be from about 0.5 N to about 10 N, from about 0.5 N to about 5 N, or from about 1 N to about 4 N. The injectable collagen microparticles can have a cell viability measured using a dsDNA assay be increased as compared to collagen microparticles not conjugated with a nanoparticle.

The chemically crosslinked collagen structures can be crosslinked by adding a crosslinker to the printing solution or by incubating a chemically uncrosslinked collagen structure with a crosslinker. The crosslinker can be EDC/NHS or genipin. The crosslinker is preferably genipin.

The chemically crosslinked collagen structure can further be crosslinked to an antibody, a peptide, an aptamer, a functionalized nanoparticle, or a combination thereof.

The functionalized nanoparticle can be any nanoparticle described elsewhere herein.

The antibody is preferably a collagen antibody. The peptide is preferably a RGD peptide. Preferably, the chemically crosslinked collagen structure binds damaged cartilage over undamaged cartilage when crosslinked to the antibody, peptide, or aptamer.

Nanoparticles

Prior studies have demonstrated that nanoparticles are more hydrophilic and possess an increased number of atoms and crystal grains at their surface compared to conventional materials. The large number of grains at the surface leads to increased surface roughness, surface area, and surface energy which are thought to contribute to an increase in protein adsorption and unfolding. For example, nanoscale ceramics, metals, and polymers have all been shown to improve cellular function compared to conventional materials. Webster T J et al. J Biomed Mater Res 2000; 51:475-483; Price R L, et al. Journal of Biomedical Materials Research Part A 2003; 67A:1284-1293; Webster T J, et al. Biomaterials 2004; 25:4731-4739; Park G E, et al. Biomaterials 2005; 26:3075-3082; Thapa A, et al. Journal of Biomedical Materials Research Part A 2003; 67A:1374-1383; Christenson E M, et al. Journal of Orthopaedic Research 2007; 25:11-22.) These properties make nanoparticles ideally suited to enhance the biocompatibility and cell/tissue interaction with collagen structures.

The nanoparticles described herein may be selected from a variety of nanoparticles, such as metallic nanoparticles, ceramic nanoparticles, polymer nanoparticles, and combinations thereof.

The metallic nanoparticles can comprise gold, zinc oxide, silver, titanium, copper, selenium, nickel, platinum, zinc peroxide, magnesium oxide, cerium oxide, titanium dioxide, or a combination thereof.

The ceramic nanoparticles can comprise an oxide, a carbide, a phosphate or a carbonate of a metal or metalloid such as calcium, titanium, silicon, or a combination thereof. The ceramic nanoparticles can comprise magnesium oxide, cerium oxide, graphene, carbon nanotubes, or combinations thereof.

The polymer nanoparticles can comprise a degradable polymer, an anionic copolymer, or a combination thereof. Examples of suitable degradable polymer nanoparticles include nanoparticles comprising polycaprolactone, polylactic acid, polyglycolic acid, polylactic glyocolic acid, or a combination thereof. Examples of suitable anionic copolymer nanoparticles include nanoparticles comprising methacrylic acid, polyethene glycol, poly(propylene glycol) (PPG), poly(lactic-co-glycolic acid) (PLGA)-(polyethylene glycol) PEG copolymer, or a combination thereof.

The nanoparticles described herein comprise nanoparticles that are nontoxic and biocompatible such as gold, silver, silicon carbide, silicon, silica, or a combination thereof.

Other examples of suitable nanoparticles include silicon nanoparticles, silica nanoparticles, alumina nanoparticles, calcium phosphate nanoparticles, $BaTiO_3$ nanoparticles, or combinations thereof.

Preferably, the nanoparticles are gold nanoparticles.

The nanoparticles can be shaped as spheres, cages, rods, stars, clusters, tubes, polygons, pyramids, rings, or combinations thereof. Preferably, the nanoparticles are spheres.

Generally, the median diameter of the nanoparticles can be from about 1 nm to about 150 nm, from about 1 nm to about 120 nm, from about 1 nm to about 110 nm, from about 1 nm to about 100 nm, from about 10 nm to about 150 nm, from about 10 nm to about 120 nm, from about 10 nm to about 110 nm, from about 10 nm to about 100 nm, from about 20 nm to about 150 nm, from about 20 nm to about 120 nm, from about 20 nm to about 110 nm, or from about 20 nm to about 100 nm. The nanoparticle preferably has a mean diameter of about 20 nm.

Further, the particle sizes for the nanoparticles can be polydisperse or monodisperse.

Depending on the chemical identity of the nanoparticles that are crosslinked to the tissue graft, the nanoparticle-conjugated collagen structures can scavenge free radicals. For example, gold nanoparticles have the ability to scavenge free radicals. Without being bound by theory, it is believed that the free radical scavenging ability of the gold nanoparticles is able to ameliorate and/or reduce inflammation at the collagen structure implant site. The free radical scavenging capability of the gold nanoparticle collagen scaffold can be measured using the technique of Hsu et al., J. Biomedical Materials Research Part A 2006, 759. The capacity of the sample to scavenge can be measured by placing the sample (7.5 mm diameter, 1 mm thick) in 3 mL of 32 µM 2,2-diphenyl-1-picrylhydrazyl (DPPH), vortexed, and left to stand at room temperature for 90 minutes. The absorbance of the reaction mixture can be measured at 515 nm using a UV/VIS spectrophotometer and the following equation:

Scavenging ratio (%)=[1−Absorbance of test sample/Absorbance of control]×100%.

Thus, the free radical scavenging ratio of the gold nanoparticle collagen scaffold is expected to be higher than the scavenging ratio of the collagen scaffold without gold nanoparticles.

Pharmaceutical Compositions

Another aspect of this disclosure is a pharmaceutical composition comprising a collagen as described herein, wherein the collagen structure comprises a plurality of collagen microparticles. The pharmaceutical composition can be injectable. The pharmaceutical composition can further comprise an active agent. The active agent can comprise an anti-inflammatory agent, which can comprise epigallocatechin-gallate (EGCG), curcumin, onion extract, pycnogenol, willow bark extract, *Boswellia serrata* resin, resveratrol, *Uncaria tomentosa* extract, capsaicin, and a combination thereof. The pharmaceutical composition can also further comprise a carrier or excipient.

The injectable collagen microparticles can be prepared using nanoparticles having a median diameter described herein, preferably, from about 20 nm to about 100 nm.

A concentration of nanoparticles in the conjugation reaction having a median diameter from about 20 nm to about 30 nm can be from about $5 \times 10^{11}$ particles per mL to about $8 \times 10^{12}$ particles per mL, from about $7 \times 10^{11}$ to about $3 \times 10^{12}$ particles per mL, or from about $1 \times 10^{12}$ particles per mL to about $8 \times 10^{12}$ particles per mL. Preferably, the concentration of nanoparticles in the conjugation reaction having a median diameter from about 20 nm to about 30 nm can be from about $7 \times 10^{11}$ particles per mL to about $6 \times 10^{12}$ particles per mL.

The nanoparticles having a median diameter from about 20 nm to about 30 nm can be gold nanoparticles.

The injectable collagen microparticles can be prepared using nanoparticles having a median diameter from about 90 nm to about 100 nm and a concentration of nanoparticles in the conjugation can be from about $5 \times 10^9$ particles per mL to about $5 \times 10^{10}$ particles per mL, from about $5 \times 10^9$ particles per mL to about $3 \times 10^{10}$ particles per mL, from about $5 \times 10^9$ particles per mL to about $2 \times 10^{10}$ particles per mL, or from about $5 \times 10^9$ particles per mL to about $1.4 \times 10^{10}$ particles per mL.

The nanoparticles having a median diameter from about 90 nm to about 1000 nm can be gold nanoparticles.

The pharmaceutical composition can also comprise a pharmaceutically acceptable carrier or excipient. The pharmaceutically acceptable carrier comprises water, saline, buffered saline, cell culture media, plasma, platelet rich plasma, or a combination thereof.

Collagen Structure Fabrication Methods

A collagen structure can comprise a collagen scaffold, a plurality of collagen microparticles, or a plurality of collagen microfibers. The collagen structures of the present disclosure can be fabricated via emulsion, needle injection, 3D printing, and electrospinning methods.

Method to Fabricate Chemically Uncrosslinked Collage Microparticles Via Emulsion The method to fabricate chemically uncrosslinked collagen microparticles comprises: combining an oil and a surfactant (e.g., sorbitan monooleate or sorbitan monostearate) and stirring to create the printing solution; adding the collagen bioink composition as disclosed herein dropwise to the printing solution to create a combined solution; stirring the combined solution; increasing the temperature of the combined solution to 37° C. while continuing stirring; and centrifuging the combined solution to collect the microparticles, wherein the combined solution is substantially free of crosslinker.

The oil can be olive oil. The sorbitan monooleate concentration can be from about 0.02 to about 0.35% by volume. The sorbitan monostearate concentration can be from about 0.01 to about 2.50% by volume.

The printing solution can further comprise nanoparticles, an anti-inflammatory agent, or a combination thereof. The nanoparticles can be any of the nanoparticles described elsewhere herein.

The anti-inflammatory agent comprises epigallocatechin-gallate (EGCG), curcumin, onion extract, pycnogenol, willow bark extract, *Boswellia serrata* resin, resveratrol, *Uncaria tomentosa* extract, capsaicin, and a combination thereof.

Stirring the combined solution can occur for 1 hour. Continuing stirring after increasing the temperature of the combined solution to 37° C. can last for up to 16 hours. The method can further comprise washing the collected microparticles.

The resulting microparticles are uniform in size. They can have a standard deviation in size of less than 50 μm. Preferably, the collected microparticles have a standard deviation in size of less than 15 μm.

Method to 3D Print a Chemically Uncrosslinked Collagen Structure

The method to 3D print a chemically uncrosslinked collagen structure comprises: filling a bioprinter print cartridge of a 3D printer with a collagen bioink composition as described elsewhere herein; and positioning the collagen bioink composition through a 4° C. printhead into a printing solution in a programmed shape of the structure.

The printing solution can comprise cell culture media, water, phosphate buffered saline (PBS), or a combination thereof. Alternatively, the printing solution can comprise an agarose printing solution. A printing solution comprising cell culture media can further comprise cells.

The printing solution can further comprise nanoparticles, an anti-inflammatory agent, or a combination thereof. The nanoparticles can be any of the nanoparticles described elsewhere herein.

The anti-inflammatory agent comprises epigallocatechin-gallate (EGCG), curcumin, onion extract, pycnogenol, willow bark extract, *Boswellia serrata* resin, resveratrol, *Uncaria tomentosa* extract, capsaicin, or a combination thereof.

The positioning of the collagen bioink composition can comprise extrusion from a syringe pump comprising a 15- to 32-gauge conical nozzle. Preferably, the positioning of the collagen bioink composition comprises extrusion from a syringe pump comprising a 27-gauge conical nozzle.

The shape of the structure can be a plurality of microparticles, a plurality of microfibers, or a scaffold.

The extrusion pressure of the syringe pump can range from 6 kPa to 13 kPa.

The print diameter can be 50 μm to 800 μm. The print diameter is preferably 400 μm to 800 μm.

The print rate can be 0.1 mm/s to 10 mm/s. The printing rate is preferably 3 mm/s, and the print height is preferably 0.2 mm.

The 3D printing apparatus can comprise a CNC milling machine comprising X, Y, and Z stages each controlled by a stepper motor, wherein the X and Y stages are placed on top of each other to form a print bed, wherein the Z stage is placed perpendicular to the print bed, wherein a syringe pump is mounted on the Z stage, wherein the syringe pump holds and extrudes a collagen bioink composition as described elsewhere herein into a container of printing solution located on the print bed.

Method to Fabricate a Chemically Uncrosslinked Collagen Structure Via Electrospinning Electrospinning is a method to produce fibers from a liquid solution using a high voltage electric field.

This method to fabricate a chemically uncrosslinked collagen structure via electrospinning comprises: filling a syringe of an electrospinning system with a collagen bioink composition as described elsewhere herein; and electrospinning the collagen bioink composition into a printing solution filled metal container to generate the collagen structure, wherein the collagent bioink composition and the printing solution is substantially free of crosslinker.

Alternatively, the electrospinning can occur onto a metal ground plate instead of into a printing solution filled metal container. The metal ground plate can be a copper or aluminum plate.

The collagen structure preferably comprises a plurality of nanofibers.

The syringe can comprise a 15- to 32-gauge cannula tip. Preferably, the syringe comprises a 27-gauge cannula tip. The working distance between the cannulate tip and the metal container can range from 5 to 20 cm. The voltage of the electrospinning can vary from 15 kV to 18 kV. The printing solution can comprise cell culture media, water, phosphate buffered saline, or a combination thereof.

The printing solution can also comprise nanoparticles, an anti-inflammatory agent, or a combination thereof. The nanoparticles can be any of the nanoparticles described elsewhere herein.

The anti-inflammatory agent comprises epigallocatechingallate (EGCG), curcumin, onion extract, pycnogenol, willow bark extract, *Boswellia serrata* resin, resveratrol, *Uncaria tomentosa* extract, capsaicin, or a combination thereof.

Method to Fabricate a Chemically Crosslinked Collagen Structure

Method of Crosslinking

This method to fabricate a chemically crosslinked collagen structure comprises fabricating a chemically uncrosslinked collagen structure as described herein and further comprises incubating the chemically uncrosslinked collagen structure with a crosslinker. To conjugate an antibody, a peptide, an aptamer, a functionalized nanoparticle, or a combination thereof to the chemically crosslinked collage structure, the method can further comprise adding an antibody, a peptide, an aptamer, a functionalized nanoparticle, or a combination thereof to the incubation step of the method.

The crosslinker can be EDC/NHS or genipin. The crosslinker can have a concentration of 2 mM to 10 mM or, preferably, a concentration of 2 mM, 5 mM, or 10 mM.

Genipin is a naturally derived crosslinking agent isolated from the fruits of *Gardenia jasminoides* that can be used for fast, consistent crosslinking without cytotoxic byproducts. It spontaneously reacts with amino-group-containing compounds such as proteins, collagens, and gelatins to form monomer to tetramer crosslinks, and has an exceptionally low cytotoxicity. Genipin can also act as an anti-inflammatory agent and can reduce the immunogenicity of the scaffold. Genipin is also known as methyl (1S,2R,6S)-2-hydroxy-9-(hydroxymethyl)-3-oxabicyclo[4.3.0]nona-4,8-diene-5-carboxylate and has the following chemical structure:

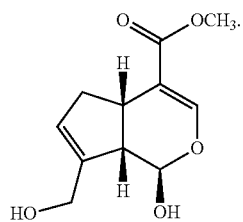 [SMILES: COC(=O)C1=CO[C@@H](O)[C@@H]2C(CO)=CC[C@H]12]

Genipin can be used in crosslinking applications such as those described herein. Because genipin crosslinking does not produce cytotoxic byproducts, solutions and methods utilizing it can be nontoxic and/or biocompatible.

Conjugation of a separate material (i.e. antibody, peptide, aptamer, functionalized nanoparticle, etc.) to the collagen microparticles is joining the two components by a covalent bond. Conjugating reagents are molecules that contain two or more reactive ends capable of chemically attaching to specific functional groups on proteins or other molecules (e.g., collagen microparticles). These functional groups can be amines, carboxyls, or sulfhydryls on the separate material. To react with amines on the separate material, the conjugating agent is selected from N-hydroxysuccinimide ester (NHIS ester), N-gamma-maleimidobutyryloxy succinimde (GMBS), imidoester (e.g., dimethyl adipimidate, dimethyl pimelimidate, dimethylsuberimidate, dimethyl 3,3'-dithiobispropionimidate2 HCl (DTBP)), pentafluorophenol ester (PFP ester), hydroxymethyl phosphine. A carboxyl group on the separate material can react with an amine on the nanoparticle directly by activation with carbodiimide. Various carbodiimides can be used including 1-ethyl-3-(3-dimethylaminopropyl)carbodiimide, dicyclohexyl carbodiimide, diisopropylcarbodiimide, and the like. A sulfhydryl group on the tissue can react with a malemide (e.g., N-e-Maleimidocaproic acid (EMCA)), haloacetyl (e.g., SBAP (NHS ester/bromoacetyl), SIA (NHS ester/iodoacetyl), SIAB (NHS ester/iodoacetyl), Sulfo-SIAB (sulfo-NHS ester/iodoacetyl), pyridyldisulfide (1,4-di(3'-(2'-pyridyldithio)-propionamido)butane (DPDPB), sulfosuccinimidy 6-(3'-[2-pyridyldithio]-propionamido)hexanoate (Sulfo-LC-SPDP), N-[4-(p-azidosalicylamido)butyl]-3'-(2'-pyridyldithio)propionamide (APDP)), or vinyl sulfone.

In the conjugation step, depending on the surface functional groups introduced, the separate materials are incubated (or mixed) with the collagen microparticles in a solution via a procedure available or known to the researchers in the field. The conjugating agent can be N-gamma-maleimidobutyryloxy succinimde (GMBS), N-e-Maleimidocaproic acid (EMCA), and Dimethyl 3,3'-dithiobispropionimidate.2 HCl (DTBP). For example, according to one embodiment, the crosslinking solution may contain acetone, 1×PBS (phosphate buffered saline), EDC (1-ethyl-3-[3-dimethylaminopropyl]carbodiimide) and NHS (N-Hydroxysuccinimide).

Various concentrations of separate materials may be utilized to achieve optimal crosslinking. For example, collagen microparticles and nanoparticles are first functionalized (e.g. with EDC/NHS and cysteamine). The incubation of collagen microparticles and nanoparticles generally lasts about 24 hours at room temperature on an orbital shaker table at low rpm. Following incubation, the resulting crosslinked collagen microparticles are vigorously rinsed with 1×PBS with several changes of the PBS solution to remove residual crosslinkers and unbound nanoparticles.

Functionalization of Collagen Structures, Nanoparticles, and Other Materials for Crosslinking Collagen structures and separate materials (i.e. an antibody, a peptide, an aptamer, a functionalized nanoparticle, or a combination thereof) must be functionalized if they do not already have the functional groups on their surface required for crosslinking via the selected crosslinking agent.

In the functionalizing step, the selected materials obtained commercially or synthesized according to various procedures in the field can be exposed to a plasma environment with selected plasma chemistry in order to introduce functionalities which will enhance the bonding between the materials and collagen microspheres. Generally, the precursor selected for plasma polymerization is a molecule that has one or more of the desired functional groups and one or more carbon-carbon double bonds. For example, if the desired surface functional group is an amine, the precursor would contain an amine and a carbon-carbon double bond. Examples of amines that can be used in plasma polymerization are allylamine, poly(allylamine), diaminocyclohexane, 1,3-diaminopropane, heptylamine, ethylenediamine, butylamine, propargylamine, propylamine, and the like. Amines that can be used in plasma polymerization are poly(allylamine), diaminocyclohexane, 1,3-diaminopropane, heptylamine, ethylenediamine, butylamine, propargylamine, propylamine, and the like.

When the desired surface functional group is a carboxylic acid, the precursor would contain a carboxylic acid group and a carbon-carbon double bond. Examples of compounds used are acrylic acid, methacrylic acid, propanoic acid, and the like. When the desired surface functional group is a hydroxyl group, the precursor would contain a hydroxyl group and a carbon-carbon double bond. Examples are allyl alcohol, hydroxyethyl methacrylate, hydroxymethyl acrylate, hydroxybutyl methacrylate, and the like.

The functional groups, such as NHx (x=1 or 2), OH, COOH, can be selected to act as anchoring points for crosslinking via covalent bond formation. A variety of plasma chemistry may be employed to introduce the functional groups. For example, allylamine may be used to deposit —NH, and, —NH2 containing plasma coatings on the material surfaces. Allyl alcohol, hydroxyethyl methacrylate (HEMA), acrylic acid, methacrylic acid, hydroxymethyl acrylate, hydroxybutyl methacrylate, or a combination thereof may be utilized as the monomers to deposit plasma coatings and introduce —OH, —COOH functional groups on material surfaces. Additionaly, organosilicons including trimethylsilane (3MS) and hexa-methyldisiloxane (HMDSO) may be used to plasma coat the materials to ensure excellent adhesion of plasma coating to nanowires. The organosilicon coating provides a layer on the material that aids adhesion of the material to the deposited functionalized coating. Subsequent plasma treatment using $O_2$ or $CO_2$ may be used to further increase the surface concentration of these functional groups.

Furthermore, materials may be functionalized via a chemical reaction utilizing an activating agent (e.g., an agent capable of activating a carboxylic acid); for example, dicyclohexyl carbodiimide, diisopropylcarbodiimide, or ethyl dimethylaminopropylcarbodiimide. The activating agent can be used alone or in combination with an agent that improves efficiency of the reaction by stabilizing the reaction product. Once such stabilization agent is NHS (N-hydroxysuccinimide). In various embodiments, EDC (1-ethyl-3-[3-dimethylaminopropyl]carbodiimide) and NHS (N-Hydroxysuccinimide) are used as the crosslinking agents wherein EDC reacts with the carboxylic acid groups found on materials such as degradable polymers and forms an O-acrylisourea derivative and NHS stabilizes this derivative and forms a succinimidyl ester bond, which allows binding to an amino group of the tissue by forming a covalent peptide bond with the material. When EDC and NHS are used to functionalize the materials, the molar ratio of the agents range from about 1:5 EDC:NHS to about 5:1 EDC:NHS; or about 2:5 EDC:NHS. Alternatively, materials may be functionalized via aminolysis by ethylenediamine or N-Aminoethyl-1,3-propanediamine.

For the materials of gold or silver nanoparticles, the nanoparticles can be functionalized by coordinating a ligand containing the desired functional group to the gold or silver atom. Generally, the ligand should have at least two functional groups; one of the functional groups can coordinate to the metal site and the other could be used to crosslink with the collagen structure. For example, a ligand having a thiol group and an amine group; e.g., cysteine, methionine, mercaptoalkylamines such as mercaptomethylamine, mercaptoethylamine (MEA), mercaptopropylamine, mercaptobutylamine, and the like, can be coordinated to the metal of the nanoparticle to provide a functional group for further reaction with the collagen structure. Also, a ligand having a thiol group and a carboxylic acid group; e.g., thiosalicylic acid, 2-mercaptobenzoic acid, can be coordinated to the metal of the nanoparticle to provide a functional group for further reaction with the collagen microparticle.

When the nanoparticle is silicon carbide, the silicon carbide nanoparticle can be treated with various reagents that have at least two functional groups; one group that can react with the surface hydroxy groups on the silicon carbide and another functional group that can crosslink to the collagen structure. For example, the silicon carbide particles can be reacted with aminoalkyl-trialkoxysilanes such as aminomethyl-trimethoxysilane, aminoethyl-trimethoxysilane, aminopropyl-trimethoxysilane, aminobutyl-trimethoxysilane, aminomethyl-triethoxysilane, aminoethyl-triethoxysilane, aminopropyl-triethoxysilane, aminobutyl-triethoxysilane, aminomethyl-tripropoxysilane, aminoethyl-tripropoxysilane, aminopropyl-tripropoxysilane, aminobutyl-tripropoxysilane, aminomethyl-tributoxysilane, aminoethyl-tributoxysilane, aminopropyl-tributoxysilane, aminobutyl-tributoxysilane, or a combination thereof to provide amine groups on the surface of the silicon carbide nanoparticle.

Methods of Use

The disclosure further provides a variety of applications of these chemically uncrosslinked and crosslinked collagen structures.

The collagen structures can be used for tissue engineering, wherein the structure is placed in proximity to cells or a tissue, wherein the cells or tissue attach to and grow on the structure. This can occur in a laboratory or clinical setting.

A method of treating damaged tissue in a subject in need thereof comprises placing a collagen structure as described elsewhere herein within the subject in proximity to the damaged tissue. The method can further comprise seeding the collagen structure with cells or tissue before placement within the subject. The damaged tissue can be a connective tissue. The damaged tissue can be selected from the group consisting of a meniscus, a tendon, a ligament, a diaphragm, and combinations thereof. The subject can be a human, pig, cow, sheep, or horse. The collagen structure can comprise a plurality of collagen microparticles and can be placed via injection. The collagen structure can comprise a formulated pharmaceutical composition comprising collagen microparticles.

Further disclosed is a method of treating osteoarthritis comprising administering an effective amount of a pharmaceutical composition described elsewhere herein comprising a plurality of microparticles to a subject in need thereof by injection into the affected area. The subject can be a human. The affected area can be within a joint. The joint can be selected from the group consisting of a knee, an ankle, a hip, a wrist, an elbow, a knuckle, a shoulder, and combinations thereof. The injection can be intraarticular.

The osteoarthritis can be post-traumatic osteoarthritis. Joint injury or trauma can result in acute post-traumatic osteoarthritis (PTOA).

PTOA is characterized by joint swelling, synovial effusion, inflammatory cell infiltration, and chronic pain. Articular cartilage degeneration is a result of PTOA which can lead to osteoarthritis (OA) in the majority of patients with joint injury. The treatment of PTOA is challenging and there are not approved therapies to cure acute post-traumatic arthritis, only therapies that address the symptoms of PTOA are available. Injection of the collagen microparticles described herein can reduce inflammation and treat the underlying mechanisms resulting in the osteoarthritis.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The term "substantially free of a crosslinker" includes materials where no crosslinker is present and where a negligible amount of crosslinker (e.g., 0.1 mM, 0.05 mM, 0.02 mM, 0.01 mM or less) is present.

This description is merely exemplary in nature and is in no way intended to limit the present teachings, application, or uses. Throughout this specification, like reference numerals are used to refer to like elements.

EXAMPLES

The following non-limiting examples are provided to further illustrate the present invention and further provides several examples of the collagen bioink compositions and chemically uncrosslinked and crosslinked collagen structures and methods of their fabrication and use.

Example 1: Preliminary Investigation on Fabrication of Collagen Microparticles

Introduction

Fabrication of microparticles as scaffolds for tissue engineering applications are one of many different scaffold fabrication techniques ranging from electrospinning to 3D printing. Microparticles are widely fabricated due to their ease of drug delivery and potential targeting of specific locations in the body. They serve as excellent drug delivery candidates because of their high surface area to volume ratio. Five different classifications for microparticle applications have been reported. The five classifications include 1) controlled release of bioactive agents; 2) delivery of bioactive agents in response to environmental stimuli; 3) act as miniature bioreactors embedded in surrounding tissue for regeneration; 4) serve as cell transporters; 5) manipulation of porosity for accelerated resorption; and 5) provide mechanical support for a weak matrix.

A few different techniques have been employed to fabricate microparticles. A couple common techniques for fabrication include water-in-oil (W/O) emulsion, and precision particle fabrication (PPF). W/O emulsion is a technique wherein a liquid "water" phase material of interest is introduced to an oil phase solution, typically on a stir plate, and emulsified at a high rpm or under sonication to generate liquid phase microparticles. The speed of rotation, frequency of sonication, and addition of surfactants to manipulate the interfacial tension in the emulsion can tune microparticle sizes. Generally, chemical crosslinking is employed to maintain the microparticles morphology under fabrication but temperature and pH adjustment can also be used to form stable microparticles. PPF is another technique used to fabricate microparticles. PPF is a technique wherein a bulk fluid is flowed through an inner sonicating nozzle which disperses the bulk fluid into uniform particles while being entrapped by an outer nozzle of flowing liquid which flows into a collection plate. Typically, in this setup adjusting the sonication frequency, flow rate of each fluid, and the distance between the end of the nozzle and the collection plate can affect the microparticle size distribution.

A wide range of material have been used for microparticle fabrication including natural materials like chitosan, collagen, and alginate or degradable, synthetic polymers like polylactic acid, polylactic glycolic acid, and polycaprolactone. Collagen is the most common protein found in the body with collagen type I being the most prevalent collagen. It serves as an excellent candidate as a biomodulatory and cellular transporter and has been utilized to transport cells to affected regions in the body. For example, it has been utilized in bone tissue engineering applications. Collagen is also advantageous due to its biodegradability, minimal immune response, and its exceptional biocompatibility. In this Example, various methods were investigated to fabricate collagen microparticles (CMPs).

Materials and Methods

Collagen Preparation

Porcine collagen type I (10 mg/ml, Sunmax Biotechnology, Taiwan) was precipitated using 1.04 M sodium chloride (NaCl, 99.0%, Sigma Aldrich, MO). The precipitated collagen solution was then centrifuged at 3,500 rpm for 15 minutes. A white collagen pellet was formed at the bottom of the tube and the supernatant was poured off leaving a 150 mg collagen pellet. Fifteen ml of 0.5 M glacial acetic acid (99.7%, Fisher Chemical, KS) was added to the collagen pellet and allowed to sit overnight at room temperature to let the collagen pellet dissolve. The collagen/acetic acid solution was then placed in a 15 ml, 10 kDa molecular weight cutoff dialysis cassette (Thermo Scientific, IL) and immersed in an ethylenediaminetetraacetic acid (35 mM, EDTA, Fisher Chemical, KS)/$H_2O$ solution with a pH of 7.5 using sodium hydroxide (10 N, NaOH, Ricca Chemical Co., TX). The pH of the EDTA solution was checked and maintained at 7.5 daily until the pH no longer fluctuated from 7.5. The collagen solution was then removed and pH was tested to ensure it was set at 7.5.

Collagen Microparticle Sonicator Fabrication

A Branson Sonifier 450, 102C probe sonicator was used to create CMPs. To prepare the CMPs, the sonicator was set to continuous at level 5. To collect the CMPs, a petri dish was filled with 40 ml of 37° C. dd$H_2O$. The distance between the tip of the probe to the petri dish was 14.5 cm. To create the CMPs a syringe was filled with liquid collagen and a 27 gauge needle was used to eject the liquid collagen onto the tip of the probe. Samples were then centrifuged at 4,000 rpm and stored at 4° C. in 70% ethanol.

Water-In-Water Fabrication

To create CMPs through water-in-water emulsion a 50 ml Erlenmeyer flask was used with a 6 cm stir bar. The Erlenmeyer flask was filled with 30 mm ddH$_2$O or cellularly relevant culture media and stirred at a rate of 1,250 rpm. Liquid collagen was then ejected into the Erlenmeyer flask using a syringe with a 27 gauge cannula. Five minutes after the addition of the liquid collagen, the stir plate heating element was set to 37° C. The emulsion was then stirred for 30 minutes. Samples were then washed at 4,000 rpm and stored at 4° C. in 70% ethanol.

Imaging Analysis

To visualize the preparation techniques of sonication and water-in water emulsion an IX50 (Olympus, PA) microscope with a 4× objective was utilized. A linear polarized light filter was also used to observe the birefringence of the CMPs. Images were captured using Olympus CellSens software.

Cell Biocompatibility

Cell biocompatibility testing was performed to observe the cellular viability of L-929 fibroblast cells (ATCC, VA) with CMPs. L-929 murine fibroblast cells were cultured at 37° C. and 5% CO$_2$ in Eagle's Minimum Essential Medium (ATCC, VA) supplemented with horse serum (10%, ATCC, VA) and penicillin-streptomycin (200 U/mL, ATCC, VA). Cells were subcultured and given fresh cell media as needed. All assays were performed in a biological safety cabinet under sterile conditions.

Cell proliferation reagent WST-1 (Sigma Aldrich, MO) was utilized to assess the biocompatibility of the CMPs. All CMPs were incubated with cell media for 24 hours and then added to a 96-well plate. 24 hours later, 0.75×10$^4$ L-929 murine fibroblasts/well were added to a 96 well plate. Half of the medium in each well was replaced after 3 days. At 4 days, WST-1 reagent was added to each well and the plates were incubated at 37° C. for 4 hours. After 4 hours, the media was removed from each well and absorbance readings were taken at 450 nm, with 600 nm filter, using a spectrofluorometer plate reader (Cytation 5, BioTek, VT). Relative viability was based on cells with no scaffold added.

Results

Sonicator CMPs Fabrication

Figure 2:
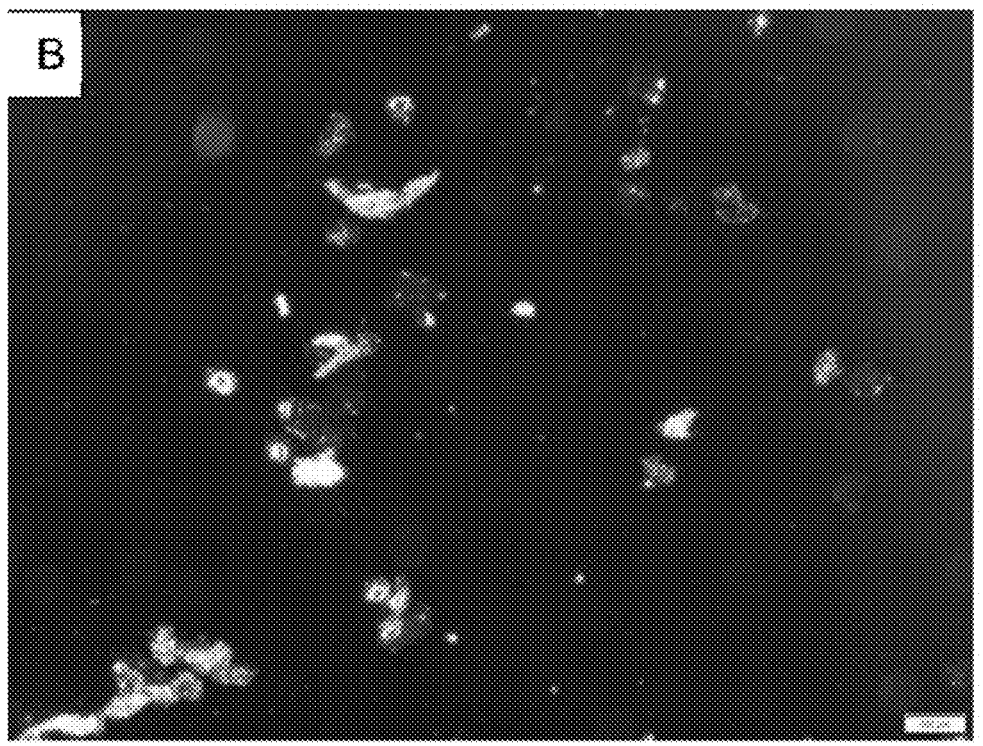
FIG. 2 depicts 4× microscopy images of sonicated CMPs using linear polarized light microscopy.

FIGS. 1-2 show the CMPs fabricated utilizing sonication. FIG. 1 is a light microscope image of the CMPs. A nonuniform distribution of CMPs were generated using this method. From visual inspection, immediately after the liquid collagen dispersed from the sonicating probe the CMPs formed and fibrilized. FIG. 2 is a linear polarized light microscope image of the same particles in FIG. 1. FIG. 2 provides a clearer picture of the CMPs. With this information, a strong birefringence can be observed which correlates to a fibrilized collagenous structure of the CMPs.

Water-In-Water Emulsion CMPs Fabrication

Figure 3:
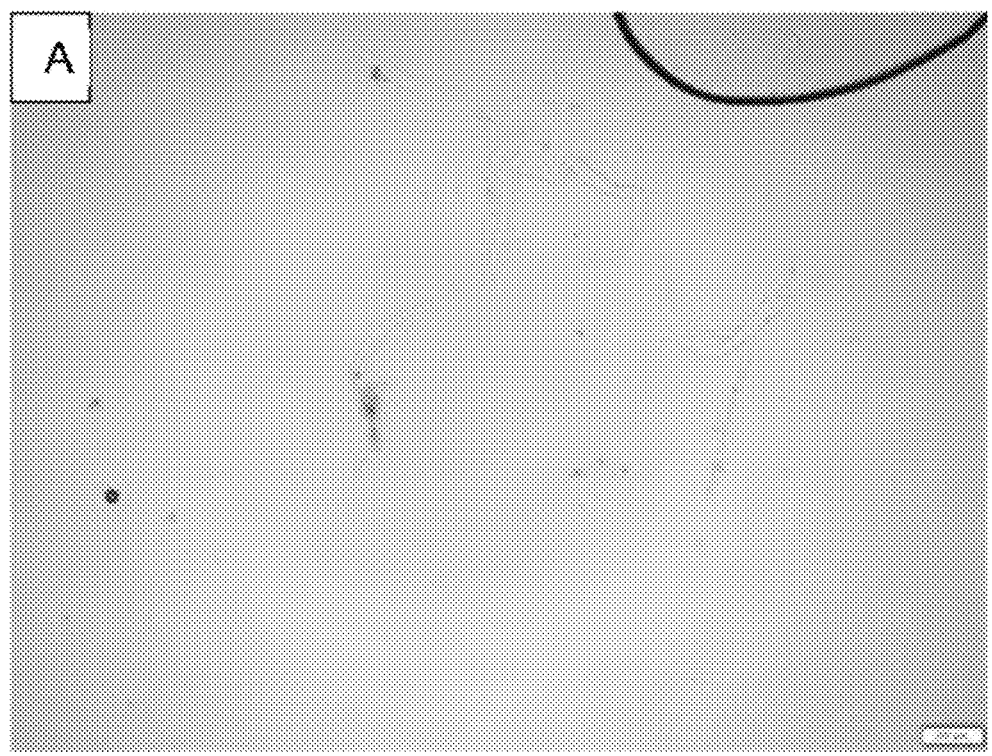
FIG. 3 depicts 4× microscopy images of water-in-water CMPs using light microscopy.
Figure 4:
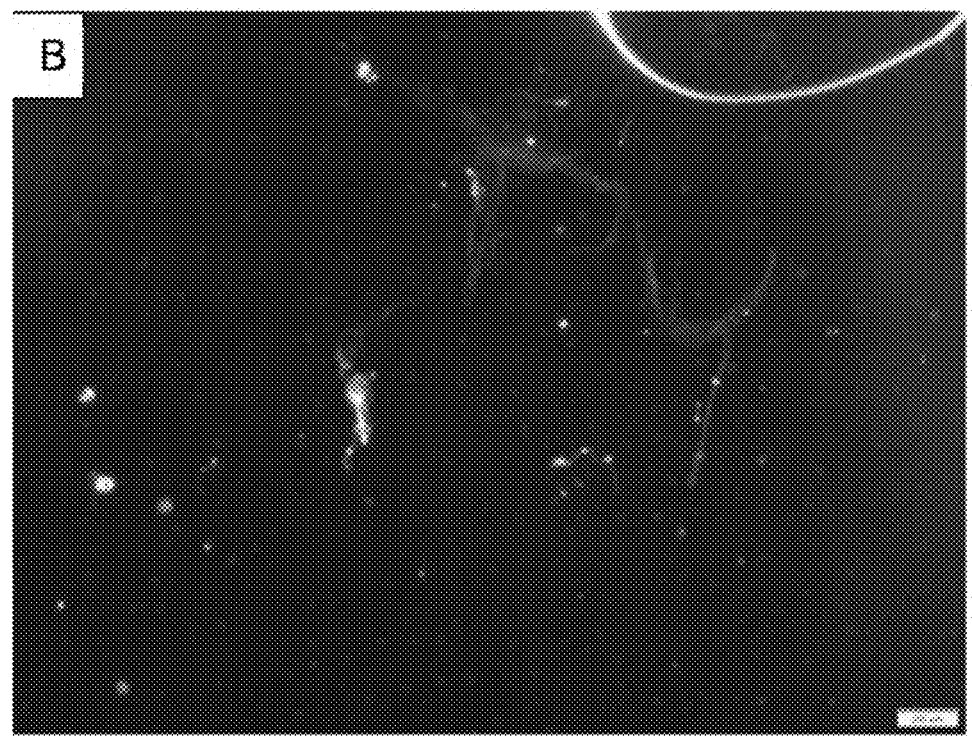
FIG. 4 depicts 4× microscopy images of water-in-water CMPs using linear polarized light microscopy.

FIGS. 3-4 show CMPs fabricated through water-in-water emulsion. FIG. 3 is a light microscope image with FIG. 4 being linear polarized light image of the same CMPs. The CMPs fabricated in this process appeared to form random structures. Again, FIG. 4 aids visualization of fabricated collagenous CMPs through polarized light microscopy.

WST1 Assay with Water-In-Water CMPs

Figure 5:
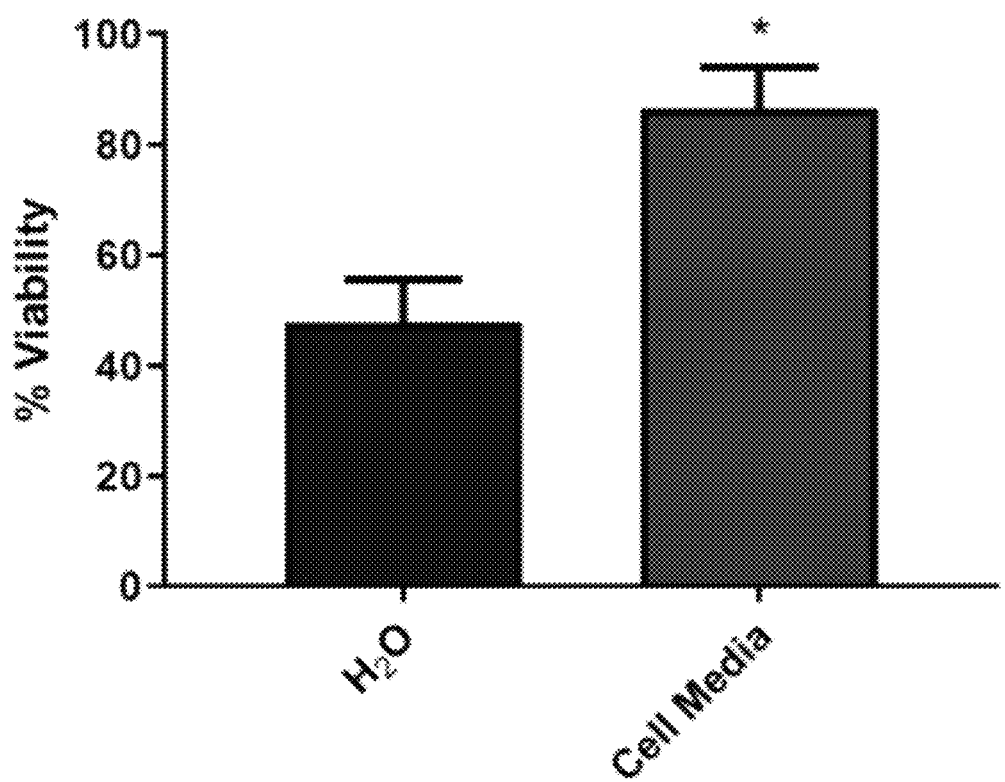
FIG. 5 depicts a 4-day WST-1 assay using water-in-water emulsion with L929 fibroblast cells. N=5. * indicates p≤0.0005.
Figure 6A:
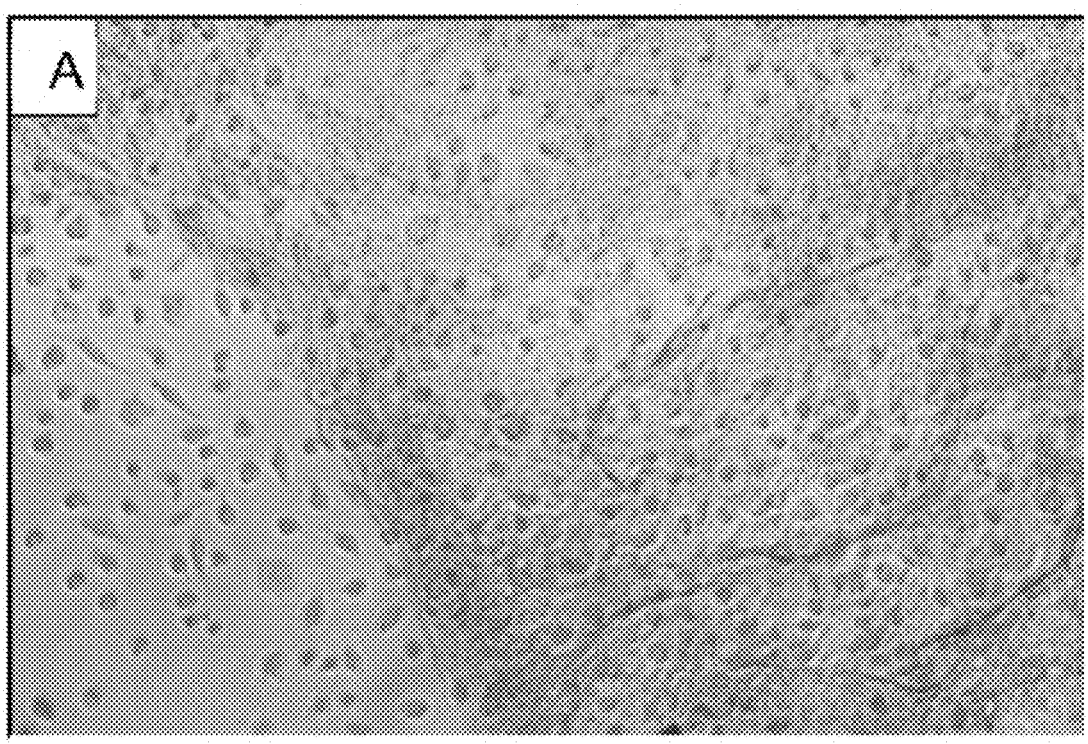
FIG. 6A is 10× light microscopy images of 4-day culture of L929 fibroblast cells with CMPs fabricated in $H_2O$.
Figure 6B:
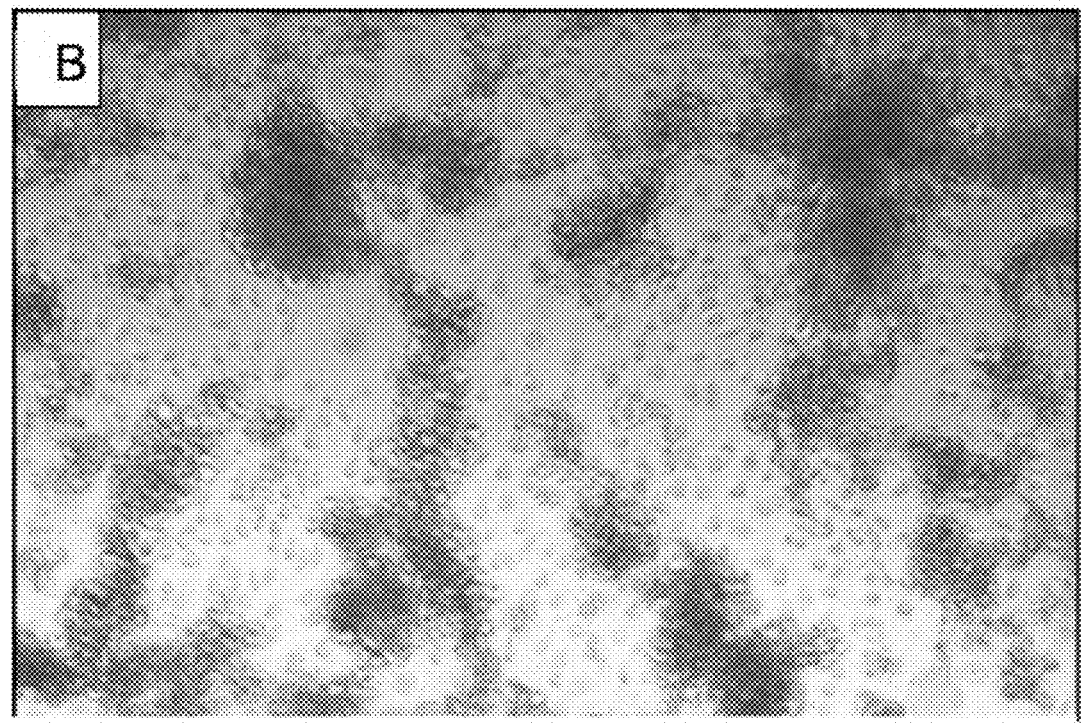
FIG. 6B is 10× light microscopy images of 4-day culture of L929 fibroblast cells with CMPs fabricated in cell media.

A 4-day WST1 assay was performed with CMPs emulsified in either H$_2$O or cell media and incubated with L929 fibroblast cells. At the terminal time point of 4 days, the group emulsified in cell media had a relative viability of 35% while the group emulsified in H$_2$O had a relative viability of 49% as shown in FIG. 5. There was a significant difference observed between the two groups ($p \leq 0.0005$). FIGS. 56A and 6B are images of the cells incubated with the CMPs fabricated in H$_2$O and cell media respectively. CMPs fabricated in H$_2$O appeared to form a layer on the bottom of the well plate while the CMPs fabricated in cell media appeared to remain in defined particles attracting cells to the surface of the particles after 4 days.

Discussion

Two methods of CMP fabrication were investigated using microscopy. One method of fabrication that was investigated was probe sonication of liquid collagen to form CMPs while the other method was the utilization of water-in-water emulsion. Both methods formed fibrilized particles analyzed using linear polarized light microscopy in FIGS. 1-4. Both methods are quick techniques to form CMPs with the sonication method generating CMPs immediately after sonication and water-in-water emulsion generating particles in 30 minutes.

A cell study was performed with both CMPs incubated in cell media prior to addition to the well plate. However, CMPs fabricated in cell media significantly demonstrated enhanced biocompatibility as compared to the CMPs fabricated in H$_2$O as shown FIG. 5. There may be some benefits of the CMPs being fabricated in cell media as compared to the water. It is possible that during the fabrication process, CMPs are loading or entrapping the liquid (water or cell media). Even though the CMPs are subsequently incubated in cell media prior to addition to the well plate, the higher percentage of cell media entrapped during fabrication is more cell friendly than the entrapped water. Additionally, the CMPs fabricated in cell media appear to maintain their shapes as individual particles while the CMPs fabricated in H$_2$O appeared to be reduced or unravel and form a collagenous layer on the bottom of the well plate as shown in FIG. 6A.

The cells appeared to be attracted to the surface of the CMPs fabricated in cell media as shown in FIG. 6B. An explanation for this enhanced biocompatibility may be due to the CMPs being loaded with a high concentration of cell media which is providing a sustained release of fresh media which is attracting cells or cells may prefer the collagen substrate relative to the polymer well plate. A higher concentration of cells can also be observed on the surface of the collagen relative to the exposed well plate in FIG. 6A.

In summary, two techniques of CMP fabrication—Collagen Microparticle Sonicator Fabrication and Water-in-water fabrication (both in water and cell culture media) were examined. Both techniques were quick and easy to use. A cell culture biocompatibility test with the water-in-water fabrication technique (both in water and cell culture media) demonstrated enhanced biocompatibility of CMPs in cell media.

Example 2. A Crosslinker-Free Technique Toward the Fabrication of Collagen Microparticles Summary Injectable collagen microparticles (CMs) have the potential to be an excellent tool to deliver various modulatory agents or to be used as a cellular transporter. A drawback has been the difficulty in producing reliable and spherical CMs. A crosslinker-free method to fabricate CMs was developed using liquid collagen (LC) in a water-in-oil emulsion process with varying concentrations of surfactant sorbitan monooleate (also known as span-80). Different emulsion times of up to 16-hours were utilized to produce the CMs. Visual microscopy and scanning electron microscopy were utilized to determine the morphology of the CMs. To determine the fibril nature of the CMs, focus ion beam milling, energy dispersive spectroscopy, and Fourier Transformation-Infrared spectroscopy were performed. A cell biocompatibility study was performed to assess the biocompatibility of the CMs. The results demonstrated that consistent spherical CMs were achievable by changing the sorbitan monooleate concentration. The CMs were fibrilized not only at the surface but also at the core. Both the 1-hour and the 16-hour emulsion time demonstrated biocompatibility and it appeared that the cells preferentially adhered to the CMs. This crosslinker-free method to fabricate CMs resulted in spherical, stable, biocompatible CMs, and could be an excellent technique for multiple tissue engineering applications.

Introduction

Recent advances in the field of musculoskeletal deficiencies, histogenesis, and chondro/osteoinduction are mainly attributed to the utilization of naturally occurring collagen as fillers. Collagen is the most abundantly found protein in the human body, with collagen type I, II, and III composing 80-90% of all collagen. The triple helix of type I collagen is composed of three peptide chains that have $\alpha 1$ and $\alpha 2$ subunits, having a characteristic repeating X-Y-Glycine sequence, with X and Y most commonly being proline and hydroxyproline respectively. A single triple helix conforms with two $\alpha 1$ subunits and one $\alpha 2$ subunit contributing to its design as an integral structural component and thus allowing collagen to be an excellent candidate for biomaterial applications.

Collagen is also commonly used in biomedical applications due to its excellent biocompatibility and is biodegradable with no harsh byproducts. Collagen can be processed in many forms and shapes using various processes including casting, molding, electrospinning, and 3D printing. While these processes can result in many different shapes and forms of the collagen structure, for tissue engineering applications, it is highly desirable for the collagen materials to be injectable as it allows minimal invasive surgeries, faster healing times, and less inflammation. Among all shapes, spheres of collagen, as microspheres, have attracted special attention due to their injectable characteristics.

Collagen microparticles (CMs) have been utilized in injectable form for tissue applications for recapitulation of cartilage, bone, blood vessel, and intervertebral disc development. In addition, the microparticles have also been used as a drug transporter for proteins such as bovine serum albumin, histone, bone morphogenetic protein 2, vascular endothelial growth factor, and transforming growth factor beta-3. Furthermore, CMs have not only been utilized to entrap and carry various proteins but have also been used to entrap and carry cells like chondrocytes and mesenchymal stem cells. For example, an interesting study describes the entrapment of undifferentiated and chondrogenic pre-differentiated mesenchymal stem cells (MSC) within CMs into an osteochondral defect rabbit model. It was demonstrated that regardless of whether the MSCs were undifferentiated or differentiated, the higher cell density resulted in better histological scores. Further, the study showed that undifferentiated and pre-differentiated MSCs at high cell densities produced hyaline cartilage. Even though there have been many biomedical applications for CMs, the fabrication of CMs is cumbersome and labor-intensive; current fabrication procedures require crosslinkers during emulsification which can lead to cytotoxicity or pipetting cycles that are time-consuming and produce non-injectable microparticles.

The current CMs fabrication procedures commonly utilized micropipetting of collagen or emulsion. For example, neutralized type I rat tail collagen was micropipetted onto a parafilm lined Petri dish; the collagen gelled into a spherical form under physiological temperatures and conditions. This technique suffers disadvantages as it requires individual pipetting cycles to obtain CMs, which is time-consuming and laborious. More importantly, the technique yields microparticles of different sizes ranging from 300 μm to 1000 μm. Others have worked on different fabrications to overcome this disadvantage and have utilized a water-in-oil emulsion process to fabricate CMs. Commonly, a collagen solution is added to an oil emulsion and allowed to stir for a set amount of time. Preceding work have used various oils such as corn oil, PDMS, paraffin oil, olive oil, paraffin/olive oil, and perfluorinated oil with surfactants such as polyoxyethylene (20) sorbitan monolaurate (also known as tween-20), sorbitan monolaurate (also known as span-20), sorbitan monooleate, and have also used a range of emulsion rates ranging from 300-1,200 rpm that have all contributed to changing the average CM diameters. By varying these parameters, prior publications have fabricated CMs of various sizes from several microns to 300 μm. One vital factor to consider is the use of crosslinking agents in forming CMs. These agents are used during the emulsification process to form stable CMs. Chemical crosslinking agents used to fabricate CMs with good stability include glutaraldehyde and EDC/NHS (1-Ethyl-3-[3-dimethylaminopropyl]carbodiimide hydrochloride)/N-hydroxysuccinimide. A disadvantage of the use of traditional chemical crosslinker glutaraldehyde is that they have long been shown to have cytotoxic effects. In addition, the use of chemical crosslinkers can also effect cellular adhesion to type I collagen. The use of EDC/NHS crosslinking on type I collagen inhibiting native-like cellular adhesion has been reported. They have proposed that the use of EDC/NHS crosslinking modifies the carboxylic acid groups on collagen altering divalent cation-dependent cell adhesion to cation-independent cell adhesion.

This disclosure describes CMs using a prefibrilized, liquid collagen (LC) solution to avoid the use of traditional crosslinking agents to maintain CM stability. LC was initially developed as a crosslinker-free soft tissue filler which fibrilizes in situ. Previous studies have suggested that LC remains in a prefibrilized state due to the inclusion of ethylenediaminetetraacetic acid (EDTA) which surrounds the collagen fibrils preventing the formation of a triple helix leading to fibrillization. Another possible explanation proposed is multiple ionic interactions occurring upon different regions along the individual collagen fibrils preventing fibrillization. Fibrillization of the collagen occurs when it is introduced into physiological tissue fluids resulting in the displacement of either the EDTA or the ions allowing for the formation of individual fibrils into its triple helix structure. Heat can also trigger the fibrillization of LC due to the collagen fibrils energetically preferring to fibrilize. The transition from liquid to a fibrilized network is visually evident as the LC transition from a clear liquid to a semi-solid opaque material maintaining the structural form. The advantages of utilizing LC include no toxic effects shown in vivo, and its inherent resistance to collagenase digestion, native tissue in-growth in vivo, and vascularization in vivo.

LC is an excellent material to use in the fabrication of CMs with a water-in-oil emulsion due to its ease of fibrillization under heated temperatures, relieving the need for a crosslinker. Herein is described a method to fabricate crosslinker-free CMs using sorbitan monooleate and olive oil emulsion. Sorbitan monooleate, a surfactant, was utilized to manipulate the CM diameter, and fibrillization of the CMs was achieved by emulsification at 35° C. due to the energetically favorable reaction within the solution. The results demonstrated that reproducible CMs were achieved and the size ranges can be manipulated by utilizing different concentrations of surfactant. The CMs demonstrated biocompatibility and stability over time. It is expected that these CMs will be able to serve as an injectable carrier of biomodulatory agents like stem cells, proteins, and drugs.

Materials and Methods

Fabrication of Liquid Collagen

Porcine collagen type I (10 mg/ml, Sunmax Biotechnology, Taiwan) was precipitated using 1.04 M sodium chloride (NaCl, 99.0%, Sigma Aldrich, MO). The precipitated collagen solution was then centrifuged at 3,500 rpm for 15 minutes. A white collagen pellet was formed at the bottom of the tube and the supernatant was poured off leaving a 150 mg collagen pellet. Fifteen ml of 0.5 M glacial acetic acid (99.7%, Fisher Chemical, KS) was added to the collagen pellet and allowed to sit overnight at room temperature to let the collagen pellet dissolve. The collagen/acetic acid solution was then placed in a 15 ml, 10 kDa molecular weight cutoff dialysis cassette (Thermo Scientific, IL) and immersed in an ethylenediaminetetraacetic acid (35 mM, EDTA, Fisher Chemical, KS)/$H_2O$ solution with a pH of 7.5 using sodium hydroxide (10 N, NaOH, Ricca Chemical Co., TX). The pH of the EDTA solution was checked and maintained at 7.5 daily until the pH no longer fluctuated from 7.5. The collagen solution was then removed and pH was tested to ensure it was set at 7.5.

Fabrication of Collagen Microparticles

Fifty ml of olive oil (Sigma Aldrich, MO) and correlating volume of sorbitan monooleate or sorbitan monostearate (also known as span-60) (Sigma Aldrich, MO) was added to a 100 ml round bottom flask. A 4 cm stir bar was added to the flask and placed on a stir/hot plate and set to 1150 rpm. The emulsion was allowed to equilibrate for 10 minutes. After 10 minutes, 1 ml of the LC solution was added dropwise using an 18-gauge plastic cannula. One hour after the LC addition, the stir plate temperature was set to 35° C. and allowed to stir for up to 16-hours. Preliminary studies show fibril formation occurring 1 minute after LC was added to 37° C. olive oil, data not shown. After the emulsion time was reached the collagen/oil solution was poured into a 50 ml centrifuge tube and centrifuged at 5000 rpm for 5 minutes. The oil was then removed and 25 ml 50% acetone (Fisher Chemical, KS) and 100 µl tween-20 (Sigma Aldrich, MO) was added to the tube to wash the CMs. The solution was vortexed for 1 minute and sonicated for 3 minutes. The solution was then centrifuged at 5,000 rpm for 5 minutes. The sample was washed 3 times using 50% acetone and tween-20 and then was washed 3 times using 1×PBS (Sigma Aldrich, MO). The CMs were stored in 15 ml 1×PBS and placed in a 4° C. refrigerator. They have been shown to remain stable for at least 10 months.

AuNP Conjugation to CMs

EDC/NHS crosslinking was utilized to conjugate 20 nm gold nanoparticles (AuNPs, $7.0 \times 10^{11}$ particles/ml, Ted Pella, CA) to CMs. ~$5 \times 10^3$ CMs were introduced to a 15 ml 30 mM EDC and 55 mM NHS solution for 5 minutes. 1 ml AuNPs were functionalized using 15 µM cysteamine. After CMs incubated for 5 minutes in crosslinking solution, the functionalized AuNPs were added to the CMs and left on a shaker table for 24 hours at 225 rpm. CMs were washed three times using PBS.

CM Diameter Characterization

To determine the effects of the emulsion time and surfactant concentration on CM diameter, an inverted light microscope (IX50, Olympus, PA) with a 4× objective was utilized to examine the CMs. A 1:1 ratio of CMs to Trypan blue (0.4%, Sigma Aldrich, MO) dye was added to help visualize CMs under the microscope. Images were captured using SPOT software and CM diameters were measured using ImageJ. At least 100 CM diameters were collected per group and analyzed.

Electron Microscopy Characterization

CM morphology was studied using a scanning electron microscope (SEM) (Scios DualBeam, Thermo Scientific, MA), 5 kV-15 kV was used to image the sample. Samples were placed in a fixative solution of 100 nM sodium cacodylate, 2% glutaraldehyde, and 2% paraformaldehyde (provided by the University of Missouri Electron Microscopy Core) for 30 minutes and washed three times with $H_2O$. Samples were then placed on carbon tape, and the liquid was allowed to evaporate for 1-hour at 40° C. prior to imaging for hydrated imaging. Critical point drying (CPD) was also used to image CMs. For CPD, samples were negative stained with osmium and coated with platinum once fixed on carbon tape. Focused ion beam (FIB) milling was utilized to create a cross-section to determine the fibril structure of the core of the CMs. A gallium ion beam was used during FIB milling. Additionally, energy-dispersive X-ray spectroscopy (EDS) was conducted on the CMs to identify the elemental composition of the CMs.

FTIR

Fourier-transform infrared spectroscopy (FTIR) was performed to verify the collagen fibril formation in the CMs. An ATR-FTIR (Nicolet 6700, Thermo Scientific, MA) was utilized. Ten replicates from each sample were analyzed by averaging 32 scans per sample at a resolution of 4 $cm^{-1}$ at room temperature. Samples were prepared by storage in a −20° C. refrigerator for 24 hours and lyophilizing using a Labconco FreeZone-1 for 24 hours.

Thermal Stability Analysis

Differential scanning calorimetry was conducted to determine the thermal stability of CMs. A Q2000 DSC (TA Instruments, DE) was used to determine the denaturation temperature from a non-reversing heat flow plot. Approximately 2-5 mg of lyophilized CMs were loaded into hermetic lid aluminum pans. Samples were tested from 5° C. to 105° C. with a ramp rate of 3° C. per minute. Universal Analysis software was used to determine the denaturation temperature.

Cell Biocompatibility

Cell biocompatibility testing was performed to verify the cellular viability of L-929 fibroblast cells (ATCC, VA) with CMs. L-929 murine fibroblast cells were cultured at 37° C. and 5% $CO_2$ in Eagle's Minimum Essential Medium (ATCC, VA) supplemented with horse serum (10%, ATCC, VA) and penicillin-streptomycin (200 U/mL, ATCC, VA). Cells were subcultured and given fresh cell media as needed. All assays were performed in a biological safety cabinet under sterile conditions.

Cell proliferation reagent WST-1 (Sigma Aldrich, MO) was utilized to assess the biocompatibility of the CMs. In this assay, tetrazolium salts were added to wells containing cells and CMs. The CMs were incubated in cell media for 24 hours at 37° C. before being added to a 96 well plate. $0.75 \times 10^4$ L-929 murine fibroblasts/well were added to a 96 well plate and 24 hours later CMs were added to the cell seeded well plate. Half of the medium in each well was replaced after 72 hours. At the terminal time point, WST-1 reagent was added to each well and the plates were incubated at 37° C. for 4 hours. After 4 hours, the media was removed from each well and absorbance readings were taken at 450 nm, with 600 nm filter, using a spectrofluorometer plate reader (Cytation 5, BioTek, VT). L-929 fibroblasts with no CM scaffold served as the 100% viability baseline.

Results

Influence of Surfactant Concentration on Microparticle Diameter

To understand the influence of sorbitan monooleate and sorbitan monostearate on the size of CMs, the fabrication was performed in various concentrations of sorbitan monooleate and sorbitan monostearate. Specifically, the concentrations were varied from 0 to 0.50% (v/v) for sorbitan monooleate and from 0 to 2.50% (w/v) for sorbitan monostearate. The mean, standard deviation, median, and size range of each concentration is also shown in Table 2 for sorbitan monooleate and Table 3 for sorbitan monostearate, both shown below. The average diameter and standard deviation of the CMs decreased with the increase in concentrations of sorbitan monooleate from 92.7±44.1 µm with 0% sorbitan monooleate to 22.7±12.9 µm with 0.35% sorbitan monooleate. Likewise with sorbitan monostearate, the average diameter from using 2.50% sorbitan monostearate reduced by 81 µm relative to not using sorbitan monostearate. Using a one-way analysis of variance (ANOVA) with a pairwise Tukey test ($p<0.05$), a difference in the average diameter of CMs was observed between 0.02%, 0.10%, 0.20% and 0.35% sorbitan monooleate concentrations.

TABLE 2

Mean, standard deviation, median, and size range of counted CMs for each concentration of sorbitan monooleate emulsion

| Sorbitan Monooleate Concentration (v/v %) | Mean (µm) | Standard Deviation (±) | Median (µm) | Size Range (µm) |
| --- | --- | --- | --- | --- |
| 0 | 92.7 | 44.1 | 86.3 | 18.0-222.0 |
| 0.02 | 86.1 | 40.0 | 83.0 | 18.9-188.3 |
| 0.10 | 60.3 | 29.6 | 57.2 | 18.1-139.3 |
| 0.20 | 35.9 | 13.6 | 33.3 | 18.4-85.3 |
| 0.35 | 22.7 | 12.9 | 20.8 | 8.0-85.2 |

TABLE 3

Mean, standard deviation, median, and size range of counted CMs for each concentration of sorbitan monostearate emulsion

| Sorbitan Monostearate Concentration (v/v %) | Mean (µm) | Standard Deviation (±) | Median (µm) | Size Range (µm) |
| --- | --- | --- | --- | --- |
| 0 | 118 | 43 | 119.5 | 37-252 |
| 0.01 | 134 | 57 | 117 | 50-278 |
| 0.10 | 53 | 18 | 52 | 8-111 |
| 1.00 | 38 | 15 | 36 | 5-69 |
| 2.50 | 37 | 14 | 35 | 10-77 |

Figure 7A:
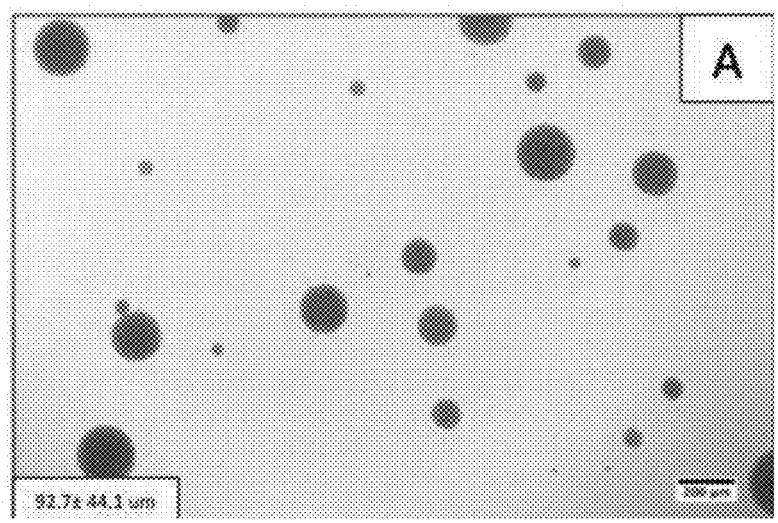
FIG. 7A is a 4× light microscopy image of 1-hour emulsion CMs with sorbitan monooleate. Scale bar=200 μm.
Figure 7B:
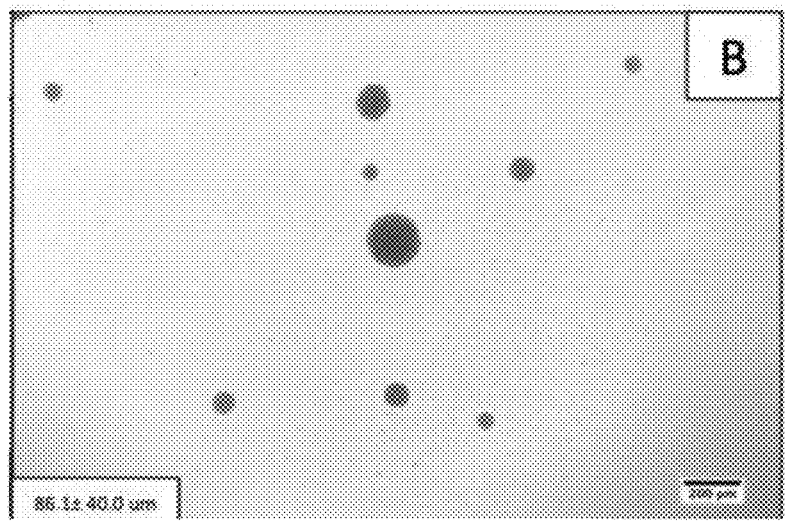
FIG. 7B is a 4× light microscopy image of 1-hour emulsion CMs with 0.02% sorbitan monooleate. Scale bar=200 μm.
Figure 7C:
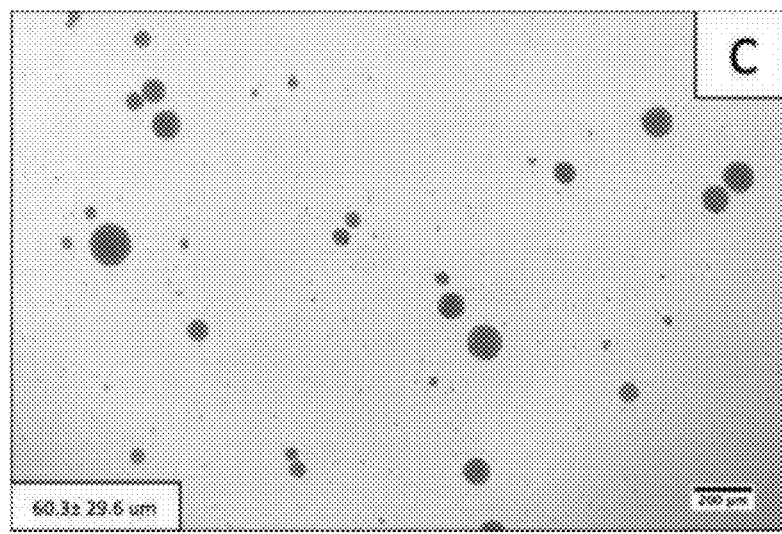
FIG. 7C is a 4× light microscopy image of 1-hour emulsion CMs with 0.10% sorbitan monooleate. Scale bar=200 μm.
Figure 7D:
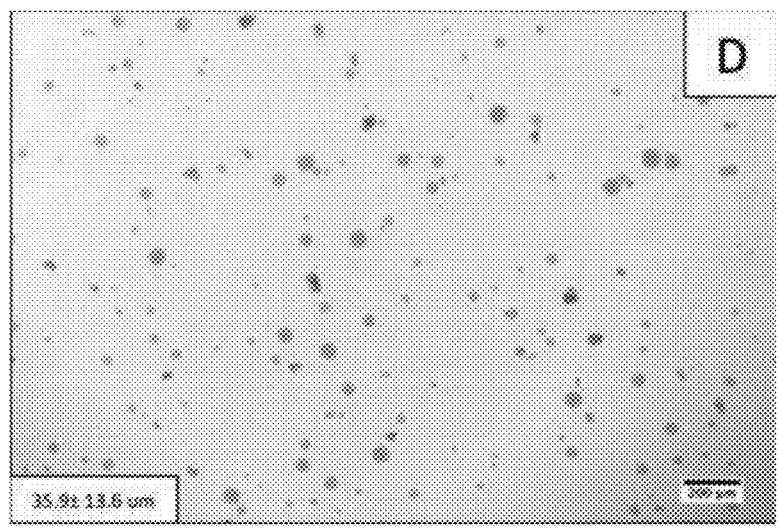
FIG. 7D is a 4× light microscopy image of 1-hour emulsion CMs with 0.20% sorbitan monooleate. Scale bar=200 μm.
Figure 7E:
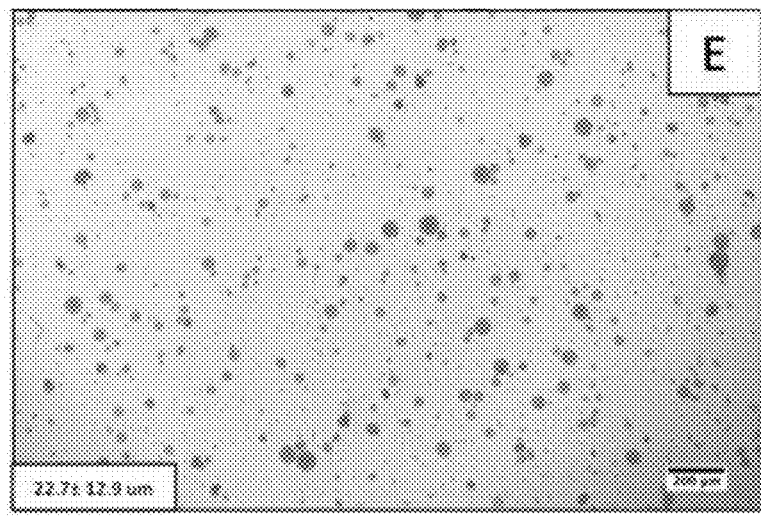
FIG. 7E is a 4× light microscopy image of 1-hour emulsion CMs with 0.35% sorbitan monooleate. Scale bar=200 μm.
Figure 7F:
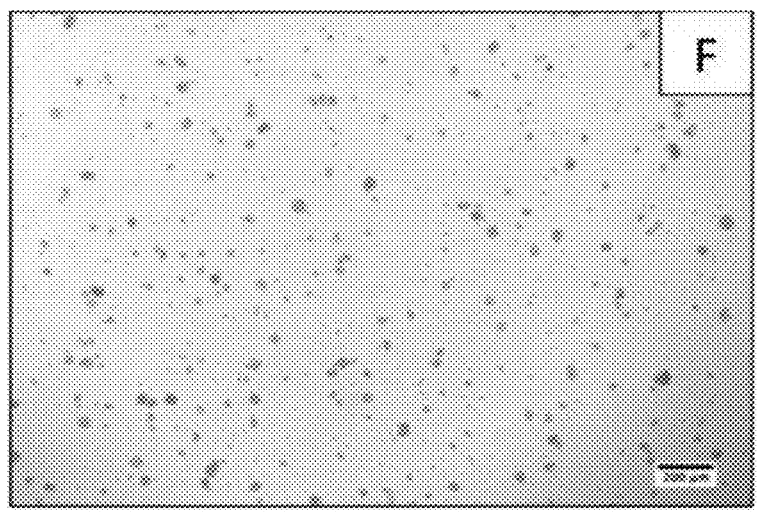
FIG. 7F is a 4× light microscopy image of 1-hour emulsion CMs with 0.50% sorbitan monooleate. Scale bar=200 μm.

FIG. 7A-7F includes 4× light microscopy images of CMs, which were dyed with trypan blue to increase visibility. The images demonstrate an increase in sorbitan monooleate concentration to the reaction mixture up to 0.3500, lead to a decrease in particle size, as evidenced by the figures. However, the particle size did not significantly decrease after increasing the concentration of sorbitan monooleate over 0.3500 (v/v). Interestingly, upon increasing the concentrations of sorbitan monooleate emulsion to 0.500% (v/v), the spherical morphology of the CMs was no longer maintained (FIG. 7F). Based on the result, 0.3500 (v/v) of sorbitan monooleate in the formulation was considered to optimal concentration for generating uniform size CMs.

SEM and EDS Characterization

Figure 8A:
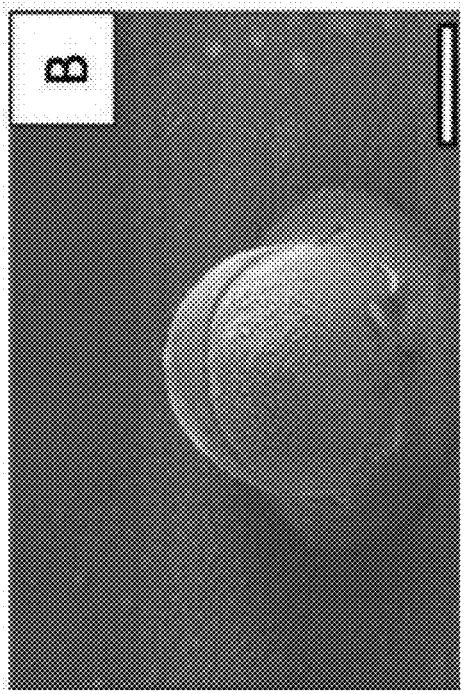
FIG. 8A is a SEM micrograph of a CM emulsified for 1-hour and prior to gallium FIB milling. Scale bar=40 μm.
Figure 8B:
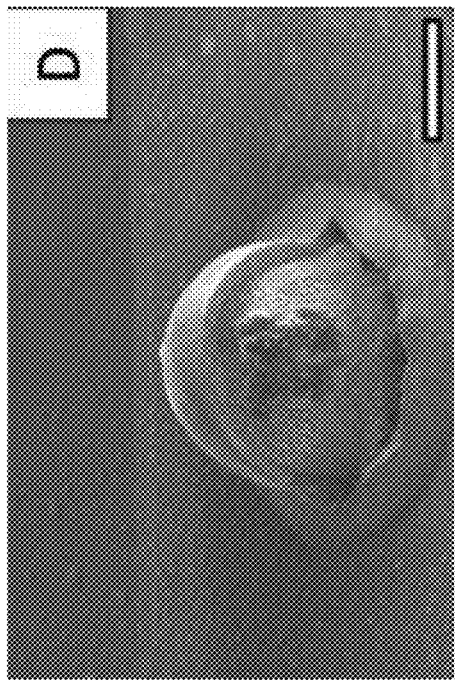
FIG. 8B, FIG. 8C, FIG. 8D, FIG. 8E, and FIG. 8F each depict a SEM micrograph of a CM emulsified for 1-hour with the image taken during gallium FIB milling requiring 29 minutes with a 3 nA current. Scale bar=30 μm.
Figure 8C:
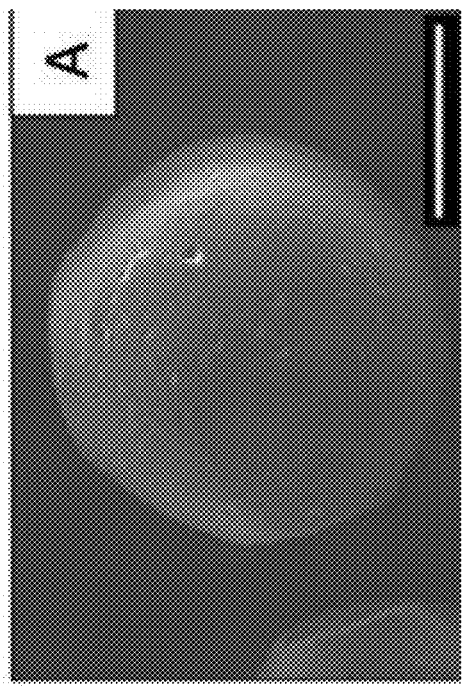
Figure 8D:
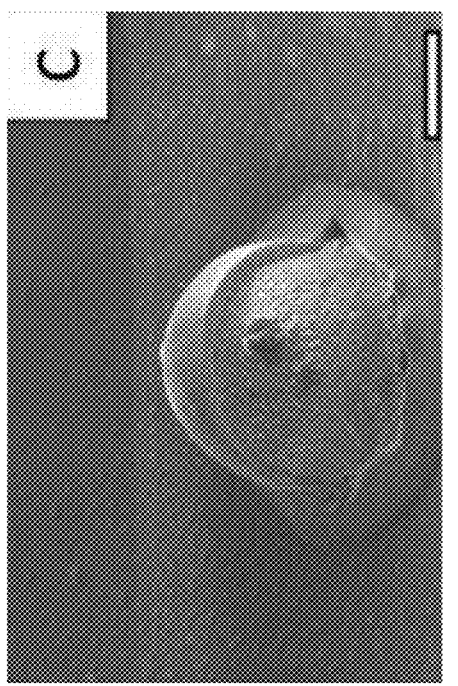
Figure 8F:
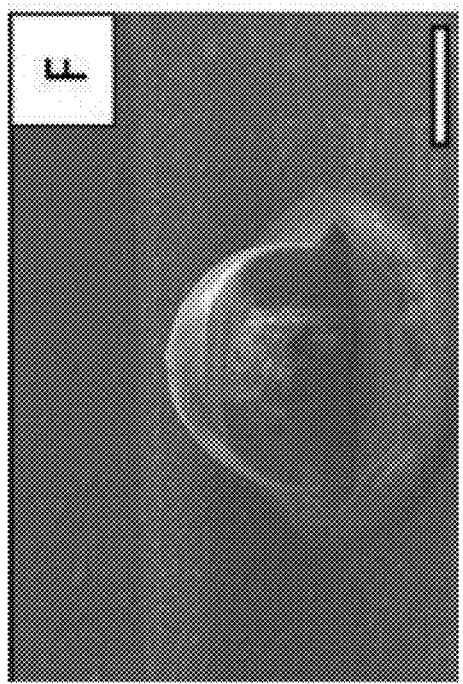
Figure 8H:
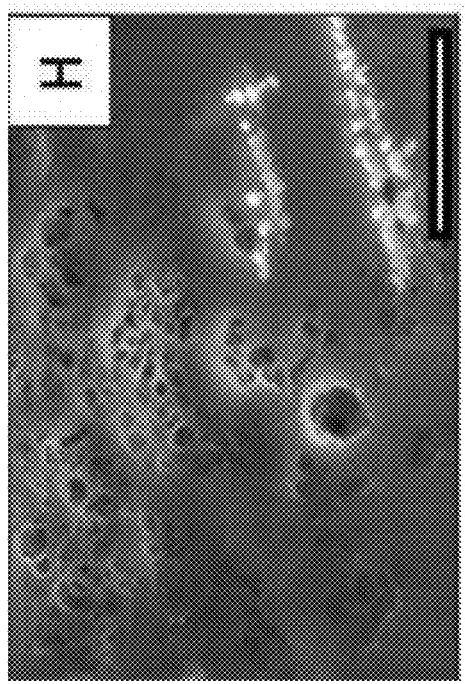
FIG. 8H is a high magnification image of a cross section from a portion of FIG. 8G. Scale bar=5 μm.
Figure 8E:
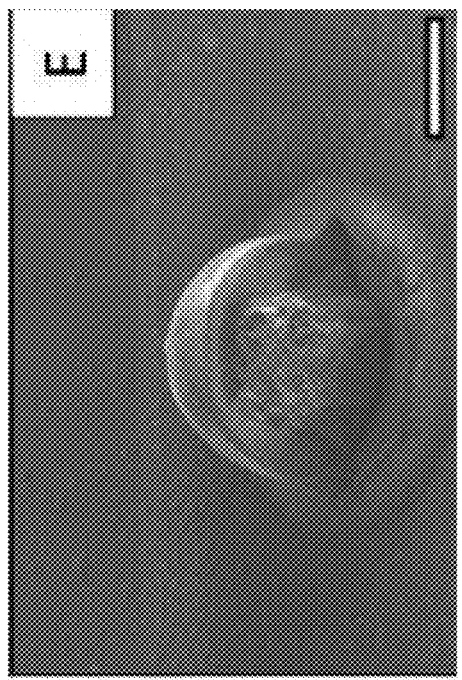
Figure 8G:
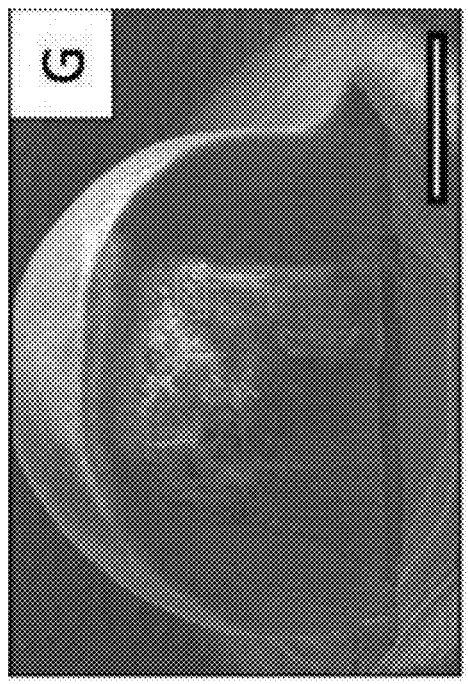
FIG. 8G is a cross section of the core of the CM emulsified for 1-hour and etched using gallium FIB milling. Scale bar=20 μm.

The spherical morphology of a hydrated, 1-hour CM emulsion is observed in FIG. 8A of the SEM micrograph. Collagen fibrils were not immediately evident based on the surface morphology of the CM. FIB milling was utilized to mill half of the of the CM, as shown in FIG. 8B-8H, to show the cross-section to reveal the morphology of the CM core. A progression from initial milling to fully milled CM (FIG. 8B-8H) took a total time of 29 minutes with a 3 nA current. After initial milling of the sphere, collagen fibrils were revealed. Further milling, as shown in FIG. 8C-8F, continued to reveal the collagen fibrils throughout the CM. A collagen network can be seen in FIG. 8H cross-section along with white salt crystals.

Figure 9A:
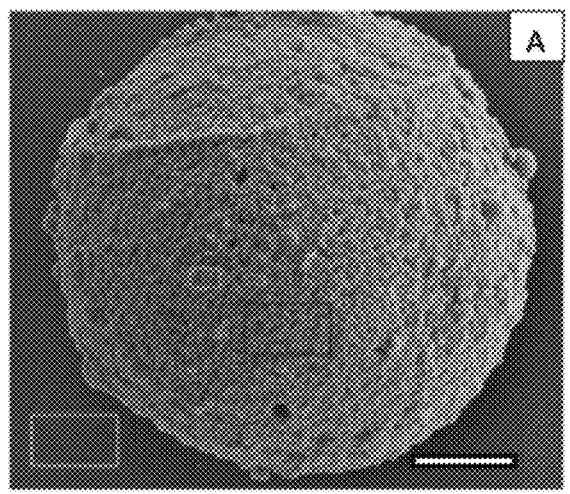
FIG. 9A is a SEM micrograph of a CM emulsified for 8-hours at 9,000× magnification of the CM. Scale bar=5 μm.
Figure 9B:
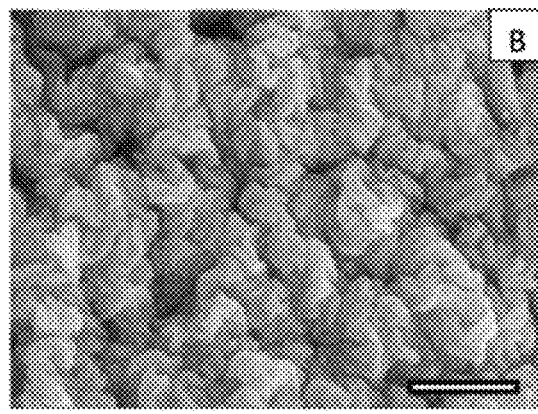
FIG. 9B is a SEM micrograph of a CM emulsified for 8-hours at 80,000× magnification of CM of a region of FIG. 9A. Scale bar=500 nm.
Figure 9C:
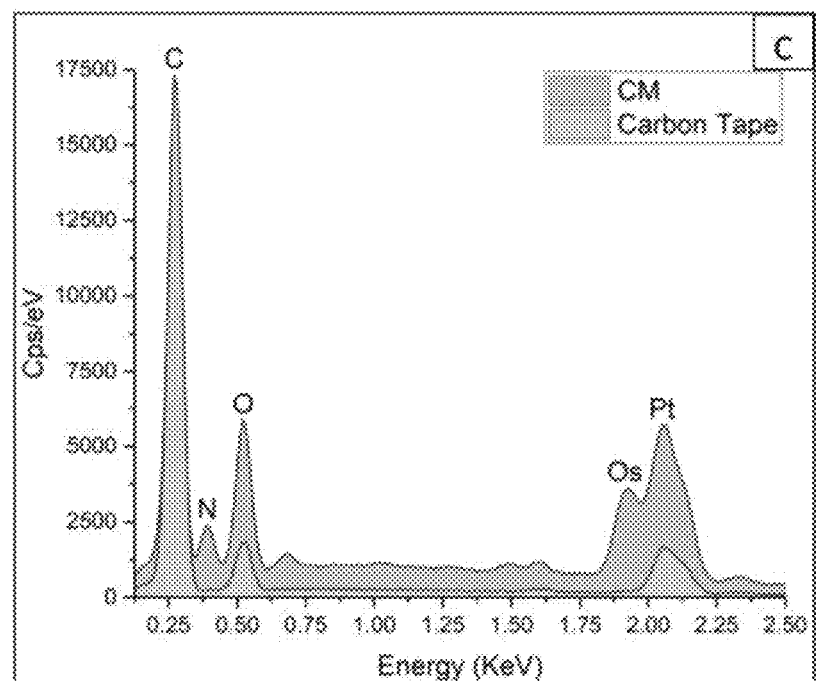
FIG. 9C depicts an EDS spectrum acquired from the CM and on carbon tape from FIG. 9A.

FIG. 9A is an SEM micrograph of an 8-hour CM emulsion that has been fixed and critically point dried. Collagen fibrils appear to be evident on the surface of the CM in FIG. 9A. FIG. 9B is a magnified view of the CM within the smallest of the three boxes in FIG. 9A. Visually these fibrils appear to be a mature fibrilized network maintaining a spherical structure. FIG. 9C is an EDS spectrum acquired on the surface of the CM and the carbon tape as a background spectrum. A strong nitrogen signal was acquired from the CM relative to the carbon tape background. A nitrogenous peak lends further evidence of the composition of the CM is collagen due to collagen being the only material containing nitrogen during the fabrication process.

FIG. 10A-10C is another SEM micrograph of a critically point dried CM. This CM was conjugated with 20 nm AuNPs using EDC/NHS conjugation. FIG. 10A is an SEM micrograph of the overall structure of the CM. The fibril structure is evident. FIG. 10B is a backscatter electron micrograph. The box is the region imaged in FIG. 10C. FIG. 10C provides a closer image of the detailed fibril structure of the CM. The light spots on the backscattered electron image are AuNPs that were conjugated on the CM. The AuNPs appear to be fairly homogenous over the whole surface of the CM. This provides evidence that AuNPs can be conjugated to CMs through EDC/NHS conjugation.

FTIR Analysis

Figure 11:
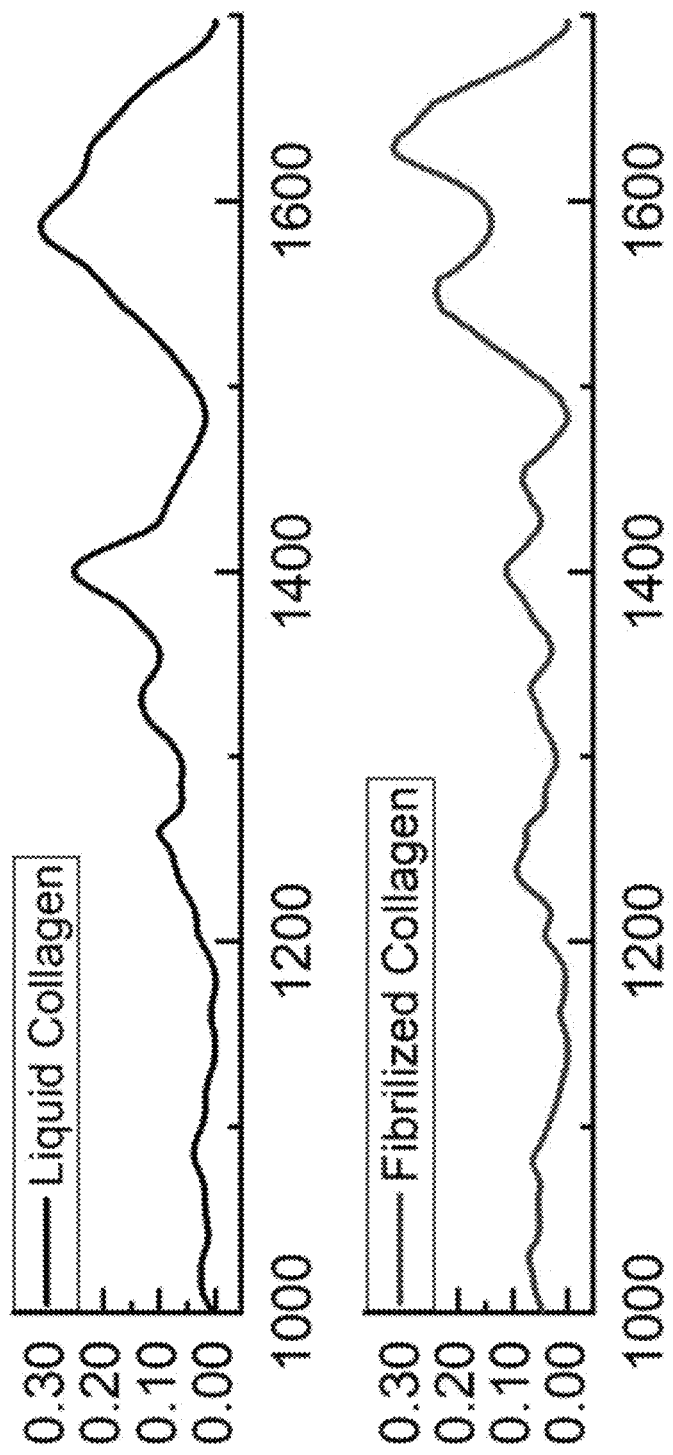
FIG. 11 depicts FTIR spectra of prefibrillized liquid collagen, fibrillized collagen, 1-hour emulsion CM with 0% sorbitan monooleate, 16-hour emulsion CM with 0% sorbitan monooleate, 16-hour emulsion CM with 0.35% sorbitan monooleate, and 1-hour emulsion CM with 0.35% sorbitan monooleate.
Figure 11:
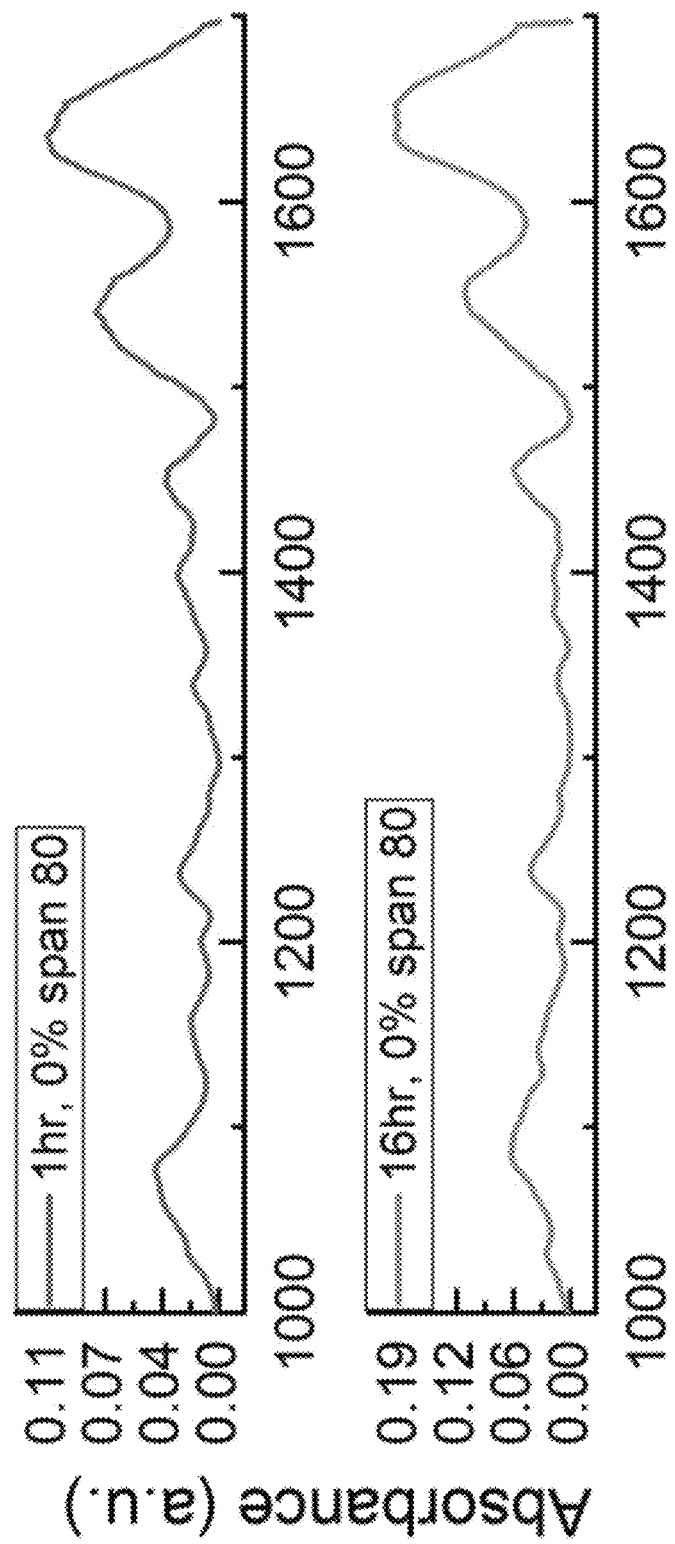
Figure 11:
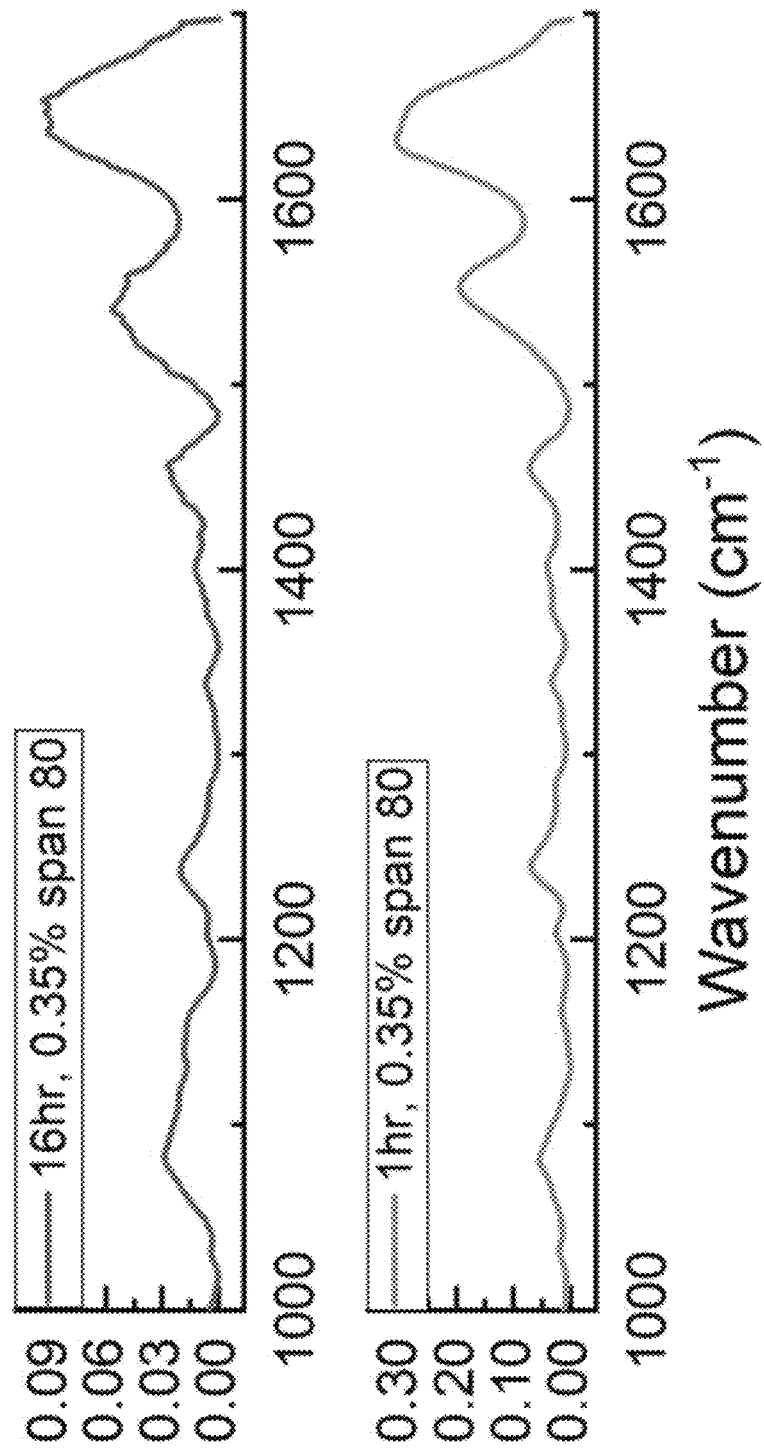

FTIR spectra from 1,700-1,000 cm-1 were acquired from six separate samples to determine the fibrilized nature of the CMs. The first sample tested was LC, which was added to the olive oil emulsion to form the CMs. The second sample was of the fibrilized collagen. To prepare the fibrilized collagen, LC was immersed in water for 24 hours to form a fibrilized collagen structure. The results, as shown in FIG. 11, demonstrated that the fibrilized collagen and the CM samples had similar characteristic peaks. Collagen characteristic peaks were found at amide I between 1700-1600 cm-1, amide II between 1600-1500 cm-1, and amide III between 1300-1180 cm-1 corresponding to (C=O) stretching, (C—N) stretching and (N—H) bending, and (C—N) stretching, (C—H) bending and (C—C) stretching.

While the CMs spectra mimic that of the fibrilized collagen's spectra with peaks found at the amide I, amide II, and amide III absorption bands, the LC had two peaks at 1585 cm-1 and 1400 cm-1 with a shoulder at 1630 cm-1. After fibrillization of the collagen, the 1585 cm-1 and 1400 cm-1 peaks are reduced and thereby revealing amide I and amide II absorption bands in the fibrilized collagen and CM samples.

Thermal Stability Analysis

Differential scanning calorimetry was utilized to determine the thermal stability of fabricated CMs. One and 16 hour emulsion with and without 0.35% sorbitan monooleate CMs were analyzed in this study which can be observed in FIG. 12. CMs without the addition of sorbitan monooleate were thermally more stable than samples emulsified with sorbitan monooleate. The 16 hour emulsion sample without sorbitan monooleate was the most thermally stable sample with an average denaturization temperature of 60.1° C. Both the 1 hour and 16 hour emulsion with 0.35% sorbitan monooleate had very similar denaturization temperature at 41.6° C. and 41.0° C. respectively. Both samples fabricated in the sorbitan monooleate solution had significantly lower denaturization temperature than both sampled fabricated without sorbitan monooleate.

Cell Viability

Figure 13A:
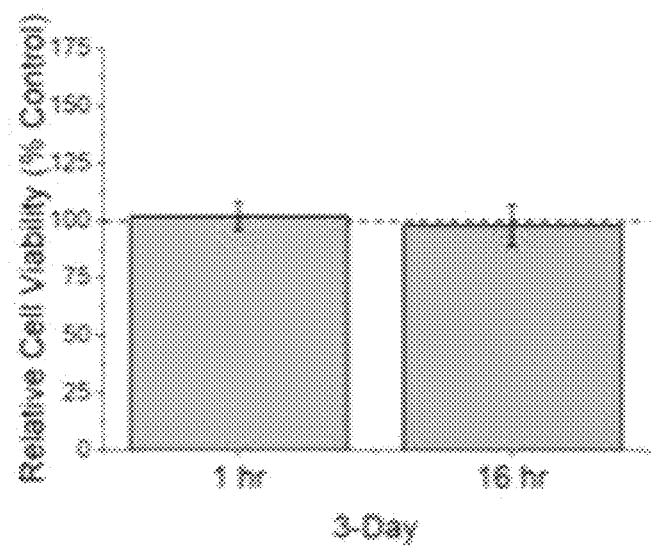
FIG. 13A depicts WST-1 cell viability assay at a 3-day timepoint using L929 fibroblast cells.
Figure 13B:
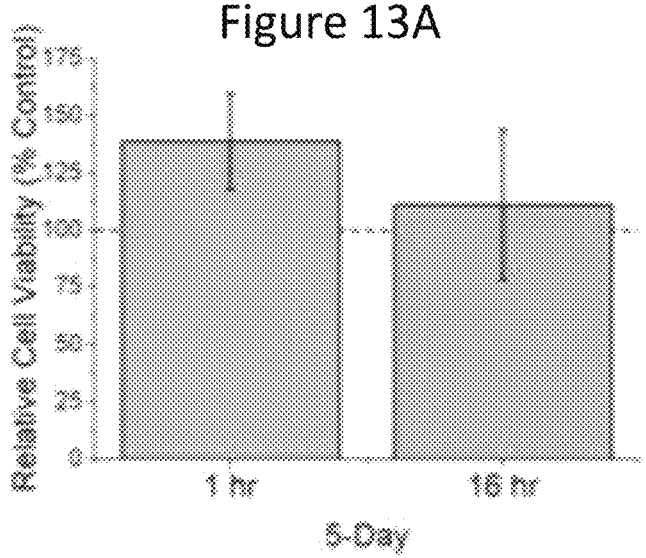
FIG. 13B depicts WST-1 cell viability assay at a 5-day timepoint using L929 fibroblast cells.
Figure 13C:
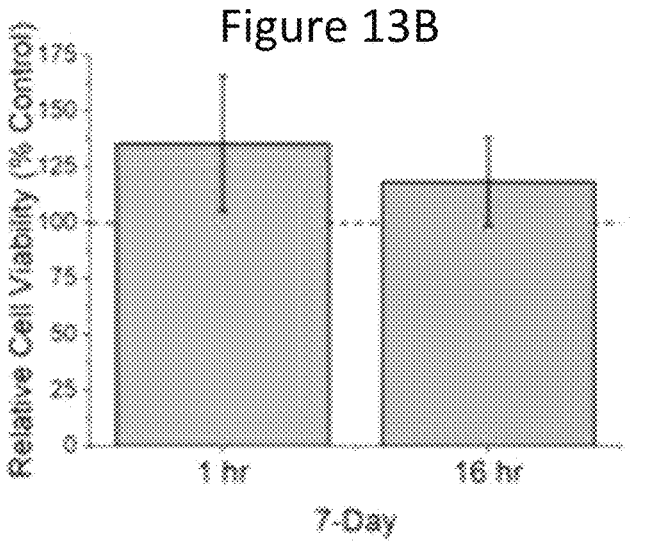
FIG. 13C depicts WST-1 cell viability assay at a 7-day timepoint using L929 fibroblast cells.
Figure 13D:
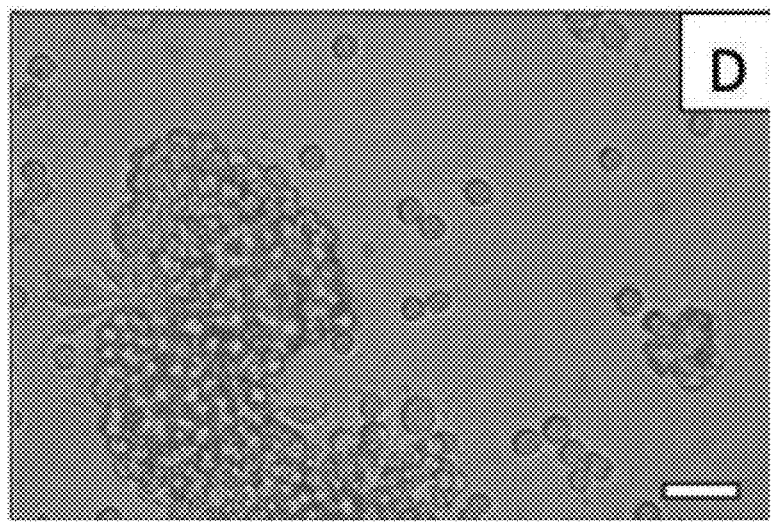
FIG. 13D is a 20× light microscopy image of L929 fibroblast cells plated for 3 days on CMs made with a 1-hour emulsion and 0.35% sorbitan monooleate. Scale bar=50 μm.
Figure 13E:
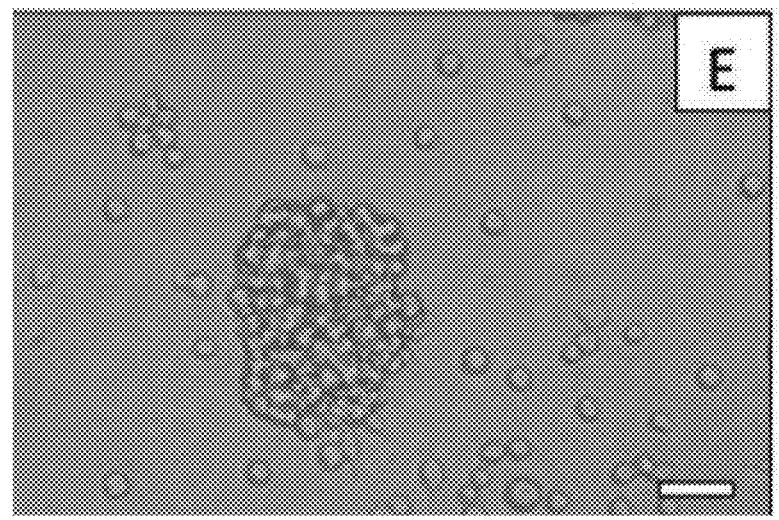
FIG. 13E is a 20× light microscopy image of L929 fibroblast cells plated for 3 days on CMs made with a 16-hour emulsion and 0.35% sorbitan monooleate. Scale bar=50 μm.
Figure 13F:
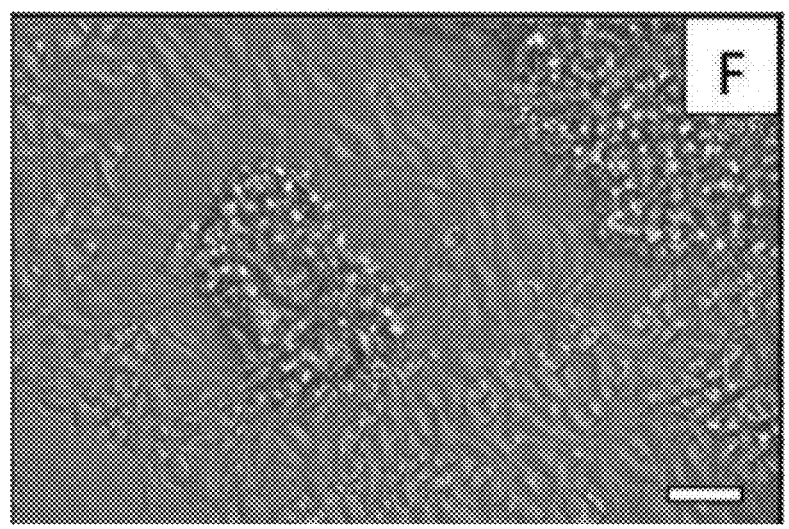
FIG. 13F is a 20× light microscopy image of L929 fibroblast cells plated for 5 days on CMs made with a 1-hour emulsion and 0.35% sorbitan monooleate. Scale bar=50 μm.
Figure 13G:
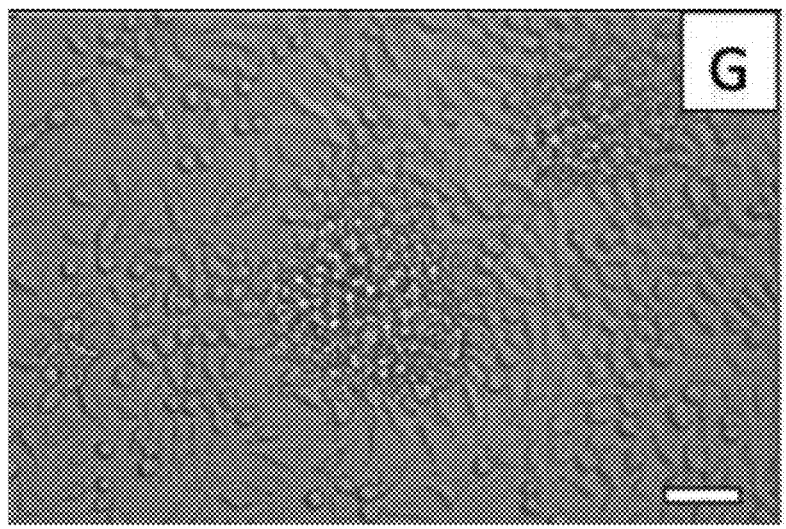
FIG. 13G is a 20× light microscopy image of L929 fibroblast cells plated for 5 days on CMs made with a 16-hour emulsion and 0.35% sorbitan monooleate. Scale bar=50 μm.
Figure 13H:
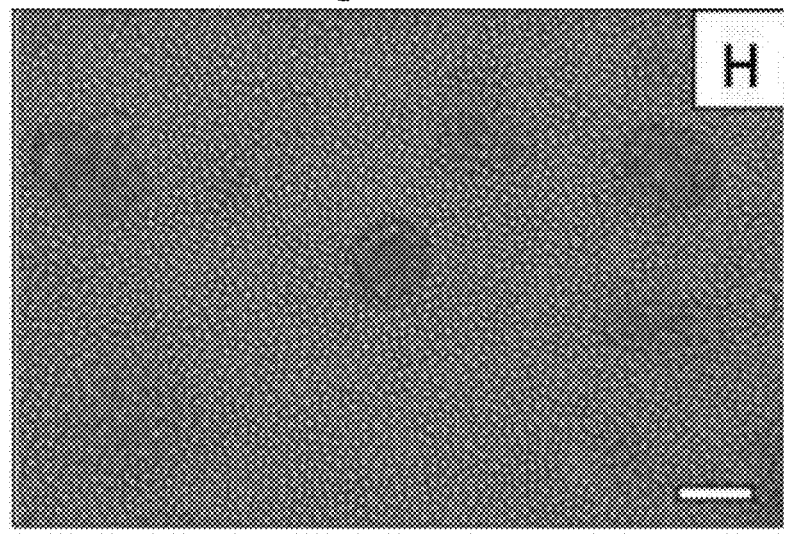
FIG. 13H is a 20× light microscopy image of L929 fibroblast cells plated for 7 days on CMs made with a 1-hour emulsion and 0.35% sorbitan monooleate. Scale bar=50 μm.
Figure 13I:
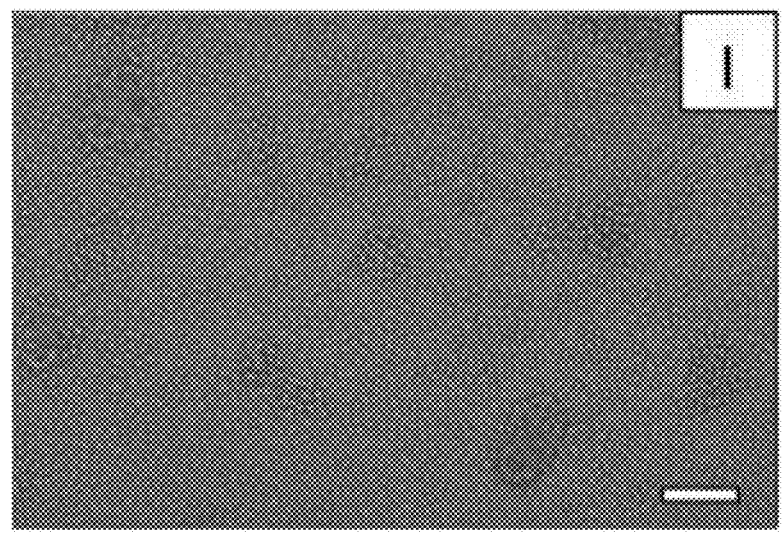
FIG. 13I is a 20× light microscopy image of L929 fibroblast cells plated for 7 days on CMs made with a 16-hour emulsion and 0.35% sorbitan monooleate. Scale bar=50 μm.

To evaluate the cellular toxicity of CMs fabricated in this work, a WST-1 cell viability assay was performed. CMs emulsified for 1 hour and 16 hours using 0.35% sorbitan monooleate were used. This work also examined if the CM emulsion time affected fibroblast cell viability over 7 days. Even though the CMs form after 1-hour of emulsion time, it was desirable to determine if CMs would begin to denature at the longer emulsion times and thus become less biocompatible. The 1-hour emulsion time was compared with an emulsion time of 16 hours. L-929 fibroblast cells were incubated with the CMs at 3, 5, and 7 day time points. Untreated L-929 fibroblast cells were used as control. The results demonstrated that there was no statistical significance between either group (1-hour or 16-hour emulsification time) relative to cells alone but inferences can be made upon the trend in cellular viability and visually how the cells interacted with the CMs during culture. After 3 days, as shown in FIG. 13A, both the 1-hour and 16-hour CMs demonstrated equivalent cellular viability as compared to that of the control (set at 100% viability). Both FIGS. 13D and 13E show fibroblasts adhering to the surface of CMs. After 5 days, FIG. 13B, both the 1-hour and 16-hour CMs showed overall increased viability in comparison to the control. FIGS. 13F and 13G showed significant coverage of fibroblast cells on the CMs with elongation of the fibroblasts extending from the CMs. At 7 days, FIG. 13C, both 1-hour and 16-hour emulsions maintain a similar viability advantage in comparison to the control. FIGS. 13H and 13I show a high density of fibroblasts covering the bottom of the well plate and complete coverage on the surface of CMs.

Discussion

Type I collagen is a triple helix, polypeptide chain protein that can be easily processed in a variety of forms. Processing collagen as an injectable fibrilized material for tissue engineering applications is advantageous not only due to collagen's excellent biocompatibility but also due to its ability to integrate with tissue in vivo, forming a template for cellular attachment and resulting in no harmful byproducts. However, the injectability of bulk collagen is problematic mainly due to its high viscosity; therefore, researchers have processed collagen in different forms such as microparticles to ease injectability. CMs are versatile materials but the limitations in terms of fabrication, such as the need for crosslinkers during emulsification and the limited ability to inject CMs fabricated via individual pipetting cycles, creates an opportunity to utilize liquid collagen to fabricate CMs. To overcome the limitations, a simple, crosslinker free method to fabricate CMs was developed with reproducibility for a wide range of musculoskeletal applications using LC.

Controlling the size of CMs during the fabrication process to create uniform sizes is critical for tissue engineering applications particularly if the CMs are entrapped with additional biomodulatory agents or cells. The release of biomodulatory agents and the survivability of cells can be controlled with greater accuracy relative to size uniformity in correlation to the release kinetics of a sphere. A wide range of CM sizes can result in a bulk release or delayed release of agents and thus may not achieve the therapeutic effect or even may result in cytotoxicity. In this work, the average diameter and standard deviation of the CMs was better controlled by utilizing sorbitan monooleate. The use of sorbitan monooleate resulted in a decreased CM diameter and standard deviation by decreasing the interfacial tension between water and oil seen in Table 2. Similarly, the effect of sorbitan monostearate on CM fabrication during emulsion can be observed in Table 3. Sorbitan monooleate was preferred and utilized in further studies due to its ability to fabricate smaller and more uniform particles relative to sorbitan monostearate. Sorbitan monostearate is also in a solid form and takes more time to dissolve in solution whereas sorbitan monooleate is in a liquid form and can immediately be added to the emulsion. FIG. 7A-7F demonstrated the influence of increasing concentrations of sorbitan monooleate during the CM fabrication process. The increased concentration of sorbitan monooleate proportionally led to a decrease in CM average diameter and standard deviation; however, CM spherical morphology was lost after increasing the sorbitan monooleate concentration over 0.35%.

Evidence to support a collagenous fibrilized network within the CM was two-fold. First, SEM imaging of 1-hour and 8-hour CM emulsions provided evidence of collagen fibrillization. The inspection of FIG. 8A with the 1-hour emulsion time demonstrated a smooth surface. Uncovering the surface of the 1-hour emulsion CM using FIB milling, FIG. 8B-8F, provided evidence of a collagen network at the core of the CM.

Through critical point drying in FIGS. 9A and 9B of an 8-hour emulsion CM, a collagenous network was visually apparent. An additional study was performed to verify the composition of CMs using EDS. EDS identified the elemental composition of an 8-hour CM emulsion on the surface as shown in FIG. 9C.

A nitrogenous peak was indicated on the surface of the CM. Nitrogen is a unique element to collagen during the CM fabrication process; thus further confirming the collagenous network created during fabrication.

FIG. 10A provides further evidence of a fibril structure of CMs while also verifying conjugation of AuNPs to CMs. FIGS. 10B and 10C are both backscattered images of the CM. The light deposits found on the surface of the CM are AuNPs. The AuNPs are fairly distributed throughout the surface of the CM. Previous work with AuNPs have shown them to be free radical scavengers along with promoting cell migration and attachment which may all be advantageous attributes for the CMs.

The second method utilized to identify fibrilized collagen within the CM was FTIR analysis as shown in FIG. 11. The FTIR scans of the CMs were compared to that of the LC and fibrilized collagen. The CMs scans mimicked that of fibrilized collagen scans, which indicates the fibrilized nature of the CMs. Characteristic peaks of collagen reported in literature also correlated with the peaks identified in the CM scans. An FTIR spectra of porcine collagen has been reported. The spectra obtained correlated almost identically to the spectras of the fibrilized collagen and CM samples of this disclosure. There were observable differences between the LC and the fibrilized collagen. For the LC, a single peak was identified at 1585 cm$^{-1}$ while the fibrilized collagen and the CMs displayed two individual peaks at 1635 cm$^{-1}$ and 1545 cm$^1$, which corresponded to amide I and amide II respectively. Also, the LC sample had a significant peak at 1400 cm$^{-1}$ relative to all other samples. Literature suggests that a peak at 1400 cm$^{-1}$ is attributed to CH$_2$ bending from glycine residues and also symmetrical stretching of (COO—) from glutamate and aspartate found in LC. The diminishment in the intensity of 1400 cm$^{-1}$ may be due to dehydration of type I collagen during the crosslinking or fibrillization stage. Fibrillization of collagen leads to dehydration. It was observed that these CMs demonstrated a decrease in the 1400 cm$^{-1}$ peak, which can be attributed to fibrillization; these results validate the fibrillization of the CMs.

Figure 12:
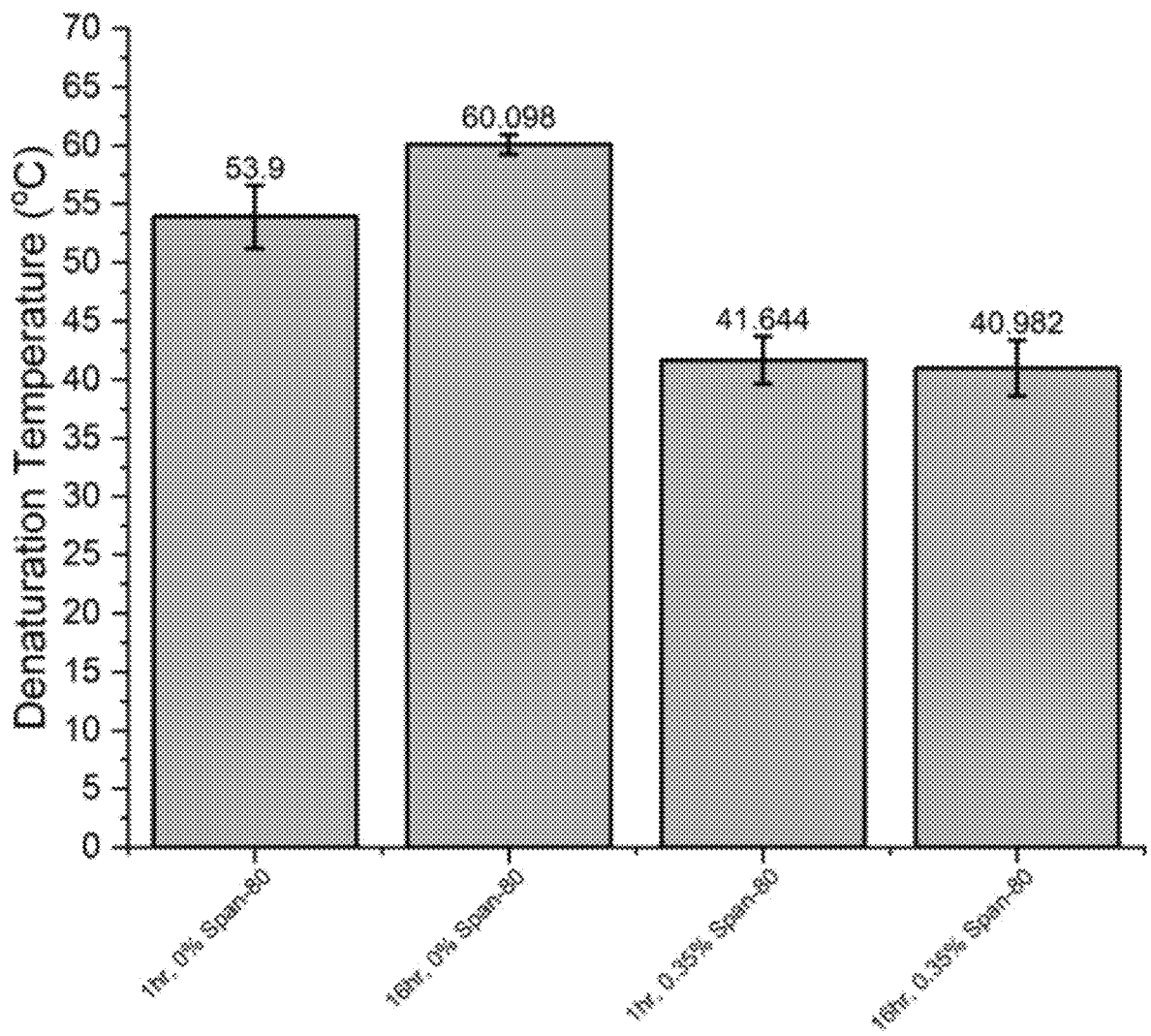
FIG. 12 depicts DSC results providing data on denaturization temperature of various preparations of CMs. N=5.

Differential scanning calorimetry was used to determine the thermal stability of the CMs as shown in FIG. 12. An emulsion of 1 or 16 hours with or without 0.35% sorbitan monooleate was analyzed in this study. Both samples without sorbitan monooleate had a significantly higher denaturization temperature with the 16-hour emulsion without sorbitan monooleate had the highest average denaturization temperature of 60.1° C. Both samples with sorbitan monooleate performed very similarly with denaturization temperature for the 1-hour and 16-hour emulsion being 41.6° C. and 41.0° C. respectively. While the denaturization temperatures are lower for both samples with sorbitan monooleate they are still above the average temperature of the body at 36.6° C. allowing these samples to maintain their structure if implemented in vivo.

It was imperative that the CMs demonstrated biocompatibility. Cellular viability was performed to determine the compatibility of CMs with L-929 fibroblast cells. Three, five, and seven-day time points were evaluated and compared between the 1-hour and 16-hour CM emulsion times. At 3 days, both the 1-hour and 16-hour CM emulsions were equivalent in cellular viability to the negative control (FIG. 13A). At days 5 and 7, there was an overall trend toward enhanced viability compared to the negative control by both 1-hour and 16-hour CM emulsions (FIG. 13D and FIG. 13G). Upon visual inspection of the cells and the CMs over 7 days, it appeared that the cells have an attraction towards the CMs. As shown in FIG. 13D-13I, cells were more clustered on the CMs than on the bottom of the 96-well plate. The CMs may play a role in enhancing cellular proliferation. While no quantitative data was recorded, the cells appeared to wrap around the surface of the CMs and gave the appearance of being adherent to the surface of the CMs. The cells also appeared to be extending from the CMs and creating a cellular network. These results were similarly observed by others when incubating CMs with NIH3T3 cells.

These findings demonstrated that fibroblast cells have an affinity for the crosslinker-free CMs. The cells may be experiencing a native-like recognition and cell attachment due to a larger number of integrin moities of the type I collagen along with a more open network as compared to collagen that has various chemical crosslinking agents. The use of CMs could be used as possible bioactive agent carriers and cell transporters. The extensive work performed with adipose-derived mesenchymal stem cells (ADSC) on chondrocyte cells and on the differentiation into chondrocyte cells was examined. The CMs disclosed herein are uniquely suited as an injectable transporter for ADSCs into osteoarthritic tissues due to their injectable size and their affinity for cellular adherence.

In summary, a crosslinker-free method to fabricate CMs was developed. CMs were developed using a LC in a water-in-oil emulsion process. The size of the CMs was modified by using sorbitan monooleate. Fibrilized CM structures were obtained for up to 16-hour emulsion times. The spherical and fibrilized nature was confirmed via SEM. EDS analysis confirmed CMs composition through the identification of a unique nitrogenous peak to collagen. FTIR analysis also confirmed collagen transitioning from a pre-fibrilized state prior to the emulsion and subsequently to a fibrilized state after emulsion. The CMs exhibited a thermally stable, biocompatible material for both 1-hour and 16-hour emulsion times and it appeared that the cells preferentially adhered to the CMs. This crosslinker-free method to fabricate CMs resulted in spherical, stable, biocompatible CMs.

Example 3: Fabrication of Targeted Collagen Microparticles for Mitigation of Posttraumatic Osteoarthritis Introduction Osteoarthritis (OA) is a progressively degenerative joint disease leading to loss of articular cartilage and creating joint instability. This degradation can cause severe disability; today over 27 million Americans have been diagnosed with clinical OA. About 12% of symptomatic OA can be attributed to posttraumatic osteoarthritis (PTOA) at a cost to the U.S. of around $3 billion. In the events following PTOA, chondrocyte cells found in the articular cartilage in close proximity to the trauma undergo cell death namely through necrosis. Cells surrounding the trauma site tend to exhibit a hypertrophic phenotype that expresses a host of catabolic enzymes that can further dysregulate chondrocyte cells eventually leading to apoptosis and cause degradation of articular cartilage extracellular matrix (ECM). Interleukin-1β (Il-1β) is particularly detrimental to chondrocyte cells in the progression of PTOA. Catabolic chondrocytes begin to express cytokines and chemokines like tumor necrosis factor (TNF)-a, Il-1β, Il-6, Il-8, and receptor activator of NF-kβ ligand (RANKL), which perpetuates and enhances articular damage. Work has also shown Il-1β to be a major contributor in the progression of PTOA, particularly in the upregulation of known collagenases like matrix metalloproteinases −3 and −13 and is also associated with the downregulation of articular cartilage components like type II collagen and aggrecan by inhibiting anabolic activities of chondrocytes.

Reactive oxygen species (ROS) are a grouping of molecules and free radicals with one unpaired electron derived from molecular oxygen. Produced ROS can dysregulate or signal unwanted or unintended mechanistic pathways. ROS begins to accumulate after mechanical impact and are known to drive chondrocyte cells into an enhanced metabolic state. With chondrocytes already synthesizing procatabolic and proinflammatory products, the enhanced metabolic activity leads to further cartilage degradation. ROS has been shown to enhance activation of procatabolic pathways like nuclear factor-kB (NF-kB), and mitogen-activated protein kinases (MAPK) like extracellular signal-regulated kinase 1/2 (Erk 1/2), p38 cascade, and c-Jun N-terminal kinases (JNK). Specifically, the cascade of the NF-k6 signaling pathway leads to detrimental effects on the articular environment. This pathway leads to the secretion of MMP-1, -2, -3, -7, -8, -9, -13, and -14 and a disintegrin and metalloproteinase with thrombospondin motifs (ADAMTS)-1, -3, -4 and -5 which results in cartilage breakdown. Evidence of increased ROS production levels and mitochondrial dysfunction has been found in primary human chondrocyte cells stimulated with Il-1β (5 ng/ml) in culture. Similar results observing cell viability and ROS production in primary human chondrocyte cells cultured with Il-1β (10 ng/ml) have been reported.

Current treatments for PTOA are largely palliative and the advanced progression of PTOA can lead to joint replacement. Typically, a discrete joint trauma is a common impetus for PTOA with the younger population being more commonly affected by PTOA which may be due to the younger population having a more active lifestyle. Commonly after a joint trauma associated with PTOA, progression, disruption, and penetration of the glycan surface occurs exposing the underlying articular cartilage ECM. This ECM is mainly composed of type II collagen which provides a unique physical characteristic of PTOA damage that can be utilized in the challenge of mitigating PTOA's progressive destruction. By using type II collagen as a targeted binding site for a therapeutic, this can provide therapeutic delivery at the damaged site rather than in the intraarticular space.

The use of targeting type II collagen in subjects with PTOA trauma has historical standing. A non-invasive type II collagen antibody conjugated to nanoliposomes encapsulated with a fluorescent dye has been developed which was used as a diagnostic tool to determine the early stages of PTOA and cartilage injury. In a two-week study, an increase in osteoarthritic changes through histopathology was shown in a mechanical load PTOA mouse model which correlated with an increased fluorescence through imaging.

Curcumin is a naturally derived molecule from turmeric. It is well known for its anti-inflammatory and free radical scavenging abilities. It has also been investigated as a treatment for OA and PTOA. It is believed that curcumin can suppress the activator protein-1 and nuclear factor kappa B pathways which are known to stimulate the synthesis of a host of proinflammatory cytokines and interleukins, like Il-1β, known to lead to chondrocyte apoptosis and articular cartilage ECM degradation.

Research into the use of mesenchymal stem cells (MSCs) in the treatment of PTOA have also been investigated. MSCs can play an interesting role in the regeneration of damaged articular cartilage. It has been reported that the use of bioactive agents like hyaluronic acid, transforming growth factor-13 and insulin growth factor-1 all help to promote differentiation of MSCs down a chondrocytic lineage. By creating a collagenous transporter for MSCs loaded with bioactive agents to promote chondrocyte differentiation, this may create a structurally sound 3-dimensional scaffold with a proper microenvironment which can provide the cells with mechanical cues along with the cues from the bioactive agents for the development of similar tissue to native articular cartilage when implemented to the damaged site.

A type II collagen monoclonal antibody conjugated to collagen microparticles (CMs) immersed in curcumin was developed to specifically bind to exposed type II collagen that may arise from mechanical impacts or chemical reduction of the articular surface from PTOA events. The CMs provide an opportunity for the release of the bioactive agent, curcumin, into the damaged region to mitigate PTOA progression. Type II collagen antibody binding studies along with Il-1 stimulated human chondrocyte work was performed. Work with MSCs was also performed. MSC adherence to CMs was observed via light microscopy and live/dead cell staining was utilized to determine the viability of CMs to be utilized as a cellular transporter.

Materials and Methods

Fabrication of Liquid Collagen

Porcine collagen type I (10 mg/ml, Sunmax Biotechnology, Taiwan) was precipitated using 1.04 M sodium chloride (NaCl, 99.0%, Sigma Aldrich, MO). The precipitated collagen solution was then centrifuged at 3,500 rpm for 15 minutes. A white collagen pellet was formed at the bottom of the tube and the supernatant was poured off leaving a 150 mg collagen pellet. Fifteen ml of 0.5 M glacial acetic acid (99.7%, Fisher Chemical, KS) was added to the collagen pellet and allowed to sit overnight at room temperature to let the collagen pellet dissolve. The collagen/acetic acid solution was then placed in a 15 ml, 10 kDa molecular weight cutoff dialysis cassette (Thermo Scientific, IL) and immersed in an ethylenediaminetetraacetic acid (35 mM, EDTA, Fisher Chemical, KS)/$H_2O$ solution with a pH of 7.5 using sodium hydroxide (10 N, NaOH, Ricca Chemical Co., TX). The pH of the EDTA solution was checked and maintained at 7.5 daily until the pH no longer fluctuated from 7.5. The liquid collagen (LC) solution was then removed and pH was tested to ensure it was set at 7.5.

Collagen Microparticle Fabrication

Fifty ml of olive oil (Sigma Aldrich, MO) and 0.35% (v/v) sorbitan monooleate (Sigma Aldrich, MO) was added to a 100 ml round bottom flask. A 4 cm stir bar was added to the flask and placed on a stir/hot plate and set to 1150 rpm. The emulsion was allowed to equilibrate for 10 minutes. After 10 minutes, 1 ml of the LC solution was added dropwise using an 18-gauge plastic cannula. One hour after the LC addition, the stir plate temperature was set to 35° C. and allowed to stir for 1 hour. After the emulsion time was reached the collagen/oil solution was poured into a 50 ml centrifuge tube and centrifuged at 5000 rpm for 5 minutes. The oil was then removed and 25 ml 50% acetone (Fisher Chemical, KS) and 100 µl tween-20 (Sigma Aldrich, MO) was added to the tube to wash the collagen microparticles (CMs). The solution was vortexed for 1 minute and sonicated for 3 minutes. The solution was then centrifuged at 5,000 rpm for 5 minutes. The sample was washed 3 times using 50% acetone and tween-20 and then was washed 3 times using 1×PBS (Sigma Aldrich, MO). The CMs were stored in 15 ml 1×PBS and placed in a 4° C. refrigerator.

Anti-Collagen Type II Antibody Conjugation to Collagen Microparticles and Incubation with Curcumin Monoclonal mouse collagen type II antibody (CIIMAb, Invitrogen, Thermo Fisher Scientific, MA5-12789) was conjugated to fabricated CMs with genipin. To conjugate, approximately 100 CMs in 100 µl PBS was introduced to 16.7 µl 35 mM genipin and incubated for 2 hours. After 2 hours, 1.67 µl CIIMAb was added to the CM/genipin solution and allowed to incubate for 24 hours on a shaker table at 225 RPM. Samples were washed three times with PBS and stored at 4° C.

CMs with curcumin (Sigma Aldrich, MO) were incubated for 24 hours in the specified (w/v) curcumin solution. After 24 hours, curcumin incubated CMs were washed 3 times using cellularly relevant media.

Semi-Quantitative CIIMAb Conjugation Analysis

After CIIMAb-CM conjugation, anti-mouse IgG, superclonal recombinant secondary antibody, alexa fluor 488 (FSSAB, Invitrogen, Thermo Fisher, A28175) was used to provide information on the ability of genipin to conjugate CIIMAbs to CMs. Six µl FSSAb was added to 100 CIIMAb-CMs and incubated on a shaker table set to 225 RPM at room temperature for 1 hour. After 1 hour, samples were washed three times using PBS. A spectrofluorometer plate reader (Cytation 5, BioTek, VT) was used to read the fluorescent intensity of FSSAb-CIIMAb-CMs at 499 nm excitation and 520 nm emission.

Articular Cartilage Preparation

Articular cartilage was harvested from euthanized swine from the School of Medicine at the University of Missouri. The articular cartilage was removed from the end of the femoral surface and was punched using a 4 mm cylindrical tissue punch. To damage the surface of articular cartilage, the articular cartilage was exposed to 0.25% trypsin-EDTA for 1 hour at 37° C. The articular cartilage was then washed with PBS and subsequently blocked with 5% horse serum for 1 hour at 37° C. The 100 CIIMAb-CMs were incubated with 200 µl FITC (1 mg/ml) for 1 hour. After 1 hour, the samples were washed and rehydrated with PBS. Samples were then added onto the surface of the articular cartilage discs and incubated at 37° C. for 30 minutes. The articular cartilage discs were then washed three times with PBS and imaged using fluorescent microscopy using a Cytation 5 (BioTek, VT) Cell Imaging Multi-Mode Reader using a GFP filter.

Cell Culture

Human Chondrocyte Cells

Human chondrocyte cells (CHON-001, ATCC, VA) were used to assess cell viability and ROS production when incubated with CIIMAb-CMs. The cells were cultured at 37° C. and 5% $CO_2$ in Dulbecco's Modified Eagle's Medium (ATCC, 30-2002), 10% (v/v) heat-inactivated fetal bovine serum (Gibco, Thermo Fisher, A3840001), and 0.1 mg/ml geneticin (Gibco, Thermo Fisher, 10131035). Cells were passed at confluency and media was exchanges as needed. Studies with these cells were between cell passages 5 and 10.

Murine Mesenchymal Stem Cells

Murine mesenchymal stem cells (MSC, C57BL/6, Cyagen, CA) were used to determine the time course it would take for the cell to become adherent onto CMs. The cells were cultured at 37° C. and 5% $CO_2$ in Dulbecco's Modified Eagle's Medium (Gibco, Thermo Fisher), 10% fetal bovine serum (Sigma Aldrich, MO), and 1% penicillin-streptomycin (Invitrogen, Thermo Fisher). Cells were passed and provided with fresh media as required. MSCs used in this study were passage 6.

WST-1 Assay

A WST-1 cell proliferation assay (Roche, Sigma Aldrich, MO) was utilized to determine the activity of human chondrocytes with CIIMAb-CMs incubated with various concentrations of curcumin. Cells were plated at a concentration of $5\times10^3$ cells per well and allowed to become confluent in a Costar 96-well plate. After the cells were confluent they were stimulated with 10 ng/ml Il-1β for 24 hours prior to the addition of CMs to evoke a simulated osteoarthritic cellular response. The cellular activity was analyzed 24 hours after the addition of CMs to the cells. WST-1 reagent was added to each well and the plates were incubated at 37° C. for 4 hours. After 4 hours, the media was removed from each well and absorbance readings were taken at 450 nm, with a 600 nm filter, using a spectrofluorometer plate reader (Cytation 5, BioTek, VT).

ROS Assay

An OxiSelect ROS assay (Cell Biolabs, CA) was used to determine produced intracellular ROS. Again, $5\times10^3$ human chondrocyte cells per well were stimulated with 10 ng/ml Il-1β for 24 hours in a 96-well plate after confluency was reached. After 24-hours of Il-1β stimulation, each well was washed with DPBS, and then 1×2',7'-dichlorodihydrofluorescein diacetate (DCF-DA)/DMEM was added and incubated for 1-hour. After 1-hour, the DCF-DA/DMEM was removed and washed two times with DPBS. CIIMAb-CMs incubated in curcumin were then introduced to the plate for 24 hours. Cell lysis buffer was then added to each well and allowed to incubate for 5 minutes. Each well was then transferred to a new well plate and read using a Cytation 5 spectrofluorometer (BioTek, VT) at 480 nm excitation and 530 nm emission.

Cell Imaging and Live Dead Cell Staining

MSCs were added to a Costar 24-well low attachment well plate along with media incubated CMs. The MSC/CM incubation was imaged using an Olympus IX50 inverted light microscope (Olympus, PA) using CellSense software.

Live/dead cell staining was performed using 3 µM calcein AM and 5 µM propidium iodide. Both calcein AM and propidium iodide were added to each well and incubated for 10 minutes before imaging. Cell/CMs were imaged with fluorescent microscopy using a Cytation 5 (BioTek, VT) Cell Imaging Multi-Mode Reader using either GFP or Texas Red filters.

Results

Semi-Quantitative Data of CIIMAb Conjugation to CMs

Figure 14:
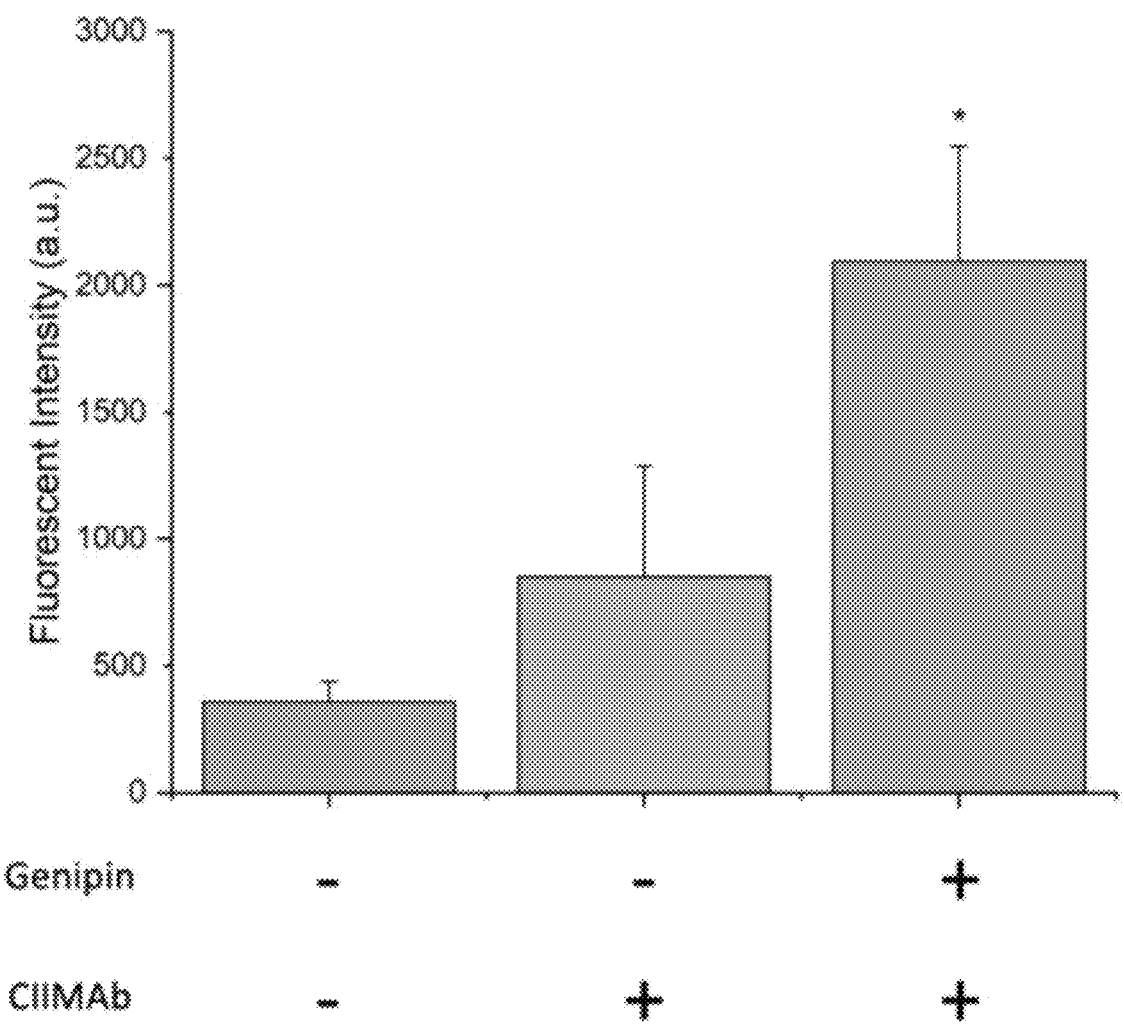
FIG. 14 depicts CIIMAb binding characterization through quantification of FSSAb attachment. Excitation at 499 nm and emission at 520 nm. n=6. * indicates P<0.01.

The use of FSSAb, a specific fluorescent secondary antibody to CIIMAb, was used to determine if the use of covalent crosslinker, genipin, provided an increased attachment of CIIMAbs to CMs over adsorption of CIIMAbs to CMs. Naturally, an increased fluorescent signal correlates to an increased concentration of CIIMAbs on the CMs. FIG. 14 provides evidence that the use of genipin to conjugate CIIMAbs to CMs does significantly outperform adsorption alone. A background signal was also determined to verify possible adhesion of FSSAb to CMs without the inclusion of either genipin or CIIMAbs.

Binding of CIIMAbs-CMs to Articular Cartilage

Figure 15:
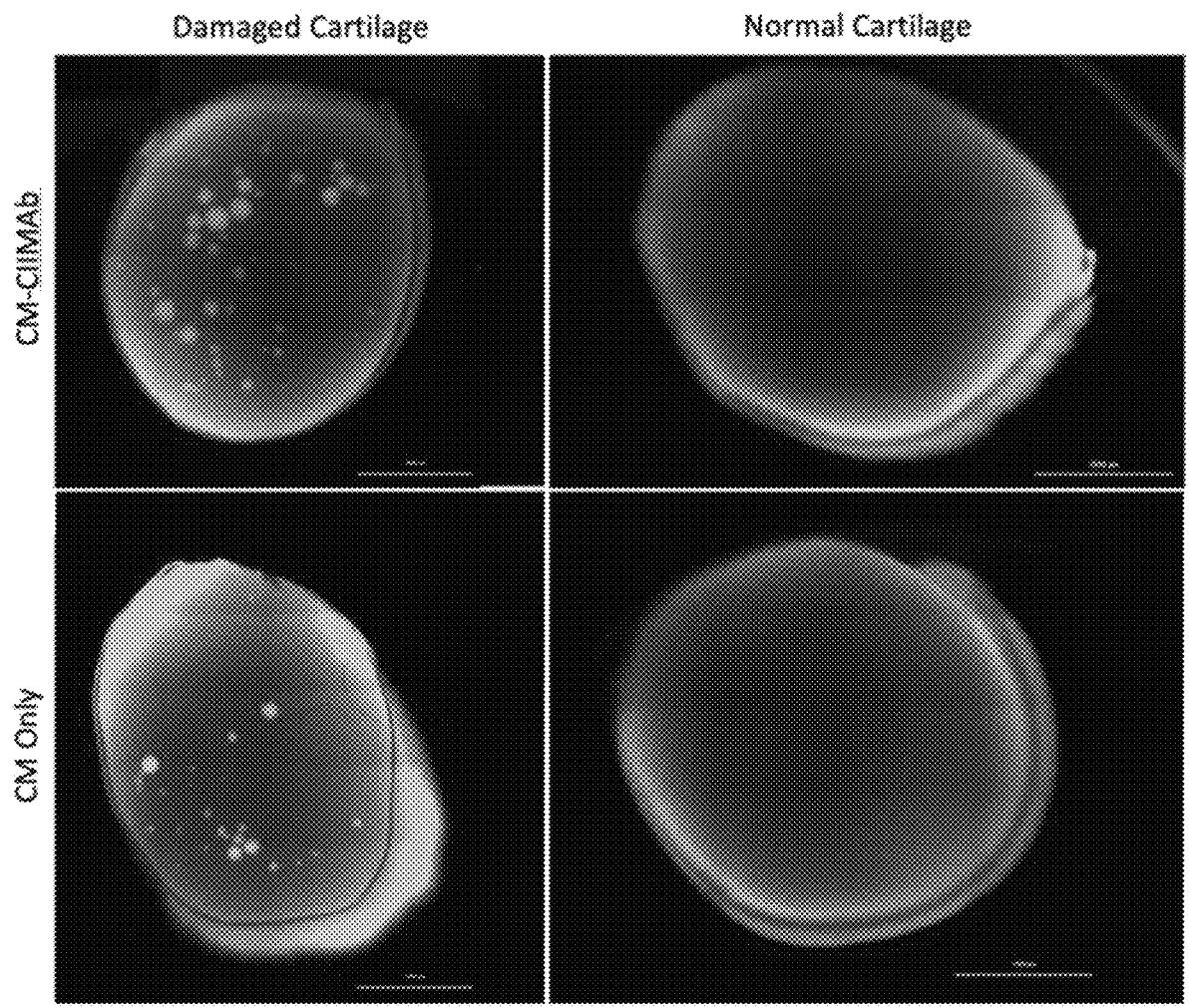
FIG. 15 depicts fluorescent micrographs of CIIMAb-CMs and CMs only exposed to both damaged and normal cartilage. Scale bar=0.1 cm.

Proteolytic digestion of the glycan surface on the articular cartilage was used to simulate articular damage and expose underlying type II collagen. This was performed to determine if CIIMAb-CMs can in fact bind to exposed type II collagen. FIG. 15 shows qualitative images of CIIMAb-CMs and CMs only exposed to both damaged and normal porcine cartilage. It is visually apparent that neither CIIMAb-CMs nor CMs only bound to the surface of normal cartilage. While both the CIIMAb-CMs and CMs only both bound to the surface of the damaged cartilage. It does appear however that the CIIMAb-CMs had more bound to the surface of the damaged cartilage relative to CMs only.

Cell Proliferation Assay

Figure 16:
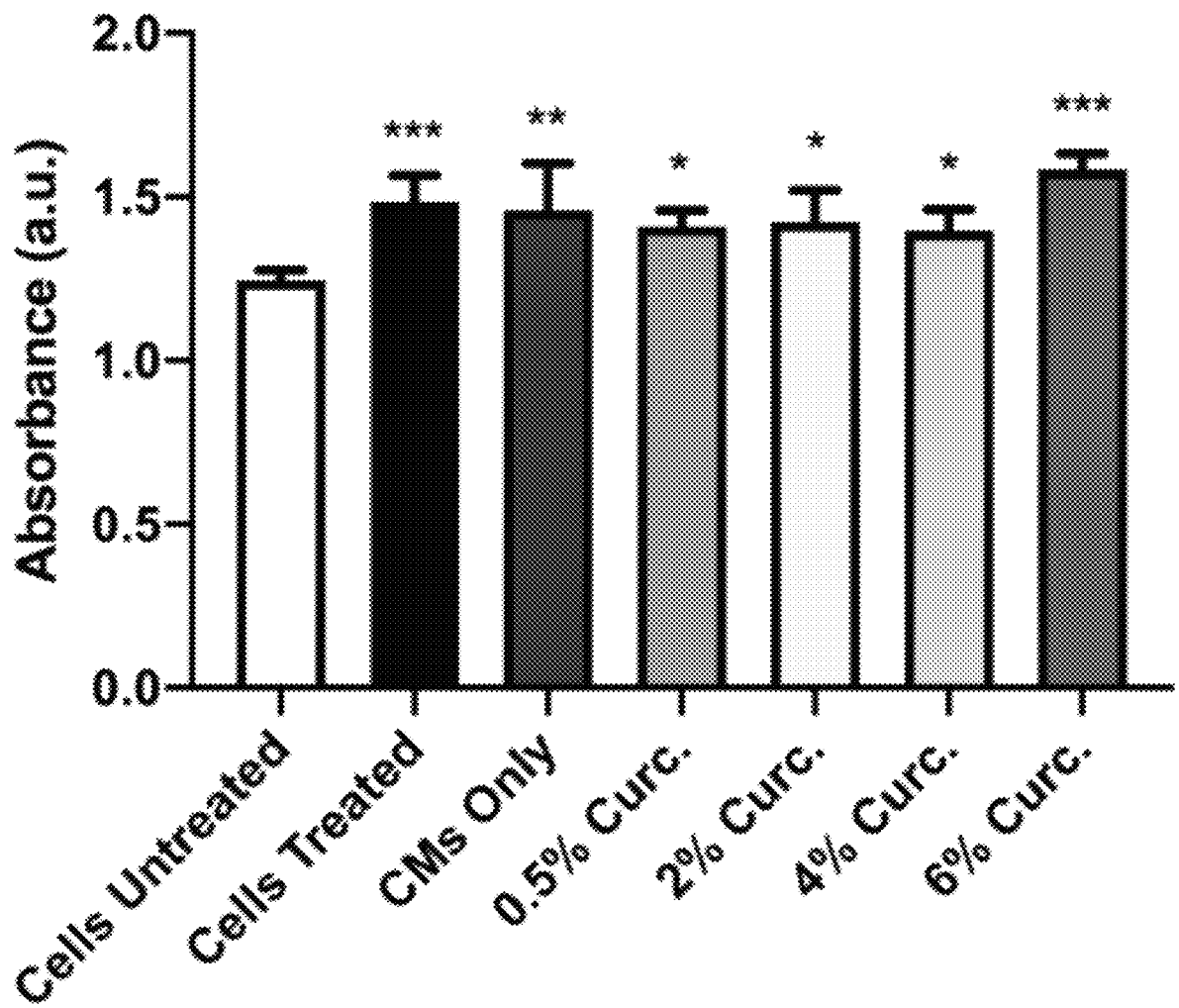
FIG. 16 depicts a 24-hour WST-1 assay with Il-1β stimulated human chondrocyte cells. n=6. * indicates=P<0.05;  indicates P<0.01; * indicates P<0.001.

A WST-1 cell proliferation assay, which measures cellular metabolic activity, was utilized to determine how Il-1β stimulated chondrocyte cells interact with CIIMAb-CMs supplemented with various concentrations of curcumin for a 24-hour incubation period. The Il-1β stimulated chondrocyte cells were utilized in order to simulate osteoarthritic activity. In FIG. 16, all groups treated with Il-1β had an increased cellular activity relative to the untreated cells. The only group to have a higher average cell activity than the treated cells group was the CIIMAb-CMs group treated with 6% (w/v) curcumin.

ROS Assay

Figure 17:
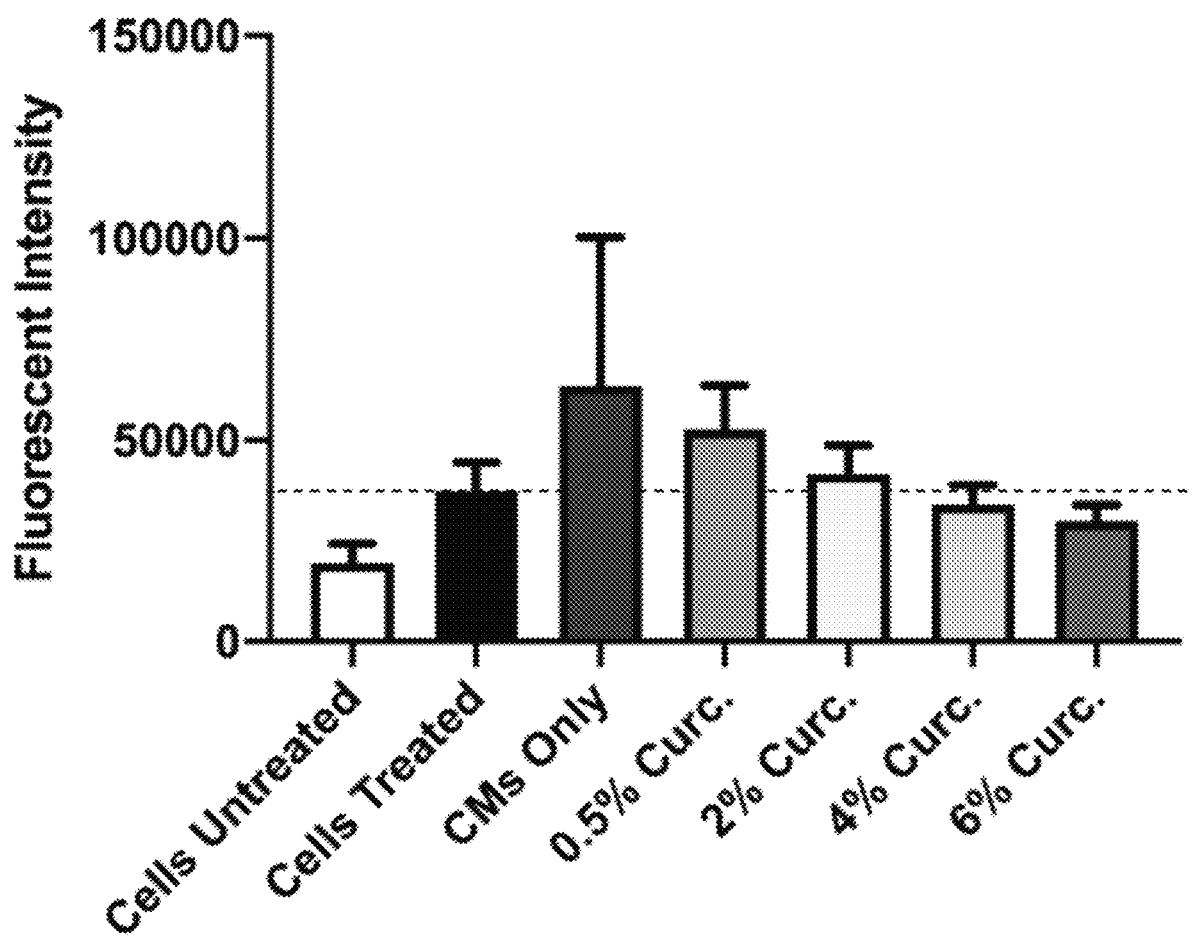
FIG. 17 depicts a 24-hour OxiSelect Intracellular ROS assay with Il-1β stimulated human chondrocyte cells. n=6.

An OxiSelectROS assay was used to determine the intracellular ROS production of Il-1β stimulated human chondrocyte cells after 24-hours of incubation with CIIMAb3M supplemented with various concentrations of curcumin in FIG. 17 After the 24 than the untreated cells. Interestingly the 4% and 6% (w/v) curcumin group had a lower average ROS production relative to the treated cells.

Imaging of MSC CMs

Figure 18A:
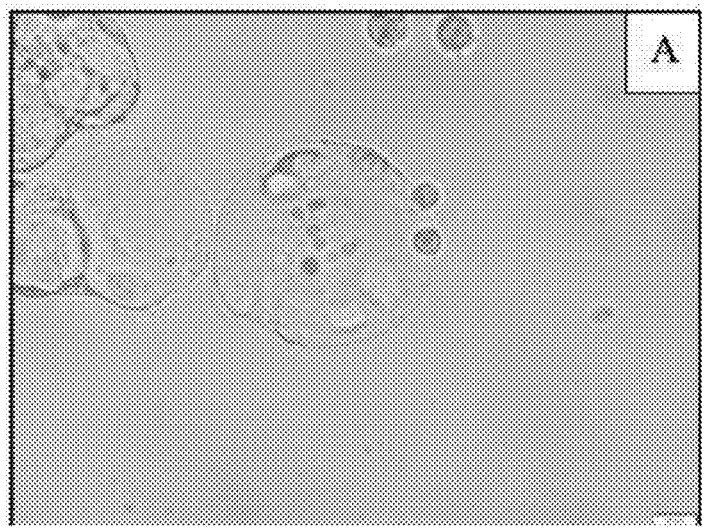
FIG. 18A is a light micrograph of CMs incubated with MSC on a low attachment well plate for 5 hours at 40× magnification.
Figure 18B:
FIG. 18B is a light micrograph of CMs incubated with MSC on a low attachment well plate for 24 hours at 40× magnification.
Figure 18C:
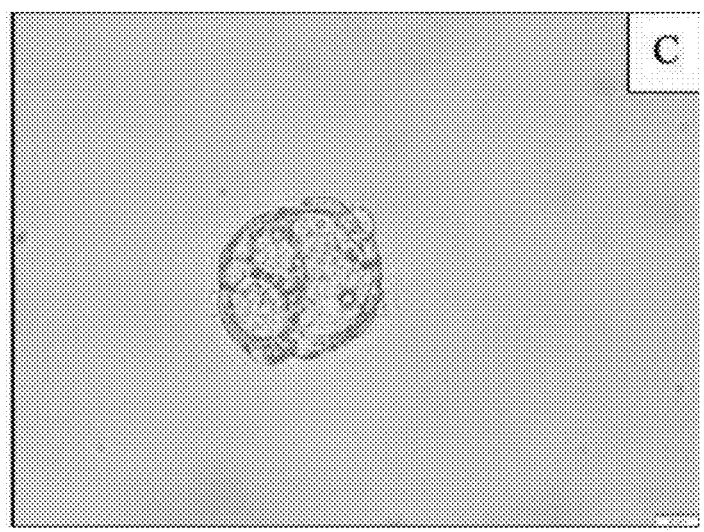
FIG. 18C is a light micrograph of CMs incubated with MSC on a low attachment well plate for 48 hours at 40× magnification.
Figure 18D:
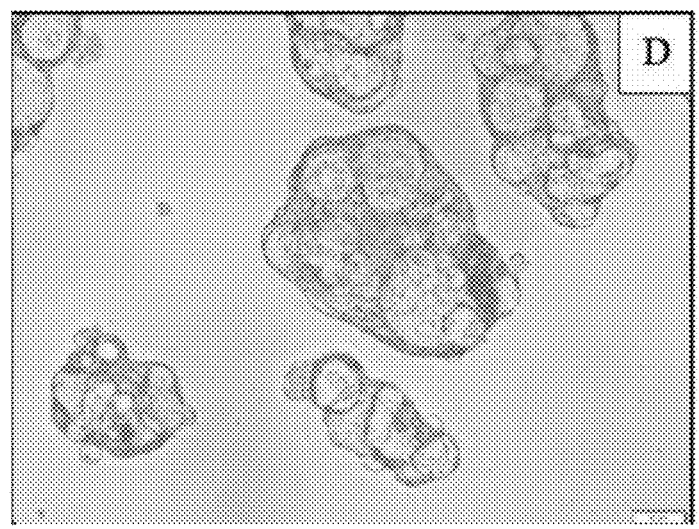
FIG. 18D is a light micrograph of CMs incubated with MSC on a low attachment well plate for 72 hours at 10× magnification.
Figure 18E:
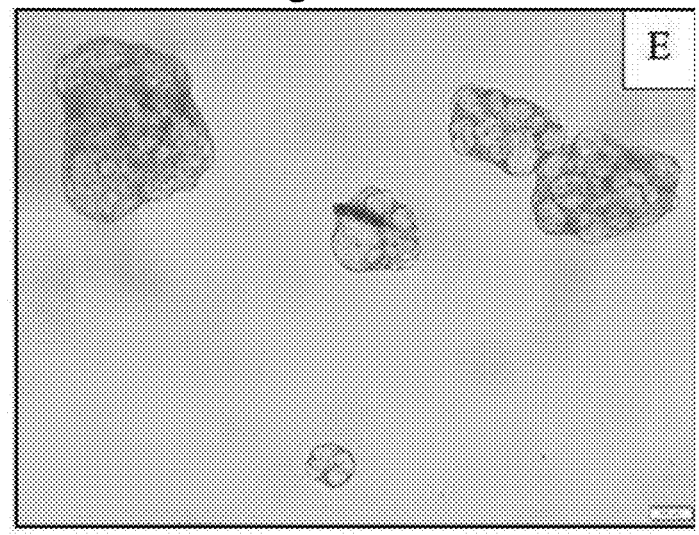
FIG. 18E is a light micrograph of CMs incubated with MSC on a low attachment well plate for 1 week at 4× magnification.
Figure 18F:
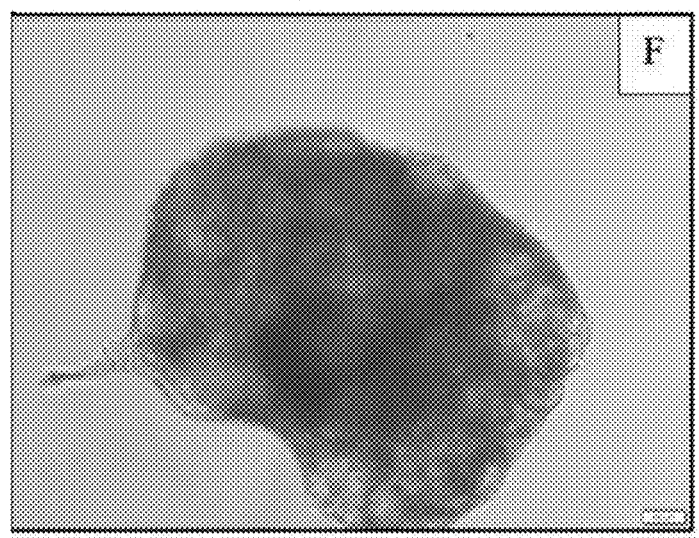
FIG. 18F is a light micrograph of CMs incubated with MSC on a low attachment well plate for 2 weeks at 4× magnification.

Imaging over 2 weeks was performed to observe the interaction between CMs and MSCs as shown in FIG. 18A-18F. At 24 hours of incubation, MSCs are attaching to the CMs (FIG. 18B). At 48 hours the MSCs appear to be completely covering the CMs surface (FIG. 18C). At 72 hours the MSC covered CMs appeared to aggregate into large clusters of MSC-CMs (FIG. 18D). Growth can continue to be observed at 1 week (FIG. 18E) of culture as the MSC-CM clusters continue to grow. At 2 weeks (FIG. 18F), MSC CMs became large enough that light had difficulty passing through the whole MSC CM cluster.

Figure 19:
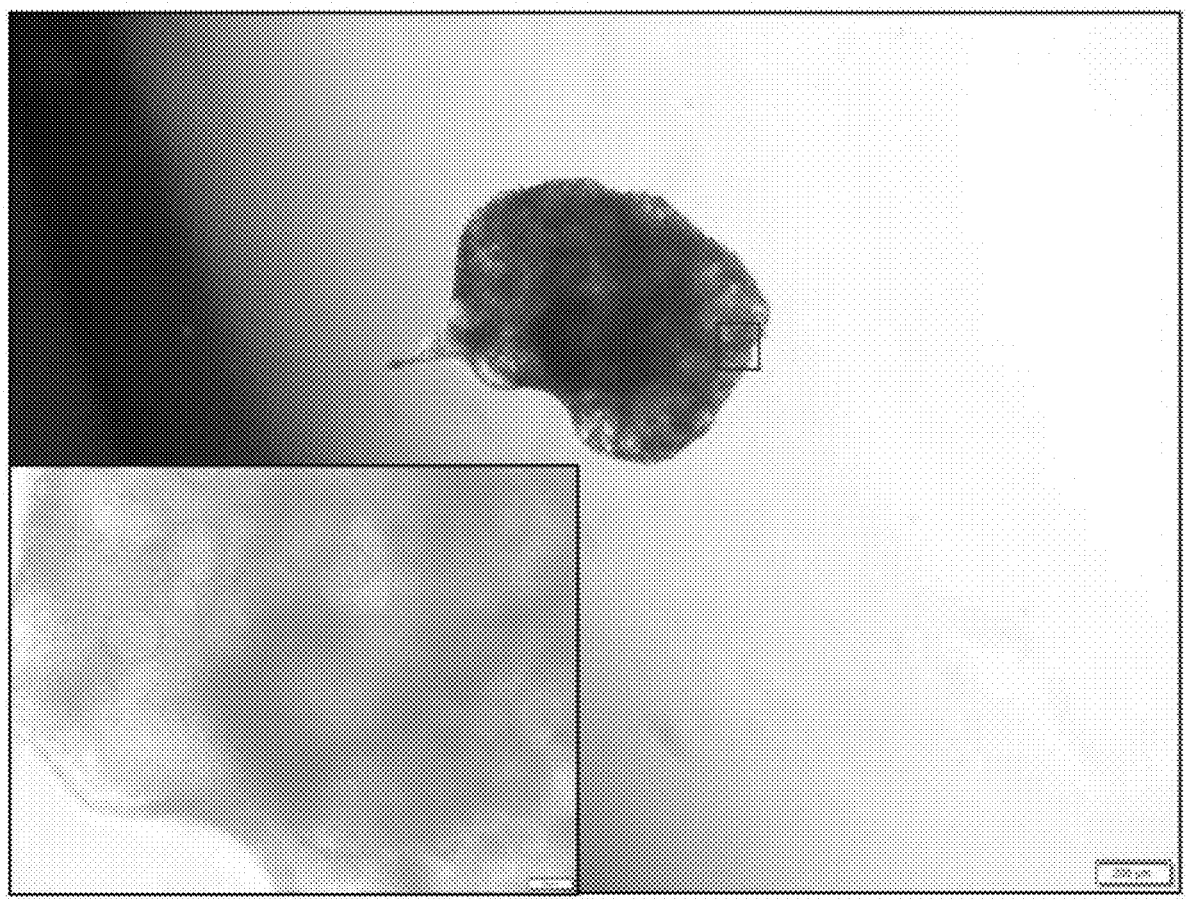
FIG. 19 is a light micrograph of a MSC-CM cluster at 2-weeks. The box indicates the region imaged for the inlay. Inlay=20×.
Figure 20A:
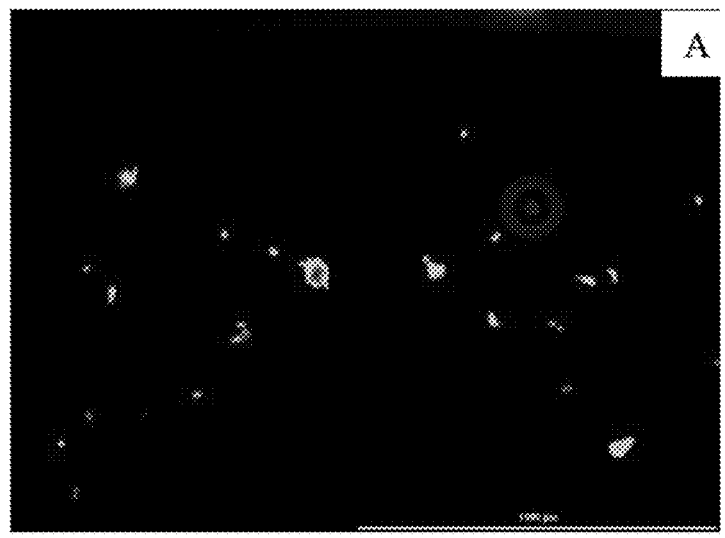
FIG. 20A is a fluorescent micrograph of live/dead cell staining of MSC-CM clusters at 24 hours with calcein AM and propidium iodide. GFP and Texas Red filters were used.
Figure 20B:
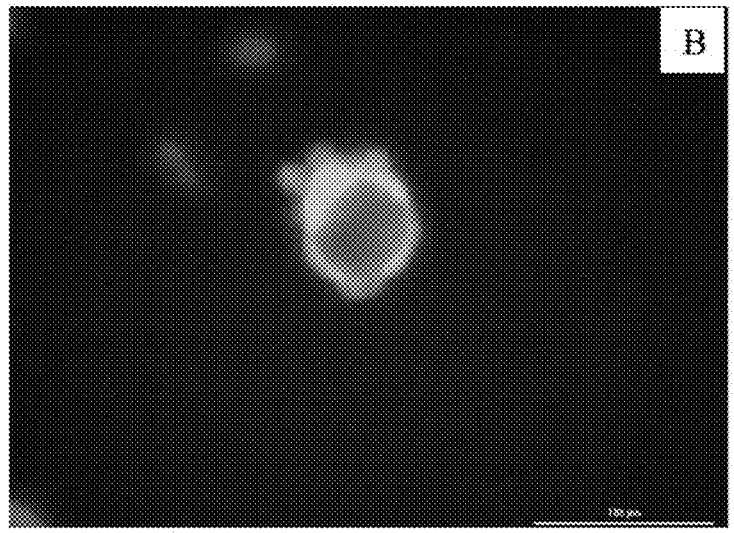
FIG. 20B is a magnified fluorescent micrograph of live/dead cell staining of a MSC-CM cluster at 24 hours with calcein AM and propidium iodide. GFP and Texas Red filters were used.
Figure 20C:
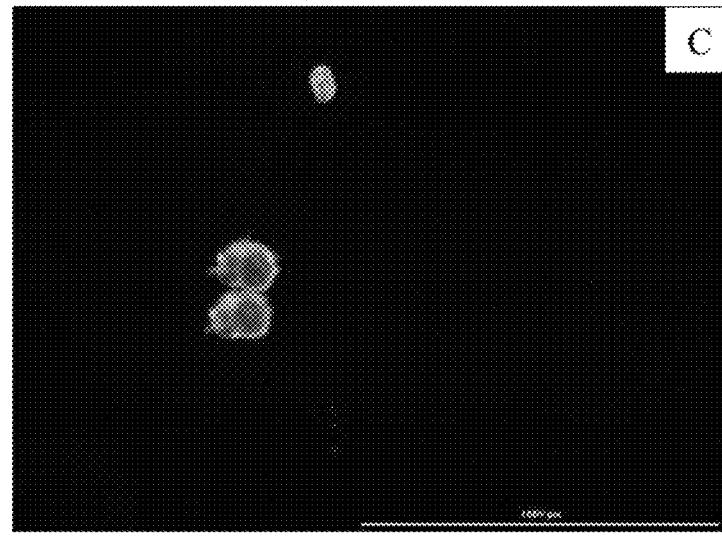
FIG. 20C is a fluorescent micrograph of live/dead cell staining of MSC-CM clusters at 48 hours with calcein AM and propidium iodide. GFP and Texas Red filters were used.
Figure 20D:
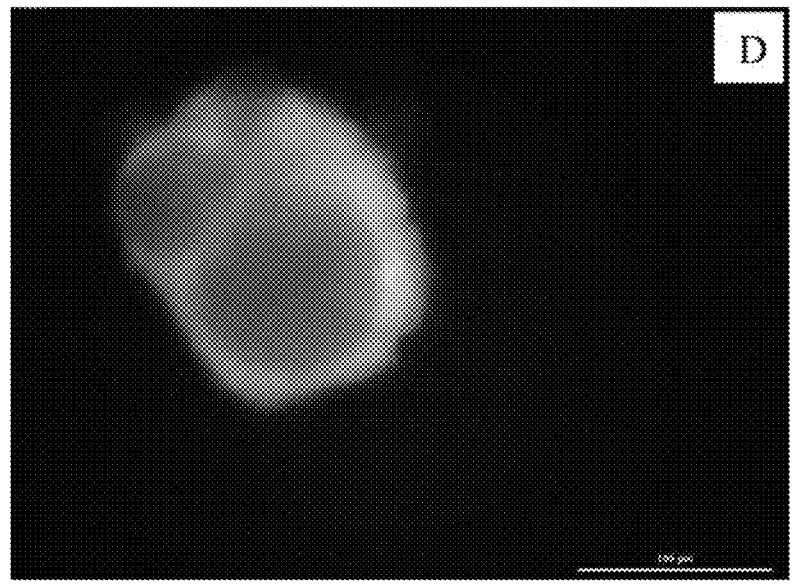
FIG. 20D is a magnified fluorescent micrograph of live/dead cell staining of a MSC-CM cluster at 48 hours with calcein AM and propidium iodide. GFP and Texas Red filters were used.
Figure 20E:
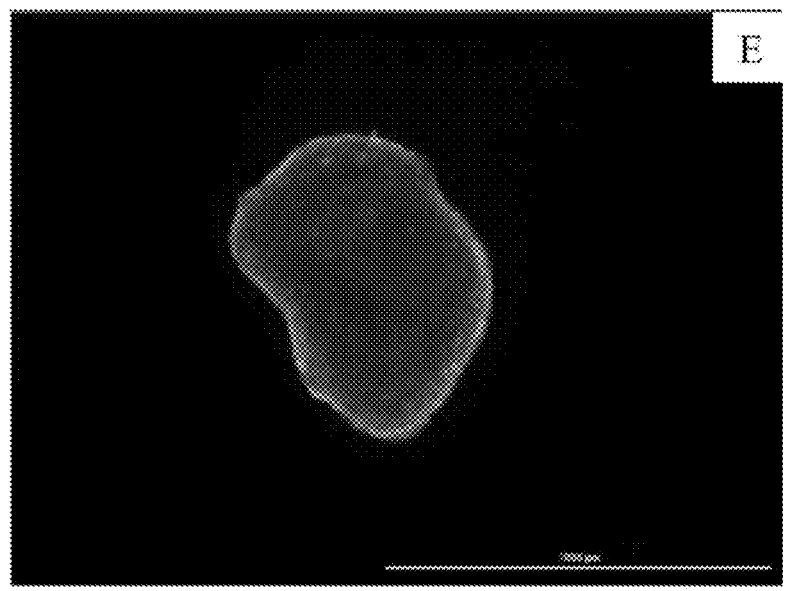
FIG. 20E is a magnified fluorescent micrograph of live/dead cell staining of a MSC-CM cluster at 2 weeks with calcein AM and propidium iodide. GFP and Texas Red filters were used.

The FIG. 19 inlay provides a 20× image giving better resolve to the CMs that are entrapped within the cluster at 2-weeks. FIG. 20A-20E displays live/dead cell staining images of MSC-CMs. At 24 hours in FIGS. 20A and 20B, low clustering was observed with viable cells seen on the surface. At 48 hours, in FIGS. 20C and 20D, clustering of CMs with MSCs were beginning to form. Some fluorescence in the red channel can also be seen which appears to be mostly in the CMs and does not appear to correlate to dead cells. In FIG. 20E, the cluster is largely living cells; it appears that the center may have some cellular remnants or most likely as shown in FIG. 20E, some of the propidium iodide was able to infiltrate the CMs giving rise to the color in the red channel.

Discussion

Previous work focused on the development of CMs for general injectable musculoskeletal applications. An antibody-based CM scaffold to target damaged cartilage was developed. The CMs may have the potential to mitigate detrimental effects that can arise in dysregulated catabolic chondrocyte cells exposed to a PTOA environment.

By conjugating the CIIMAbs to CMs using a covalent crosslinker, genipin, there was a higher overall attachment to the CMs in comparison to adsorption of the CIIMAbs to the CMs.

The glycan surface of the articular cartilage becomes disrupted as events like PTOA occur leaving exposure of the underlying articular cartilage ECM components like type II collagen and can even expose and penetrate through to the mineralized bone region. In a simulated osteoarthritic cartilage model both the CIIMAb-CMs and CMs only were able to bind to the surface of the damaged cartilage, albeit CIIMAb-CMs appeared to bind at a higher percentage. Neither the CIIMAb-CMs nor the CMs only were able to bind to normal undamaged cartilage. Taking the work from Cho et al. which transitioned their antibody conjugated liposomes from an explanted trypsin in vitro cartilage lesion model to an in vivo mouse model with translational results, this provides a sound basis for the ability of CIIMAb-CMs to target and deliver therapeutic bioactive agents to damaged regions of articular cartilage. Another observable advantage of binding CIIMAB-CMs to damaged regions of articular cartilage is their ability to create a physical barrier between the exposed damaged tissue and the articulating surface by binding to the exposed damaged tissue. This creates a potential protective layer and prevents further articulating mechanical damage at the already damaged site.

Il-1β is a commonly overexpressed proinflammatory cytokine in damaged cartilage which has profound effects on chondrocytes and the surrounding ECM and is thought to be one of two main driving cytokines in disease progression. Exposing Il-1β to chondrocyte cells in monolayer culture can simulate the catabolic response seen in PTOA impacts like an increased expression of catabolic cytokines and ROS production which are two major factors that progressively degrade articular cartilage ECM and lead to chondrocyte cell death.

ROS has been linked to significant cartilage degradation through increased activation of known catabolic pathways nuclear factor-kB and several mitogen-activated protein kinase pathways. Accumulation of ROS has been shown to enhance chondrocyte metabolic activity after injury and also contribute to cell death.

Observing Il-1β stimulated human chondrocyte cells metabolic activity, an increase in metabolic activity with all CIIMAb-CM groups was seen along with the positive control relative to the untreated cells 24-hours after exposure to Il-1β. This was not necessarily unexpected as increased metabolic activity shortly after exposure is a hallmark of damaging the environment. To further assess the curcumin loaded CIIMAb-CMs, an assay to study intracellular ROS production 24 hours after exposure to Il-1β was conducted to determine if the curcumin was playing a role in limiting ROS production.

While examining ROS production, the CIIMAb-CM group supplemented with 4% and 6% curcumin reduced intracellular ROS relative to the positive control group. While taking both the cellular metabolic activity and ROS data into correlation with the CIIMAb-CMs supplemented with 4% and 6% curcumin, chondrocyte cells were observed that have an enhanced metabolic activity relative to untreated cells while having a lower overall intracellular ROS production relative to treated cells which lends evidence to the chondrocyte cells having a reduced catabolic response when coming into contact with CIIMAb-CMs supplemented with 4% and 6% curcumin.

Working with MSCs and CMs, the MSCs appeared to preferentially adhere to the surface of the CMs at about 24 hours of incubation. The MSCs appear to completely cover most CMs at 48 hours. They also began to aggregate with each other and also aggregate into MSC-CM clusters. At 48 hours and also at 2-weeks, live/dead cell staining provided evidence of a largely living cluster of cells with some possible cellular remnants in the center of the cluster. The dead cells may have been due in part to poor diffusion of cellular media into the core of the cluster. Without being limited by theory, another possibility could be the porous structure of the CMs allowed the infiltration of propidium iodide and had some adsorption to the CMs. It does appear the stain in the red channel clustered in and around the CMs. Between 24 to 48 hours CMs appear to be viable transporters of MSCs to damaged cartilage without forming large clusters. These MSC-CMs may be a suitable injectable which targets articular cartilage regeneration. Supplementation of the CMs with bioactive agents like hyaluronic acid, transforming growth factor-13 and insulin growth factor-1, which help to progress differentiation of MSCs down a chondrogenic lineage would be advantageous. With the MSC-CMs able to cluster, this may allow for clusters to form on damaged regions of cartilage which may have the capacity to fill articular defects after MSC-CMs are introduced into the articular environment.

In summary, the ability of CMs to be labeled with collagen type II targeting antibodies was demonstrated. The CIIMAb-CMs preferentially bound to the damage induced cartilage. The addition of curcumin appeared to reduce ROS production and increase cellular metabolic activity. MSCs preferential adhered to CMs and grew large cellularly viable clusters over 2-weeks of incubation. CIIMAb-CMs can be used for targeting damaged cartilage and delivering therapeutic agents at the damaged site, and MSC-CM clusters can be used for regeneration of tissue.

Example 4: Fabrication of 3D Printed Scaffolds Using Crosslinker-Free Collagen Solution Introduction Collagen is one of the most abundant protein in the body. This protein provides structural scaffold support for soft tissues such as the dermis, ligaments, and tendons to mechanical protection in articular cartilage. There are 29 different forms of collagen identified. Type I collagen is the most commonly found collagen in the human body at about 80%. It possesses a triple helix structure composed of three polypeptide chains with a glycine-X-Y repeating sequence with X and Y commonly being proline and hydroxyproline respectively.

Type I collagen is a highly biocompatible material with low immunogenicity. It can easily degrade and remodel naturally by the body's cells over time, which positions it as an excellent candidate for therapeutic applications and tissue engineering applications. Collagen can be derived from various sources including animals such as porcine and bovine. Acquiring type I collagen from a source requires a process of solubilizing various tissue elements until a purified collagen structure can thus be solubilized.

Solubilized collagen can be formulated into many types of structures. A relatively young technique utilizing solubilized collagen is extrusion-based bioprinting. With this method, collagen can remain in a liquid state, depending on the solutions pH and temperature. The liquid collagen can be bioprinted into solutions with adjusted pH or increased temperatures, which initiates collagen fibrilization forming a solid structure. Research on bioprinting of type I collagen has been focused on hard tissue applications. The optimization of a type I collagen laden osteoblast-like cell and human adipose-derived stem cell bioink has been reported, comparing a collagen-based bioink to an alginate bioink. The collagen-based bioink improved cellular activity and also improved relative concentrations of osteogenic biomarkers like BMP-2, Runx2, type I collagen, and OCN at 28 days with human adipose-derived stem cells. Another study printed an MRI scanned human meniscus tissue using extrusion-based 3D printing with a type I collagen and bone-marrow-derived mesenchymal stem cells. Using additive manufacturing methods like extrusion-based bioprinting of collagen creates unique fabrication capabilities for patient-specific treatments.

Chemical crosslinking is a common technique used to conjugate additional agents, such as gold nanoparticles (AuNPs) to collagen tissue scaffolds. Common crosslinkers include genipin and 1-Ethyl-3-[3-dimethylaminopropyl]carbodiimide hydrochloride)/N-hydroxysuccinimide (EDC/NHS) crosslinking. EDC/NHS crosslinking involves the formation of a peptide bond between carboxyl and amino groups. EDC/NHS crosslinking is a zero-length crosslinker, meaning the actual EDC molecule is not a part of the final crosslinked product. But the EDC/NHS crosslinking reaction creates unwanted urea byproducts that can cause cytotoxicity if not removed. This then requires laborious washing techniques which can cost time and may damage the tissue/collagen scaffolds. EDC/NHS crosslinking has also been shown to affect native-like cellular adhesion. An alternative crosslinker is genipin. Genipin is a natural crosslinker isolated from *Gardenia jasminoides* fruits. Genipin can spontaneously react with two amino groups that form monomer to tetramer crosslinks. The use of genipin has also been studied as an anti-inflammatory agent. With this in mind, genipin is advantageous because it does not necessitate extensive washing steps to remove extraneous unwanted byproducts after the crosslinking process. The lack of washing could improve the overall healing time with the observed anti-inflammatory properties of genipin.

Gold nanoparticles (AuNPs) have had much interest in tissue engineering applications in recent years. This may be due to AuNPs multiple studied benefits such as mitigation of inflammation, promotion of cellular migration, and high biocompatibility. Attachment of AuNPs to scaffolds may increase the surface energy of the scaffold which can in turn increase cellular adherence through adsorption of proteins. AuNPs have also been documented to be an effective antimicrobial agent along with being an effective free radical scavenger which inhibits the formation of reactive oxygen species (ROS). The production of ROS is known to be detrimental to tissues during wound healing. By utilizing AuNPs on musculoskeletal tissue scaffolds, this may allow for quicker healing time through increased cellular migration, remodeling and reduction of surrounding ROS.

This example describes the method of fabrication of porcine type I collagen scaffolds for general musculoskeletal tissue applications via additive manufacturing, 3D printing, with two different bioprinters. Further characterization of the 3D printed collagen scaffolds includes the use of two different chemical crosslinkers, EDC/NHS and genipin. An analysis of thermal stability, ability to conjugate AuNPs, and cellular interactions on the composite 3D printed collagen scaffolds was performed.

Materials and Methods

Bioprinter

Figure 21:
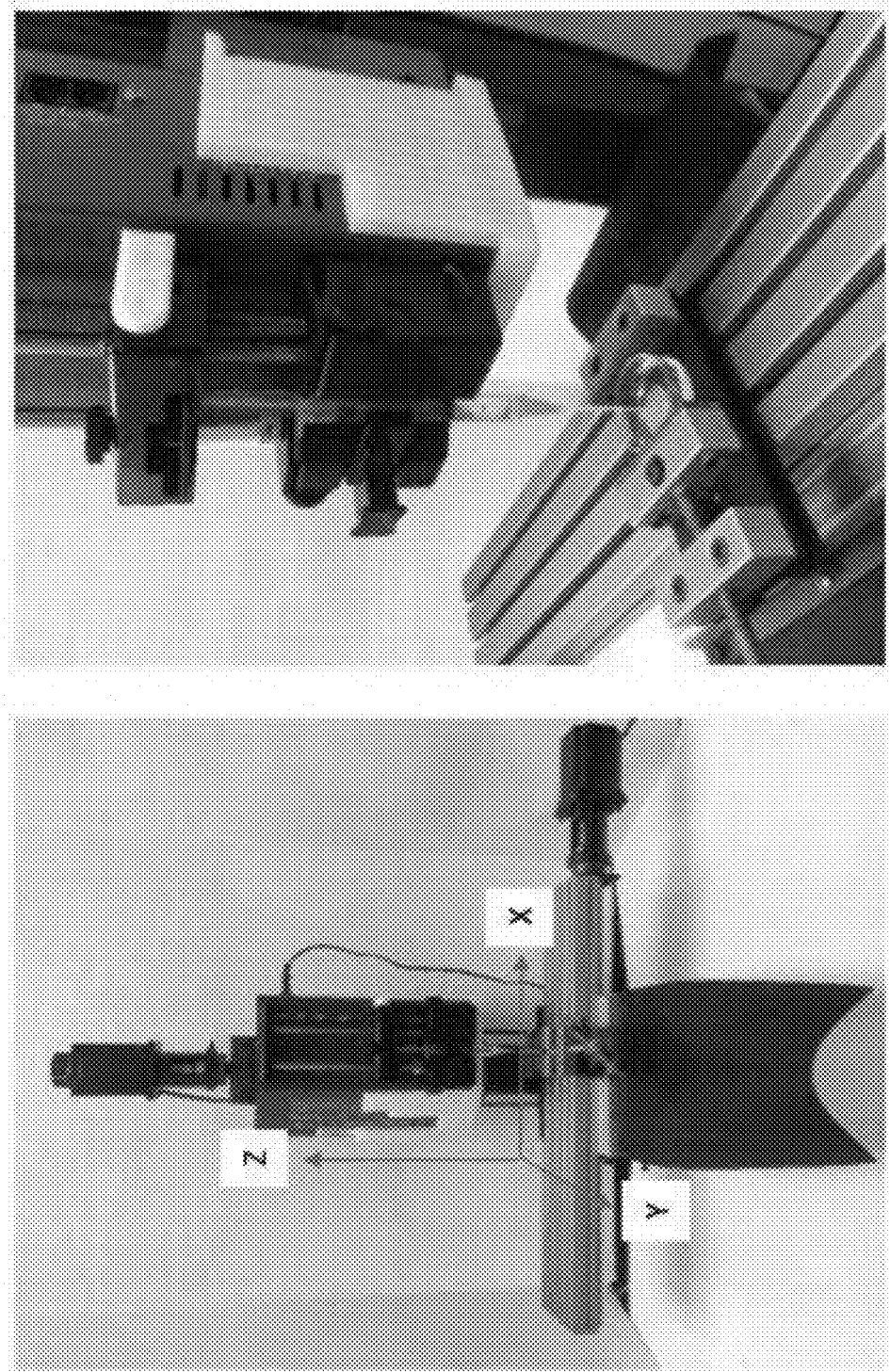
FIG. 21 shows a custom 3D printer from CNC milling machine. X, Y, and Z axes are denoted on the printer (left). (Right) shows the 3D printer printing a collagen scaffold.
Figure 22C:
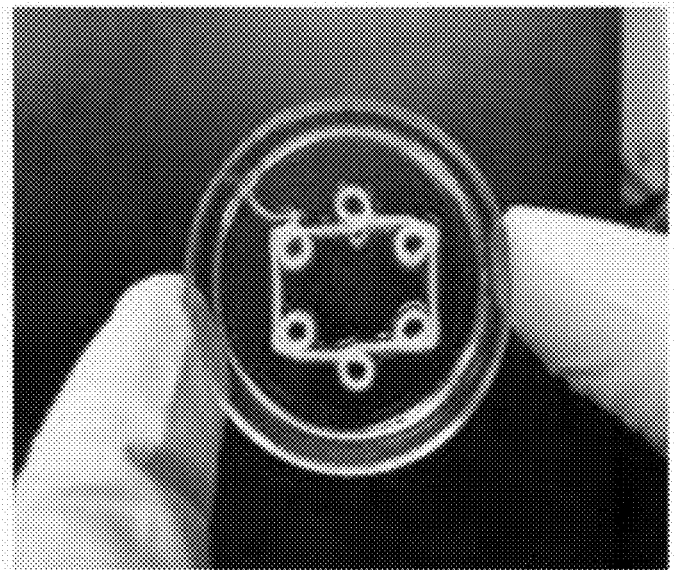
FIG. 22C shows 4 mm×2.4 mm 3D printed cylinder scaffolds printed from the custom 3D printer used for experimentation.
Figure 22B:
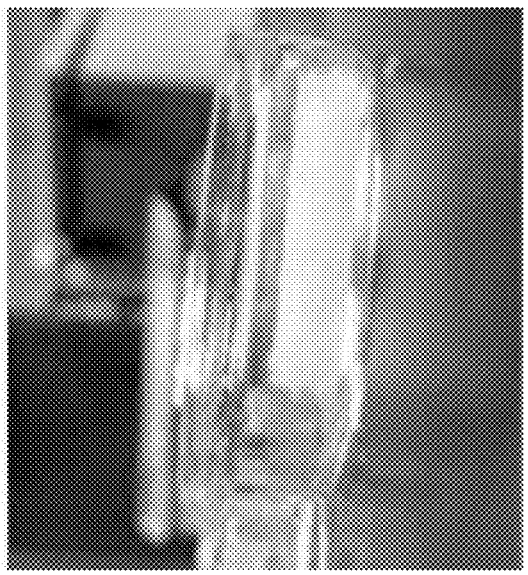
FIG. 22B shows a side view of a 20 mm×6.3 mm 3D printed collagen cylinder scaffold printed from the custom 3D printer.
Figure 22A:
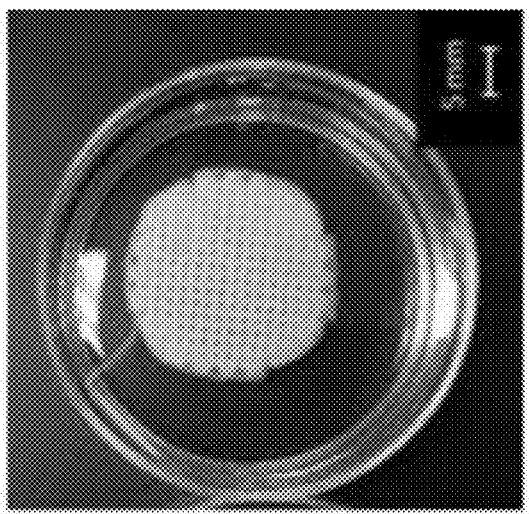
FIG. 22A shows a top view of a 20 mm×6.3 mm 3D printed collagen cylinder scaffold printed from the custom 3D printer.

One of the bioprinters used to fabricate the 3D scaffolds was a custom bioprinter assembled from a CNC milling machine as shown in FIG. 21. Three stepper motors were used to individually control each axis; X, Y, and Z. The motors had an error of movement less than 0.1 µm. The print bed was created by placing the X stage and Y stage on top of one another. The Z stage was placed in a perpendicular orientation to the print bed. To control the motor's movements, G-code was written and executed using Mach3 Mill software. A syringe pump was mounted on the Z stage which held and extruded the printing solution (liquid collagen). FIG. 22A-22C are images of scaffolds printed from the custom CNC milling machine. FIGS. 22A and B are images of a 20 mm×6.3 mm cylinder. Studies performed in this work were 4 mm×2.4 mm scaffolds printed in FIG. 22C.

Figure 23:
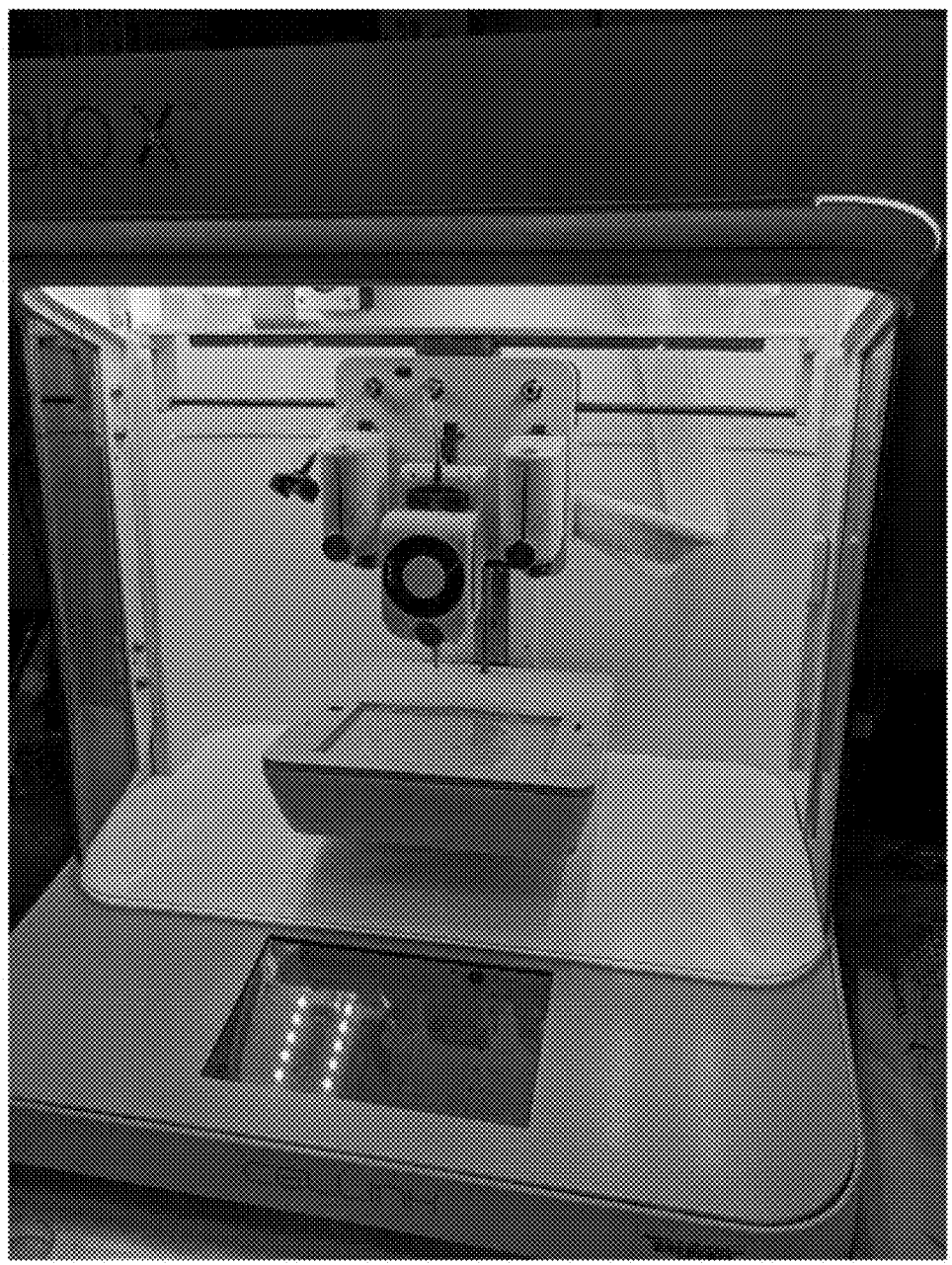
FIG. 23 shows a Cellink BioX printer with temperature controlled printed head.

A Cellink Bio X (Boston, MA) 3D bioprinter using a temperature-controlled pneumatic printhead (4-65° C.) was also used to print, as shown in FIG. 23. A 3 ml Cellink pneumatic printing cartridge was filled with the printing solution (liquid collagen) disclosed herein and a 27-gauge conical nozzle was utilized during printing. The temperature-controlled pneumatic printhead was set to 4° C. The printing solution was printed into a 150 mm diameter polystyrene Petri dish filled with 15 ml of 24° C. ddH$_2$O. The print height was set to 0.2 mm with a printing speed of 3 mm/s and nozzle pressure was set to 10 kPa for all prints. Post printing, scaffolds were allowed to fibrillize for 5 minutes and then lifted out of the Petri dish and placed in 70% ethanol for storage. 3D models were designed using Solidworks and sliced with Cellink's built-in slicing software or Slic3r software. FIG. 24 is a computer-generated diagram of the printed scaffold layer by layer. For cell studies, a 6 mm×0.8 mm (4 layers) cylinder scaffold with a 20% rectilinear infill pattern was designed as shown in FIG. 25A. FIG. 25B is a scaffold printed in an agarose microparticle solution.

Fabrication of Liquid Collagen

Porcine collagen type I (6 mg/ml, Sunmax Biotechnology, Taiwan) was precipitated using 1.04 M sodium chloride (NaCl, 99.0%, Sigma Aldrich, MO). The precipitated collagen solution was then centrifuged at 3,500 rpm for 15 minutes. A white collagen pellet was formed at the bottom of the tube and the supernatant was poured off leaving a 150 mg collagen pellet. Fifteen ml of 0.5 M glacial acetic acid (99.7%, Fisher Chemical, KS) was added to the collagen pellet and allowed to sit overnight at room temperature to let the collagen pellet solubilize. The collagen/acetic acid solution was then placed in a 15 ml, 10 kDa molecular weight cutoff dialysis cassette (Thermo Scientific, IL) and immersed in ethylenediaminetetraacetic acid (35 mM, EDTA, Fisher Chemical, KS)/$H_2O$ solution with a pH of 7.5 using sodium hydroxide (10 N, NaOH, Ricca Chemical Co., TX). The pH of the EDTA solution was checked and maintained at 7.5 daily until the pH no longer fluctuated from 7.5. The liquid collagen (LC) solution was then removed and pH was tested to ensure it was set at 7.5.

Agarose Microparticle Printing Solution

The agarose microparticle printing solution was developed by Senior et al. To prepare the solution, a 0.5% (w/v) agarose solution was heated in an autoclave for 30 minutes at 225° F. After autoclaving, the heated solution was placed on a stir plate at 700 rpm until the solution reached room temperature.

EDC NHS Crosslinking

To crosslink the 3D printed scaffolds using EDC/N-hydroxysulfosuccinimide (NHS) crosslinking, printed scaffolds were placed in a flask at room temperature in a solution of 2 mM EDC (dissolved in 0.1 M 2-(N-morpholino) ethanesulfonic acid (MES) in 0.5 M sodium chloride (NaCl)) and 5 mM sulfo-NHS (first dissolved in dimethylformamide (DMF)) 50% acetone and phosphate-buffered saline (PBS; 7.5 pH). The flasks were placed on an orbital shaker at 75 rpm for 12 hours. Samples were subsequently washed three times with PBS.

Genipin Crosslinking

To crosslink the genipin crosslinked scaffolds, 2 mM genipin (initially dissolved in 18% (w/v) dimethylsulfoxide (DMSO)) solution was prepared using PBS. Samples were placed in a flask on an orbital shaker at 75 rpm and were incubated in the genipin solution for 12 hours. Samples were subsequently washed three times with PBS.

Conjugation of AuNPs

Twenty nm AuNPs were acquired from Ted Pella Inc. (Redding, CA). To conjugate AuNPs, AuNPs were functionalized using a 15 µM 2-mercaptoethylamine (MEA) solution and added to the printed scaffolds at the same time as the addition of EDC/NHS crosslinking solution or genipin crosslinking solution. A 1× concentration of AuNPs correlates to $7.0 \times 10^{11}$ AuNP/ml AuNPs and 2× concentrations correlates to a $14.0 \times 10^{11}$ AuNP/ml concentration of AuNPs. A 1× AuNP concentration was used unless otherwise stated.

Sterilization

Samples undergoing biological study were sterilized using an ethanol solution. Samples were placed in a 70% ethanol solution for 24 hours at room temperature. After 24 hours, samples were then placed in sterile cell media for 24 hours. Finally, samples were transferred to a sterile 48-well culture and immersed in fresh sterile cell media in preparation for biological culture.

Differential Scanning Calorimetry

A Q2000 Differential scanning calorimeter (DSC) (TA Instruments, New Castle, DE) was used to observe the denaturation temperatures of the 3D printed scaffolds. The 4 mm×2.4 mm cylinders, FIG. 22C, were printed, dissected and then placed in the bottom of aluminum sample pans (~5 mm in diameter). These pans were then hermetically sealed. The DSC heated from −5° C. to 120° C. with a temperature ramp rate of 3° C./minute with modulation every 80 seconds ±0.64° C. The denaturation temperatures were determined using Universal Analysis software.

Scanning Electron Microscopy

Scanning electron microscopy (SEM) was used to determine AuNP conjugation to 3D printed scaffolds. Images were acquired using a Quanta 600 FEG (FEI, Hillsboro, OR). Samples were in low vacuum. Magnification ranged from 75× to 20,000× and the electron beam was set to 10 kV.

Neutron Activation Analysis

Neutron activation analysis was utilized to quantify the gold nanoparticles bound to the scaffolds. NAA was conducted at the University of Missouri Research Reactor Center. Once printed, the collagen samples were lyophilized, weighed, and secured within high-density polyethylene vials where they remained during the analysis. Samples were irradiated for two minutes, then allowed to decay for one to seven hours. Gamma radiation was measured for ten minutes via a Canberra High Purity Germanium detector. The detector has a relative efficiency of 33.7% and a full width half maximum resolution of 1.73 keV at 1.33 MeV. A Canberra digital signal processor, Model 9660A, was used in tandem with the detector and a high voltage power supply. Analysis of the data was performed utilizing Canberra-VMS Genie 2000 software, and the quantities of gold were recorded in Microsoft Excel.

Cell Culture

All cell assays were conducted with L929 murine fibroblast cells acquired from ATCC Manassas, VA Cells were cultured at 37° C. and 5% $CO_2$. Cell media used for culture was Eagle's Minimum Essential Medium (EMEM) supplemented with 200 U/ml Penicillin streptomycin and 10% horse serum. Cell passage numbers in the assays were between two and twenty-eight times. Cells remained under sterile conditions using a biological safety cabinet.

Cell studies involving stromal cells were human, patient derived. Fitzgerald et al. described the protocol for isolation. A very similar protocol to remove and isolate the endometrial epithelial cells was used to isolate the stromal cells. Further processing to isolate the stromal cells included using a 10 µm filter strainer to isolate the stromal cells after 100 µm and 40 µm filters. The filtrate was pelleted by centrifugation at 232 RCF for 10 minutes and the stromal cell pellet resuspended in 5 ml DMEM/F12 (Gibco, #11320-033) supplemented with 1% antibiotic-antimycotic (Gibco, #15240-062) and 10% charcoal stripped fetal bovine serum (CSFBS) and then transferred to a T25 flask. To obtain a pure population of stromal cells, the cells were incubated for 15 minutes at 37° C., supernatant collected and then transferred to a second T25 flask. The stromal cells were then continuously cultured until needed for further experiments. The stromal cells were seeded onto the 3D printed scaffolds in 50 µl of $3 \times 10^4$ cells. Cells were allowed to adhere for 30 minutes and the then 700 µl of culture medium was added. Culture media was exchanged as needed.

Cell Viability Study

Cell viability reagent WST-1 (Sigma Aldrich, MO) was used to assess the biocompatibility of the 3D printed scaffolds with L929 murine fibroblast cells. The 3D printed scaffolds were incubated in fresh supplemented EMEM 24 hours prior to the addition of fibroblast cells in a 48-well plate. Cells were seeded onto scaffolds at a ratio of $3\times10^4$ cells per well. 250 µl of the supplemented media was replaced every 3 days during study. 50 µl of the WST-1 reagent was added to each well and allowed to incubate for 4 hours. After 4 hours, 125 µl from each well was plated into a new 48-well plate and absorbance reading were measured at 450 nm with a 600 nm filter using a spectrofluorometer.

Results

Printing Images

FIG. 22A-22C provides images of 3D printed collagen scaffolds using the LC solution on the custom CNC bioprinting machine. As shown in FIGS. 22A and 22B, a general 20 mm×6.3 mm cylinder was printed in order to determine if the LC was applicable for 3D printing. The images demonstrated that the LC is amendable to printing; this is the first report of 3D printing of this EDTA stabilized collagen. The 3D printed scaffolds observed in FIG. 22C was used in the characterization studies. Samples produced using the Cellink BioX printer can be seen in FIG. 25A-25B. The 3D printed scaffold in FIG. 25A was used in the cellular characterization studies. The 3D printed scaffold in FIG. 25B was printed using the support agarose solution which provides solid-like behavior under low shear but liquid-like behavior with applied stress. The support solution is also able to recover from the deformation quickly once the shear stress is removed. This allowed the collagen to be held in into position and supported by the agarose solution after being printed creating less printing defects and created a more reproducible scaffold.

LC Printing Diameter

Figure 26:
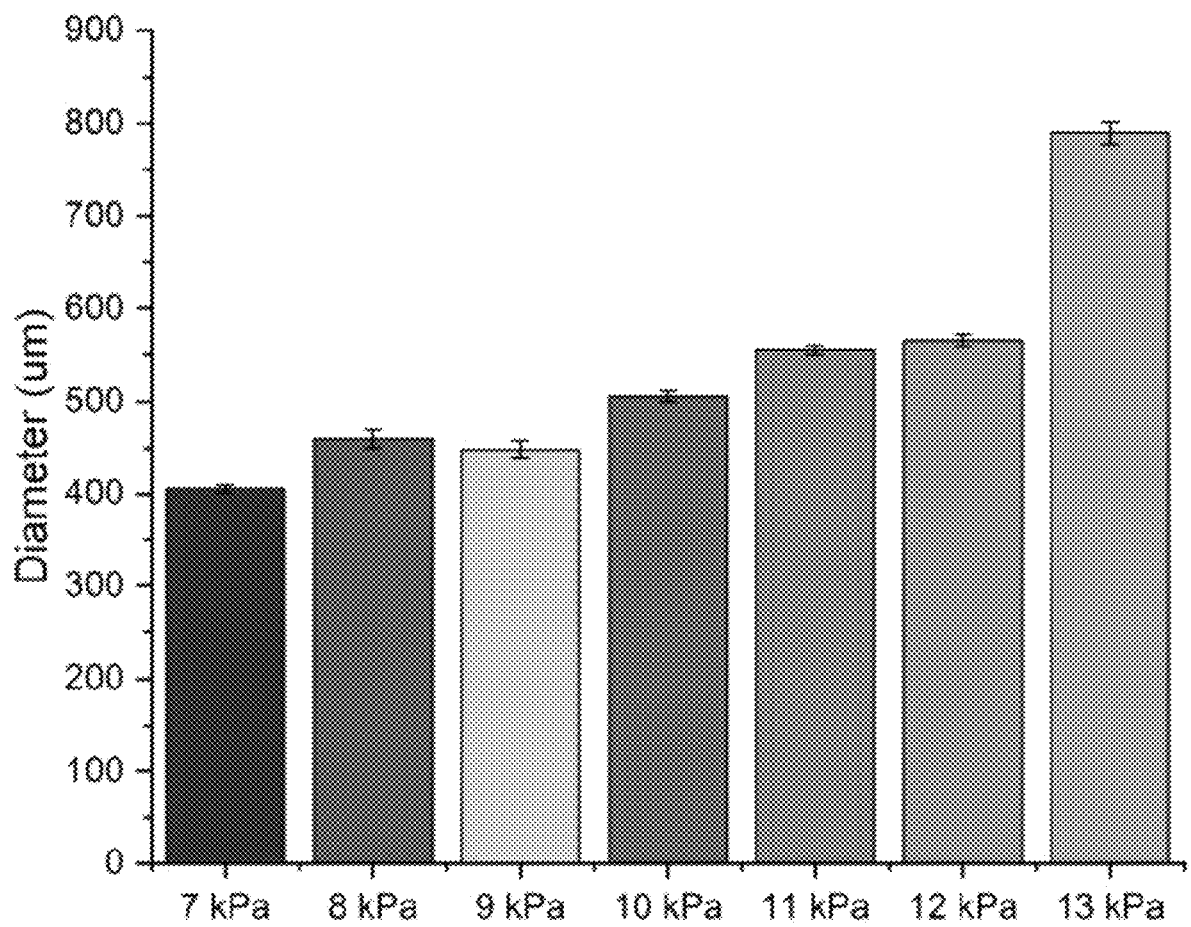
FIG. 26 depicts 3D printed collagen fiber diameter of various extrusion pressures from the Cellink BioX printer using a 27-gauge nozzle at 3 mm/s.

Using a 27-gauge conical bioprinting nozzle tip from Cellink, a profile of LC's print diameter was determined by holding the printing rate a 3 mm/s. The results are shown in FIG. 26. Noticeably, an increase in printed diameter was observed with increased extrusion pressure ranging from 7 kPa to 13 kPa. Printed diameters ranged from 400 µm to 802 µm. A significant increase in printed diameter was observed from 12 kPa to 13 kPa with demonstrated approximately 224 µm increase in diameter. Printing below 6 kPa was not possible due to the difficulty of extruding collagen under low pressures while printing above 13 kPa resulted in non-uniform collagen diameters.

Thermal Stability

Figure 27A:
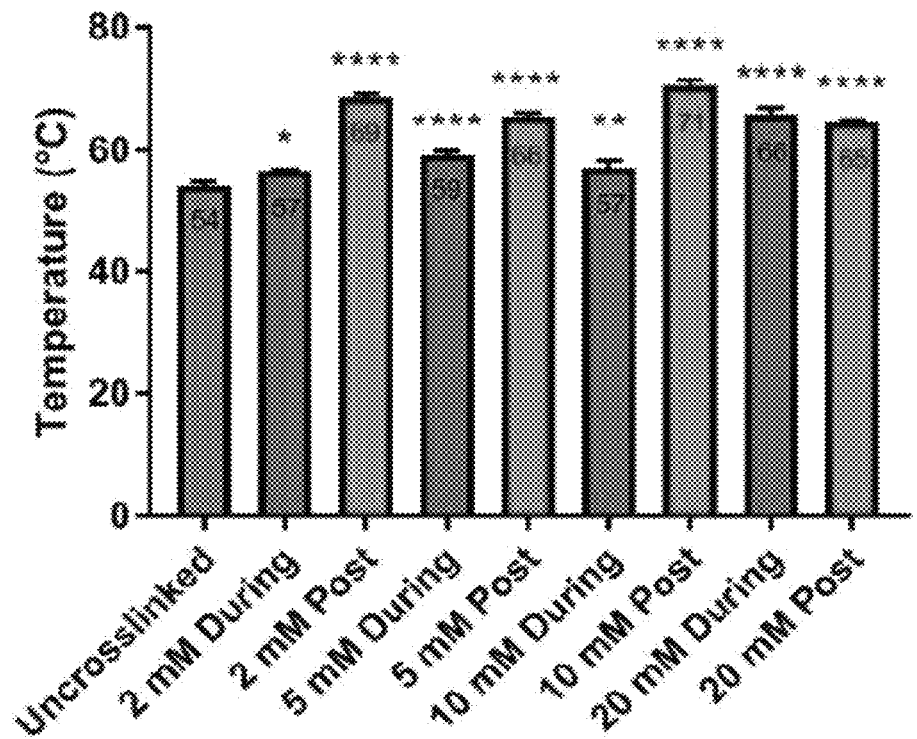
FIG. 27A depicts DSC denaturation results from crosslinking using EDC/NHS during printing or after printing.

Thermal stability of 3D printed scaffolds crosslinked with either EDC/NHS or genipin were analyzed using DSC analysis. In preliminary experiments with EDC/NHS crosslinking, two methods of crosslinking were tested. In one method, the samples were printed directly into the crosslinking solution. In the second method, the samples were printed into water, and stayed in water for 24 hours and then placed in the crosslinking solution. The denaturation results are shown in FIG. 27A. These results demonstrated that both methods increased the overall denaturation temperature relative to the uncrosslinked sample. Interestingly, the two crosslinking techniques demonstrated significantly different results. Crosslinking in 2 mM, 5 mM, and 10 mM, the samples that were printed in water first and then crosslinked had a much higher denaturation temperature compared to the samples that were printed directly into the crosslinking solution. Alternatively, the group that was printed directly into the 20 mM solution higher denaturation temperature in comparison to printing in water then crosslinking. Overall, the 10 mM EDC crosslinking group that was printed into water then crosslinked had the highest thermal stability at 71° C. The 2 mM EDC/NHS was used in future studies utilizing EDC/NHS crosslinking unless otherwise stated. The reasoning for using 2 mM EDC/NHS was to achieve structural stability of the collagen scaffold without the rigidity. If the scaffold is too stiff, then the collagen's ability to achieve enhanced cellularity might be reduced. The 2 mM solution provided an increase denaturation temperature which provided us a more thermally stable scaffold.

Figure 27B:
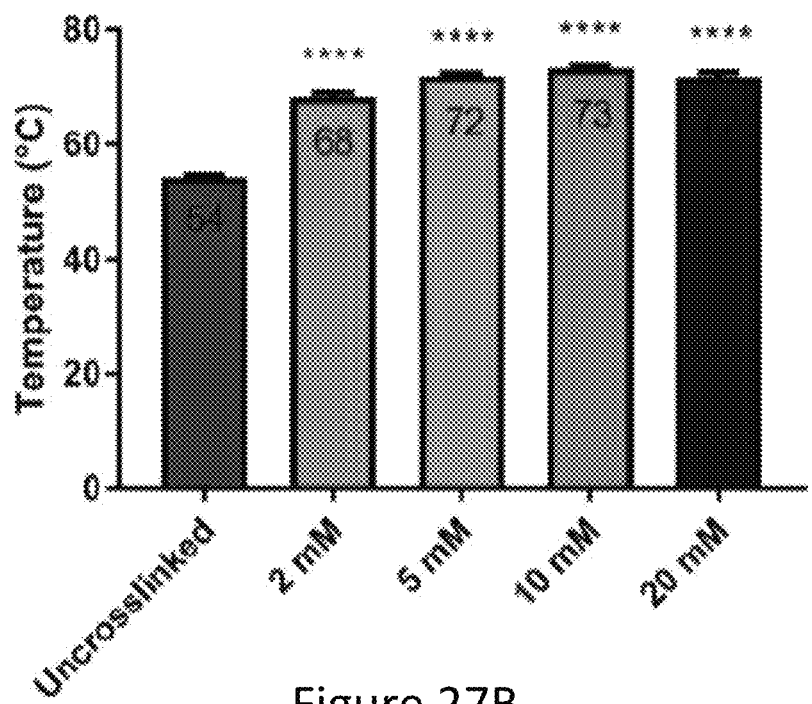
FIG. 27B depicts DSC denaturation results from crosslinking using genipin.
Figure 28A:
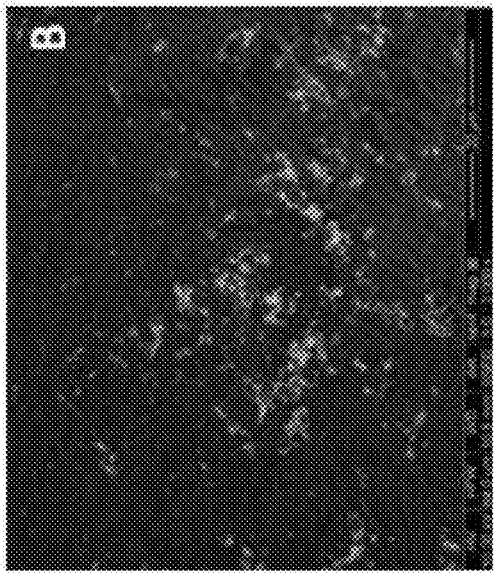
FIG. 28A is a SEM backscattered micrograph of EDC/NHS conjugated AuNPs on a 3D printed scaffold at 500× magnification.
Figure 28B:
FIG. 28B is a portion of the SEM backscattered micrograph of FIG. 28A of EDC/NHS conjugated AuNPs on a 3D printed scaffold at 2,000× magnification.
Figure 28C:
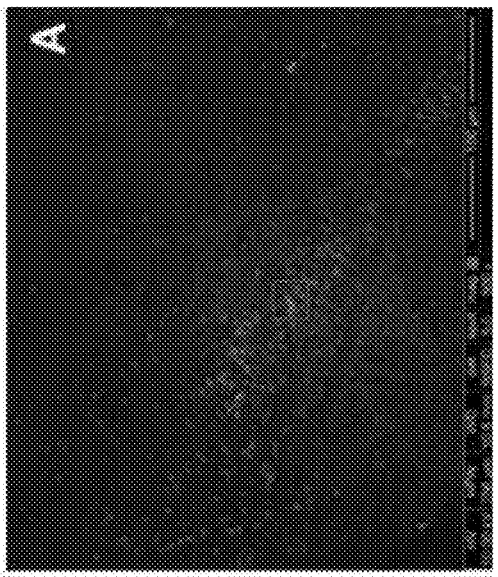
FIG. 28C is a portion of the SEM backscattered micrograph of EDC/NHS conjugated AuNPs on a 3D printed scaffold at 314× magnification.
Figure 28D:
FIG. 28D is a portion of the SEM backscattered micrograph of FIG. 28C of EDC/NHS conjugated AuNPs on a 3D printed scaffold at 5,000× magnification.
Figure 29A:
FIG. 29A is a secondary electron micrograph of genipin conjugated AuNPs (1× AuNP concentration) on a 3D printed scaffold.
Figure 29B:
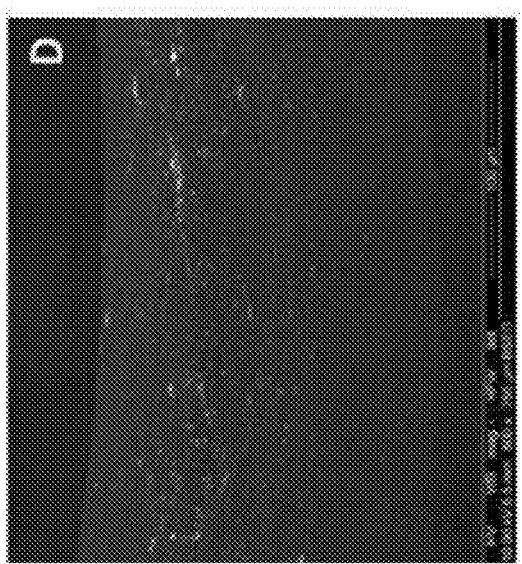
FIG. 29B is a backscattered electron micrograph of genipin conjugated AuNPs (1× AuNP concentration) on a 3D printed scaffold.
Figure 29C:
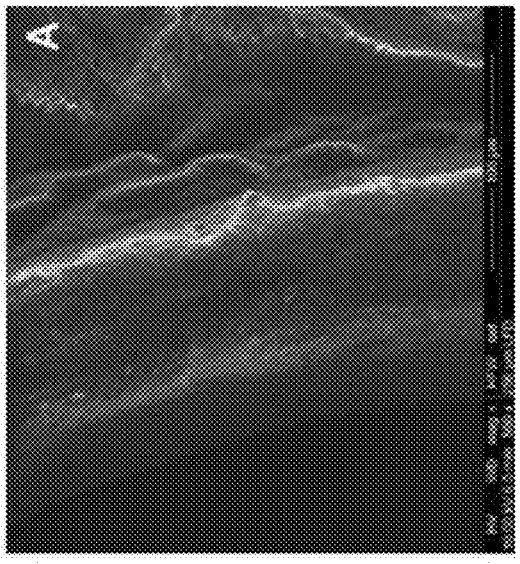
FIG. 29C is a secondary electron micrograph of genipin conjugated AuNPs (2× AuNP concentration) on a 3D printed scaffold.
Figure 29D:
FIG. 29D is a backscattered electron micrograph of genipin conjugated AuNPs (2× AuNP concentration) on a 3D printed scaffold.

Samples crosslinked with genipin were all printed into water and then placed in a genipin crosslinking solution. All samples crosslinked with genipin were significantly more stable than uncrosslinked samples as shown in FIG. 27B. An increase in denaturation temperature can be observed by increasing the genipin crosslinking solution from 2 mM to 10 mM. The increased denaturation temperature from 2 mM to 5 mM was the most significant with an overall decrease in denaturation temperature observed from 10 mM to 20 mM. With 2 mM genipin providing a significant increase in thermal stability and due to the cost of genipin, 2 mM genipin was used in all future studies unless otherwise stated.

SEM Analysis

Both EDC/NHS and genipin crosslinking was used to conjugate AuNPs to the 3D printed collagen scaffolds and were analyzed using SEM microscopy to validate the presence of AuNPs as shown in FIGS. 28A-28D and 29A-29D respectively. Both crosslinking techniques had AuNPs conjugated to the surface of the printed collagen fibers. Upon visual inspection, the samples conjugated with EDC/NHS appeared to have more clumped AuNPs on the surface of the scaffolds relative to the samples conjugated with genipin.

NAA Analysis

Figure 30A:
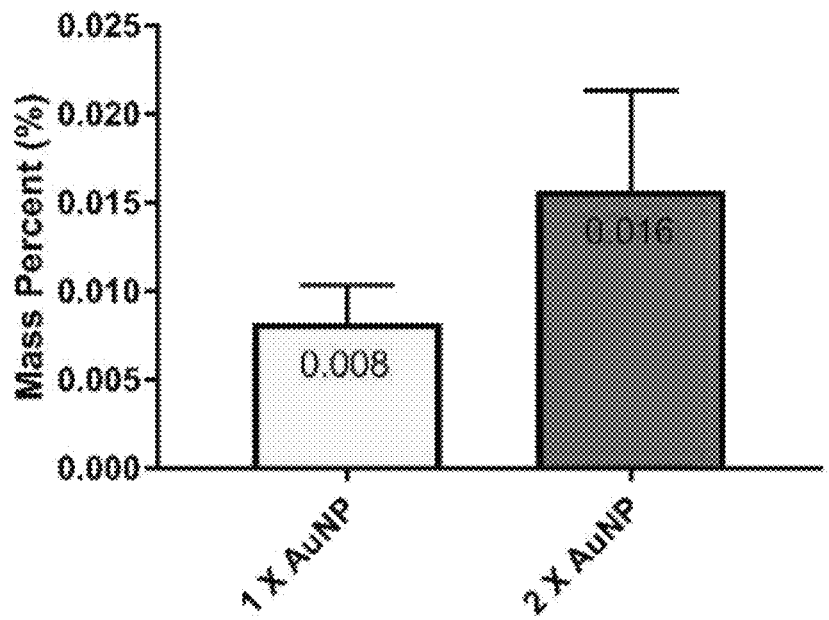
FIG. 30A depicts NAA results from crosslinking AuNPs to 3D printed scaffolds with EDC/NHS.
Figure 30B:
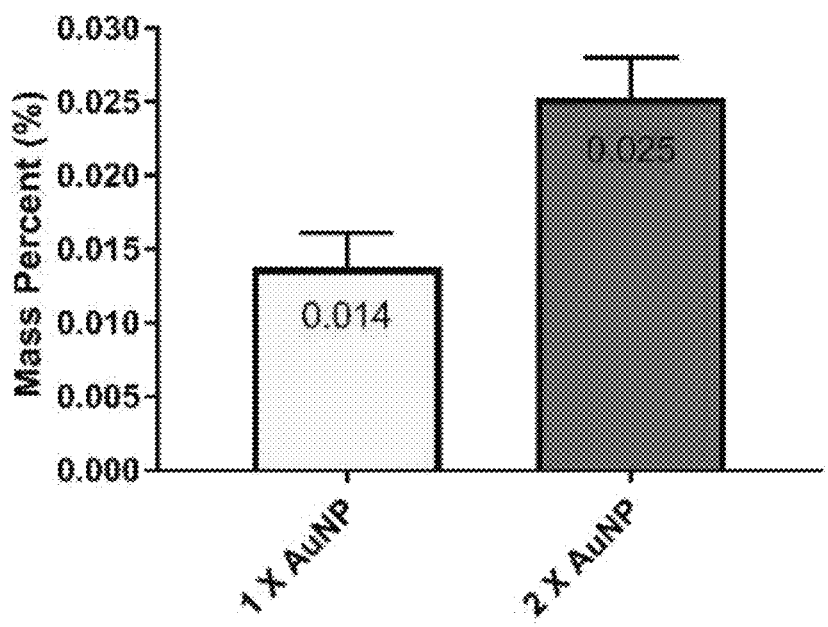
FIG. 30B depicts NAA results from crosslinking AuNPs to 3D printed scaffolds with genipin.

NAA analysis was used to provide a quantitative measurement of relative AuNPs conjugated to the 3D printed scaffolds. The results are shown in FIG. 30A-30B. 1× and 2× concentrations of AuNPs were conjugated with both EDC/NHS and genipin. On average genipin, in both cases of 1× and 2× AuNP concentrations, correlated to increased conjugation compared to EDC/NHS conjugation in terms of mass percent. Comparing the increase from 1× to 2× AuNP using EDC/NHS, this correlated to an approximately 100% increase in AuNP mass percentage shown in FIG. 20A. When examining the use of genipin comparing 1× and 2× AuNP mass percent, approximately a 78% increase in AuNP attachment was observed as shown in FIG. 30B.

3D Printing into a Cell Suspension

Figure 31A:
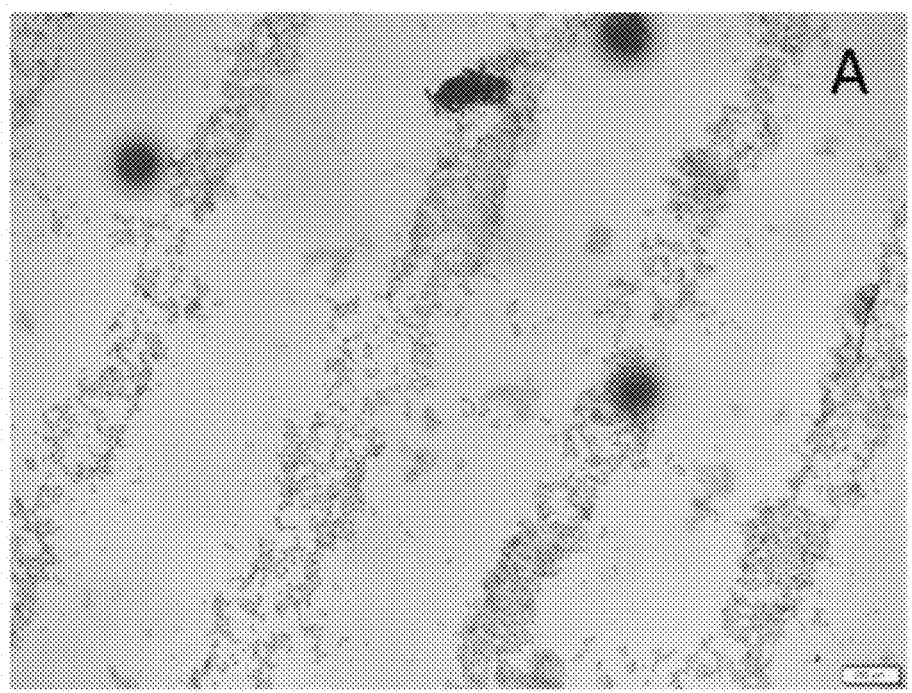
FIG. 31A is a 4× light microscopy image of cells on collagen fibrils immediately after printing collagen scaffold into L929 cell solution without washing.
Figure 31B:
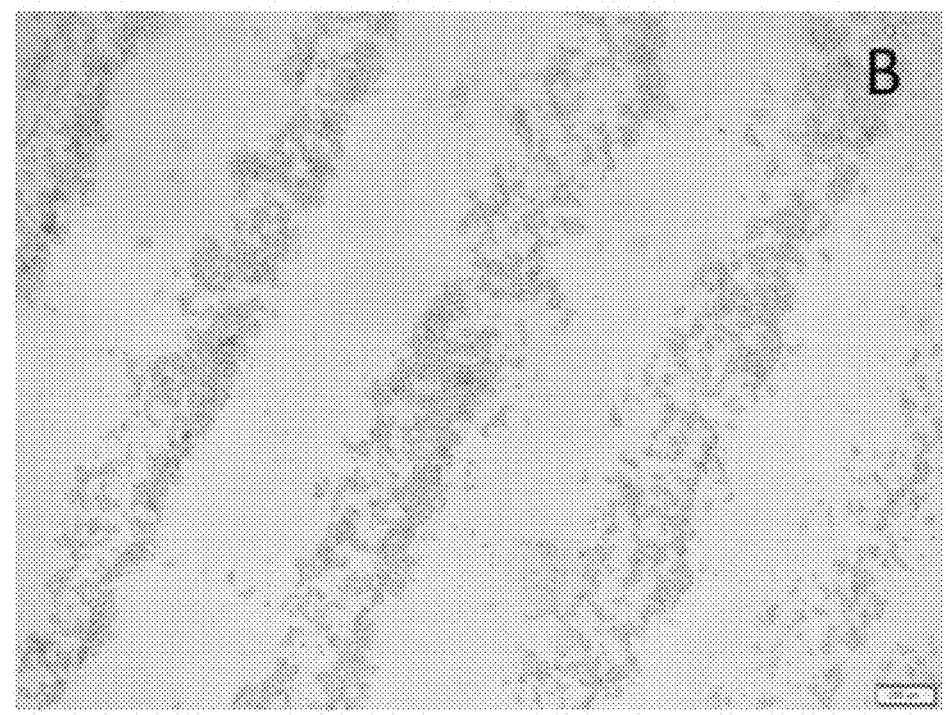
FIG. 31B is a 4× light microscopy image of cells on collagen fibrils immediately after printing collagen scaffold into L929 cell solution after 10 minutes of incubation and 5 washes.

Printing of a 3D collagen scaffold into an L929 fibroblast cell solution was investigated using light microscopy. FIG. 31A-31B provides images of a 3D printed scaffold printed into 4 ml of $4.0\times10^5$ cells/ml L929 fibroblast solution. The goal of this study was to determine if printing into a cell solution with a 10-minute incubation would provide enough time for the cells to adhere to the 3D scaffold. FIG. 31A is an image immediately after he printing of the scaffold. The outline of the collagen fibers can be observed due to the cells covering and adhering to the fibers. After a 10-minute incubation of the cells at 37° C., the 3D scaffold was washed 5 times using cell media and imaged again as shown in FIG. 31B. After washing the scaffold, a significant number of cells still remained on the 3D printed scaffold.

Cell Viability Analysis

Figure 32A:
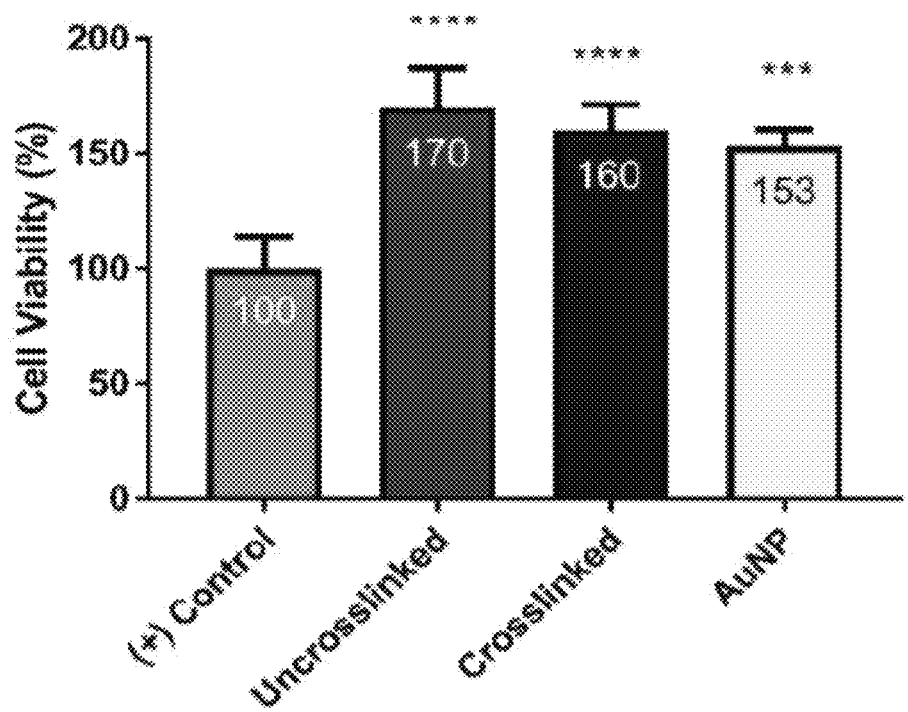
FIG. 32A depicts a WST1 cell viability analysis with L929 murine fibroblast cells after 3 days of culture with genipin crosslinker.
Figure 32B:
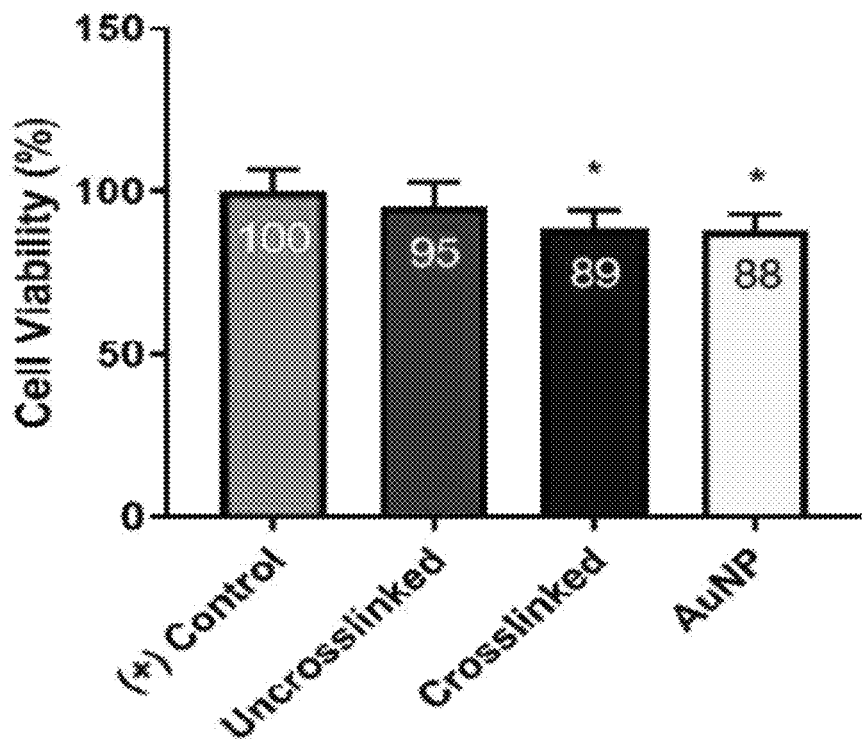
FIG. 32B depicts a WST1 cell viability analysis with L929 murine fibroblast cells after 3 days of culture with EDC/NHS crosslinker.
Figure 32C:
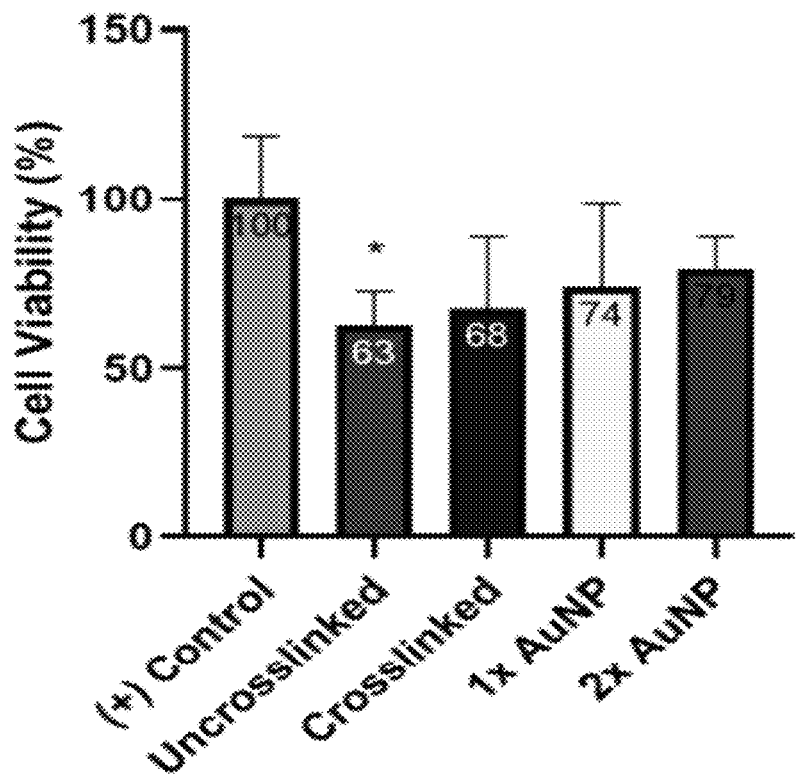
FIG. 32C depicts a WST1 cell viability analysis with L929 murine fibroblast cells after 7 days of culture with genipin crosslinker.

A 3 day cell viability analysis was conducted using both EDC/NHS and genipin crosslinkers with AuNPs. Results are shown in FIG. 32A-32C. Scaffolds crosslinked with genipin were studied in FIG. 32A. All groups with 3D printed collagen scaffolds had enhanced cellular viability compared to cells with no scaffold as shown in FIG. 32A. A reduction in viability can be observed with the genipin scaffolds and also the genipin scaffolds conjugated with AuNPs. Using EDC/NHS crosslinking, similar cellular viability can be observed between groups with 3D printed collagen scaffolds and cells with no scaffolds as shown in FIG. 32B. EDC/NHS crosslinking along with the addition of AuNPs decreased the cellular viability relative to cells with no scaffold.

A 7 day cell viability analysis was also conducted looking at the use of crosslinker genipin and 1× and 2× AuNP concentrations FIG. 32C. Cells with no scaffold had increased viability relative to cells with 3D printed collagen scaffolds. The addition of genipin to the scaffolds increased the viability relative to the uncrosslinked scaffolds. The conjugation of 1× and 2× AuNP further enhanced viability relative to genipin alone with 2× AuNP providing the highest overall viability relative to all groups with 3D printed scaffolds.

ROS Analysis

Figure 33:
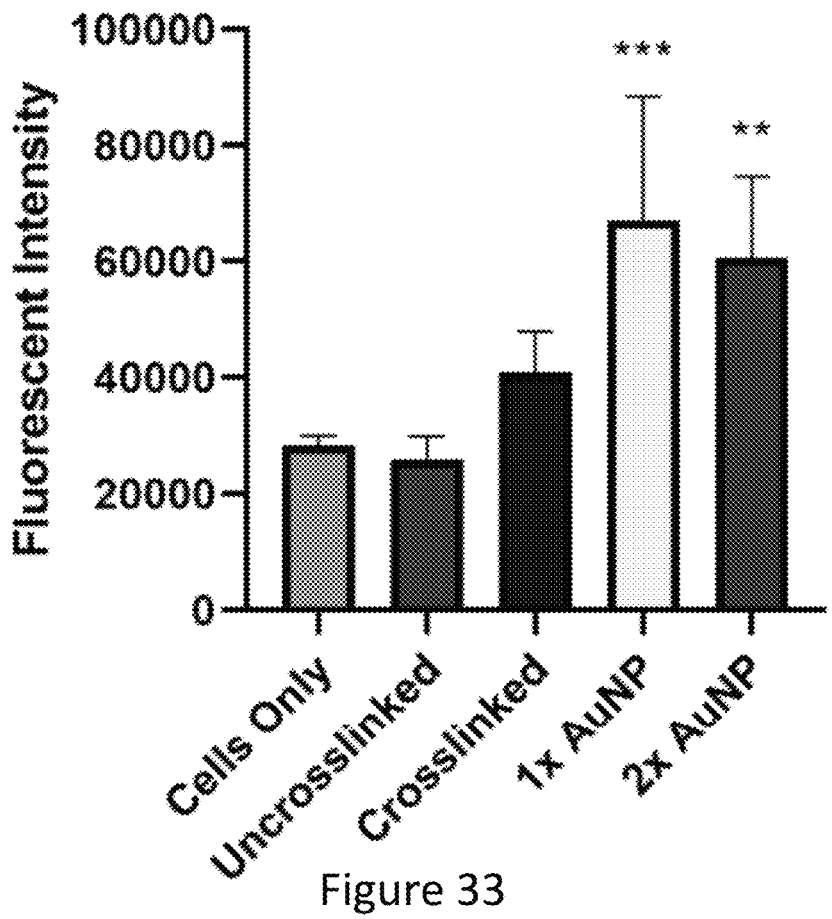
FIG. 33 depicts a 24-hour OxiSelect ROS assay quantifying produced intracellular ROS by L929 murine fibroblast cells.

An OxiSelect ROS assay was used to determine the ability of the 3D printed scaffolds to mitigate intracellular ROS production by the cells after the introduction of the 3D printed collagen scaffolds n FIG. 33. The uncrosslinked 3D printed scaffolds produced similar amounts of ROS relative to the cells with no scaffold added. Crosslinking with genipin and the addition of AuNPs appeared to increase ROS production with the addition of AuNP significantly increasing ROS production.

Printing in Agarose Solution

Figure 34:
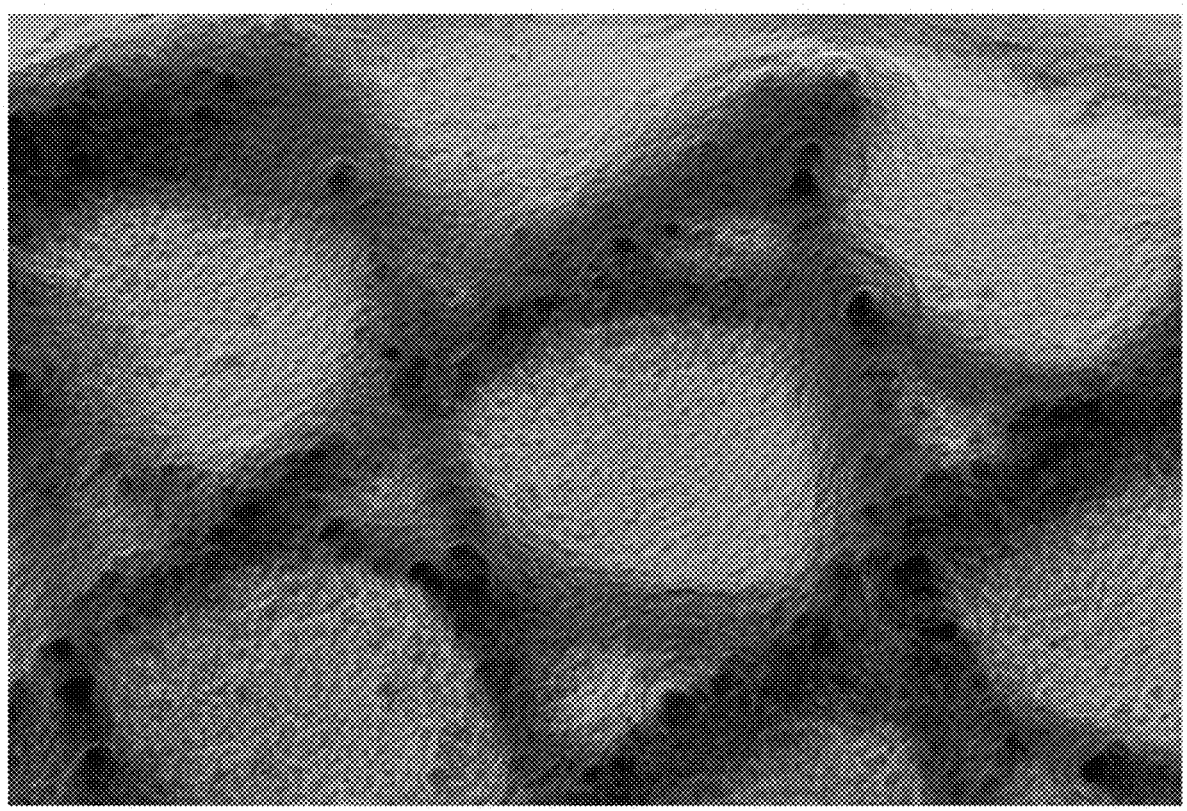
FIG. 34 is a 4× light microscopy image of a 3D printed collagen scaffold printed into agarose microparticle solution. The scaffold was washed prior to imaging. Some of the remnant agarose particles can be seen on the scaffold.

Printing into an agarose microparticle solution was attempted as shown earlier in FIG. 25B and cultured with cells. Printing into the agarose microparticle solution was advantageous due to the almost 100% reproducibility of each scaffold. However, problems arose when printing into the agarose microparticle solution when culturing cells on the 3D printed scaffolds. The first complication was washing the scaffolds after printing. The agarose needed to be removed from the scaffold post-printing. After washing, remnant agarose microparticles were apparent on the 3D printed scaffold as shown in FIG. 34. Secondly, cells seeded onto the scaffold did not appear to have much if any attachment on the scaffold, preferring the bottom of the well plate instead.

Stromal Cell Degradation of 3D Printed Scaffolds

Figure 35A:
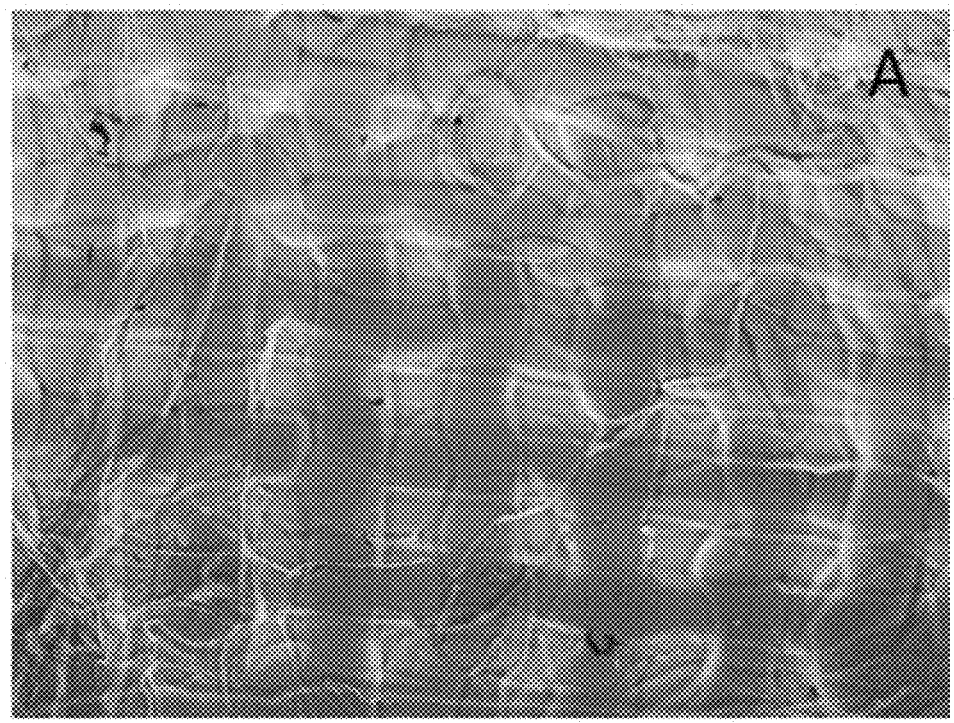
FIG. 35A is a 4× light microscopy image of 9-day cultured 3D printed collagen scaffolds with no crosslinker and with no cells.
Figure 35B:
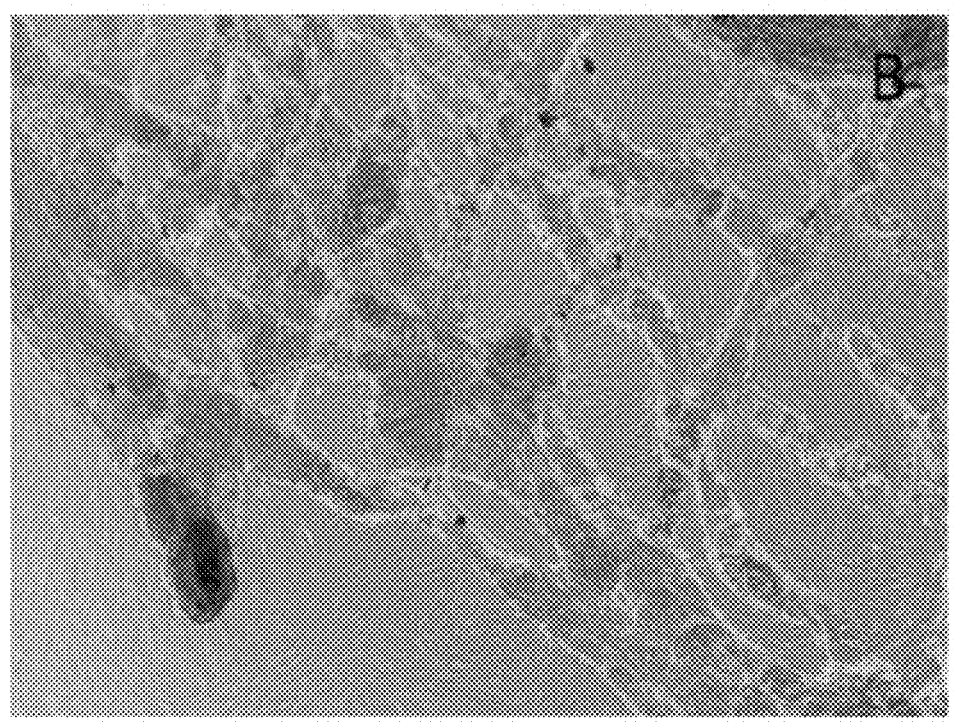
FIG. 35B is a 4× light microscopy image of 9-day cultured 3D printed collagen scaffolds with no crosslinker and with stromal cells.

Stromal cells were seeded onto a 10 mm×0.6 mm 3D printed collagen scaffold. FIG. 35A-35B provides images of the scaffold at 9 days of incubation without cells, FIG. 35A, and with the stromal cells, FIG. 35B. The cells appeared to significantly degrade the 3D printed scaffold at 9 days relative to the sample with no cells. The cells also began to seed along the bottom of the well plate.

Figure 36:
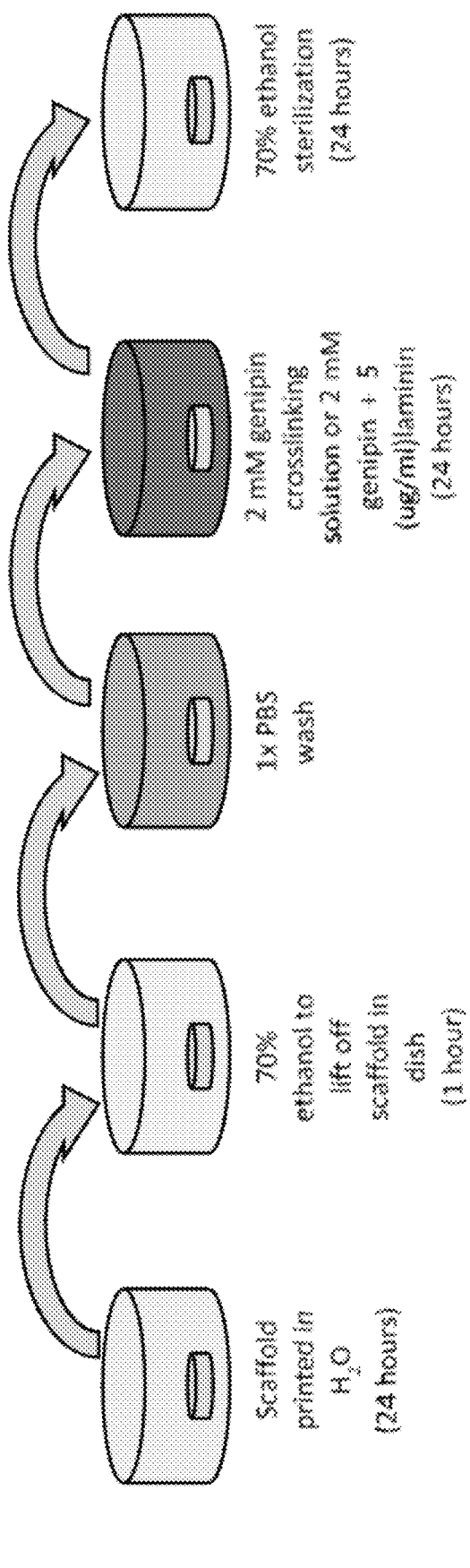
FIG. 36 depicts a diagram of how 3D printed collagen scaffolds were prepared for culture with stromal cells.
Figure 37:
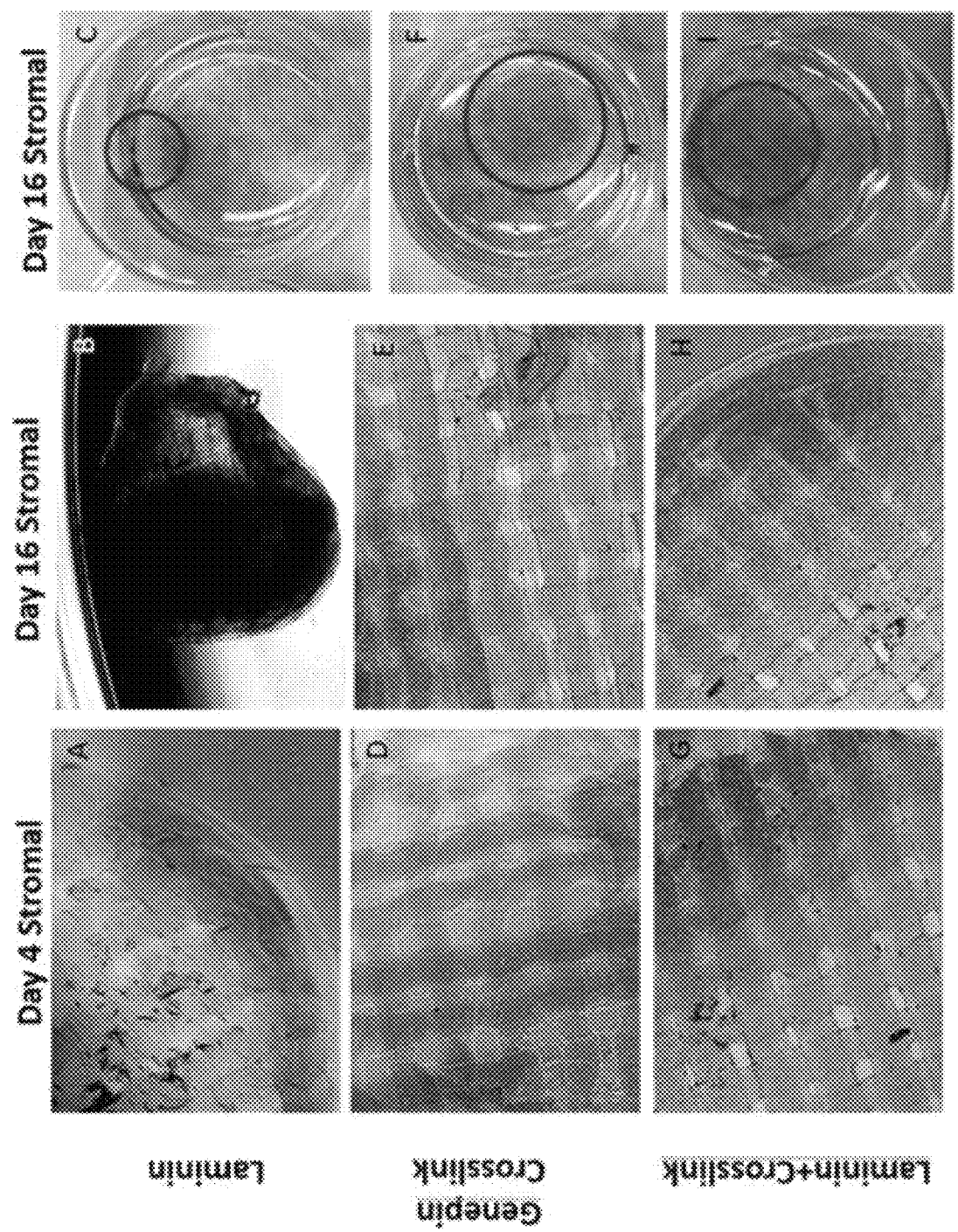
FIG. 37 depicts images of stromal cells seeded onto 3D printed collagen scaffolds supplemented with laminin (top row); genipin crosslinked (middle row); and genipin crosslinked and laminin (bottom row). Images in the left column are 4× light microscopy images at 4 days of incubation. Images in the center column are 4× light microscope images at 16 days of incubation. Images in the right column are photographs at 16 days of incubation.

This study was repeated with stromal cells. This time three separate groups were studied, genipin only, laminin only, and genipin+laminin (FIG. 37). Genipin was used to crosslink the collagen fibers to create a more stable structure as previously observed from the DSC results. Laminin, a basement membrane protein, was also added to the scaffolds in an attempt to improve cellular adherence to the 3D printed scaffolds. The third group is a genipin+laminin. FIG. 36 provides a flow chart on how these scaffolds were prepared for culture. The results of the scaffolds seeded with stromal cells can be observed in FIG. 37. Images were acquired at 4 days (FIG. 37, left column) and 16 days (FIG. 37, center and right columns) of culture. On day 4 of culture, the scaffold with only laminin began shrinking, and visually the pores of the scaffold were lost. Both samples crosslinked with genipin remained structurally sound and their shape was retained. Cells can be observed on the surface of both genipin crosslinked scaffolds at 4 days. At 16 days, the laminin only sample had completely lost its structural integrity and formed a globular shape. The two genipin crosslinked samples remained structurally intact at 16 days. Again, both genipin crosslinked samples retained a homogenous cellular network across their scaffolds. Photographs of the scaffolds at 16 days are shown in FIG. 37 (right column). The scaffold's porous network is still visible by the naked eye with samples crosslinked with genipin while the uncrosslinked, laminin sample demonstrated visible reduction in size and loss of integrity.

Discussion

In this example, the use of an LC solution is described that can be extruded from two different additive manufacturing 3D printers. The first printer being a custom-built printer utilizing CNC milling motors along with a mounted syringe pump to create a 3D structure and second, a commercial Cellink BioX bioprinter. Investigation of extrusion pressure was performed using the Cellink BioX bioprinter which provided a profile of extruded collagen fiber diameters.

Thermal stability analysis was also performed on various molar concentrations of the crosslinkers EDC/NHS and genipin. It was determined that printing the 3D scaffolds first in water and then crosslinking the scaffolds after printing created a more thermally stable structure. It is theorized that this two-step process created a more stable structure because the collagen fibrils are allowed to self-assemble naturally prior to chemical crosslinking. Printing directly into a crosslinking solution may cause immediate crosslinking of carboxyl to amino groups and thereby disrupting the natural fibrilization of the liquid collagen, leading to a less thermally stable structure. Genipin was also investigated as a potential crosslinker after printing the 3D scaffold. Genipin was able to create a more thermally stable scaffold relative to EDC/NHC crosslinking. However, both EDC/NHS and genipin crosslinkers created a scaffold that could survive thermal conditions in the body.

Both EDC/NHS and genipin were investigated as potential agents to crosslink AuNPs to the 3D scaffolds. AuNPs were able to be visualized on the surface of the 3D scaffolds through SEM analysis. The SEM micrographs provide evidence that EDC/NHS may have induced more clumping of the AuNPs on the surface of the 3D scaffold while the use of genipin provided evidence of more homogenous distribution of AuNPs over the 3D scaffold. NAA analysis was also then conducted to determine the mass percent of AuNPs on the 3D scaffolds. Doubling the amount of AuNPs during crosslinking correlated to an approximate doubling in AuNPs conjugated to the 3D scaffolds in both cases of using EDC/NHS and genipin. Further work could be conducted to determine an approximate limit of conjugation with each concentration of EDC/NHS and genipin. Other work with AuNPs has shown their potential as anti-inflammatory agents with a propensity toward cellular migration which are advantageous properties for potential in vivo scaffolds.

A 3-day WST-1 cell viability analysis was performed on the 3D printed collagen scaffolds that were crosslinked with EDC/NHS and genipin and conjugated with AuNPs. It was apparent that the cells were viable on the 3D printed scaffolds and there was a significant increase in cellularity at day 3 compared to the control. The genipin conjugated AuNP scaffolds demonstrated a reduction in the overall viability relative to the uncrosslinked scaffold but still demonstrated high cellularity. The EDC/NHS scaffolds demonstrated a slightly reduced cellular viability relative to cells with no scaffold. It was concluded that genipin demonstrated a more cell-friendly crosslinker, which is in agreement with published literature. Thus, for these experiments, genipin is favored over the use of EDC/NHS crosslinking.

A 7-day WST-1 cell viability analysis was also performed only using genipin to crosslink AuNPs to the 3D scaffolds. At this time point, the cells with no scaffold were the most metabolically active. Interestingly all samples crosslinked with genipin had an increased cellular viability relative to the uncrosslinked scaffold with 1× AuNP having the highest overall viability among groups with a scaffold. Comparing these results with the 3-day results, over a longer-term study the genipin-AuNP scaffolds were favorable.

Printing in an agarose microparticle solution has the advantage of achieving enhanced reproducibility and 3D scaffold resolution. The drawbacks incurred while printing the collagen solution into the agarose microparticles were remnant agarose left on the scaffolds after washing which resulted in poor cellular adherence. There have been previous published reports that demonstrated low attachment of cells to agarose. Washing of the 3D printed scaffolds needs to be further investigated in order to efficiently remove remnant agarose left on the surface of the 3D printed scaffolds. The use of printing in an agarose microparticle solution has many advantages especially in reproducibility which necessitates further investigation of washing.

The seeding of stromal cells onto a 3D printed scaffold could lay the groundwork for tissue engineering of various functional in vitro organs. Song et al. developed a method of uterine horn regeneration in a rat model utilizing a collagen scaffold seeded with stromal cells. Initial work was performed with stromal cells to determine if the 3D printed collagen scaffolds could remain structurally viable for long term use with stromal cells. Initially uncrosslinked 3D scaffolds were seeded with stromal cells and were observed after 9 days of incubation. At 9 days the stromal cells appeared to degrade the scaffold and appeared to prefer the bottom of the well plate. A revised scaffold was subsequently tested. The revised scaffold was crosslinked with genipin along with addition of laminin maintain the structural integrity and help adherence of the stromal cells on the scaffold. After 16 days, the samples crosslinked with genipin remained structurally viable and cells appeared to form a homogenous layer over the surface of the scaffold.

In conclusion, the ability to 3D print liquid collagen into structural tissue scaffolds was demonstrated. These scaffolds can be crosslinked and conjugated with AuNPs. The resulting scaffolds appear to be stable and have cellular viability leading to the possibility of developing a plethora of different tissue engineered structures.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

When introducing elements of the present invention or the embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

The invention claimed is:

1. A method to fabricate chemically uncrosslinked collagen microparticles, wherein the method comprises:
    a) combining an oil and either sorbitan monooleate or sorbitan monostearate and stirring to create a printing solution;
    b) adding a collagen bioink composition dropwise to the printing solution to create a combined solution, wherein the collagen bioink composition comprises collagen, a polar solvent, and a stabilizing divalent ion chelating agent, wherein the collagen bioink fibrilizes when introduced into the printing solution;
    c) stirring the combined solution;
    d) increasing the temperature of the combined solution to 37° C. while continuing stirring; and
    e) centrifuging the combined solution to collect the microparticles, wherein the combined solution is free of crosslinker or up to 0.05 mM of crosslinker is present.

2. A method to fabricate a chemically crosslinked collagen structure, wherein the method comprises the method of claim 1 and further comprises incubating the chemically uncrosslinked collagen microparticles or structure with a crosslinker and optionally an antibody, a peptide, an aptamer, a functionalized nanoparticle, or a combination thereof.

3. The method of claim 2, wherein the method comprises adding an antibody, a peptide, an aptamer, a functionalized nanoparticle, or a combination thereof to the incubation step.

4. The method of claim 1, wherein the oil is olive oil.

5. The method of claim 1, wherein the sorbitan monooleate concentration is from about 0.02 to about 0.35% by volume.

6. The method of claim 1, wherein the sorbitan monostearate concentration is from about 0.01 to about 2.50% by volume.

7. The method of claim 1, wherein step c) comprises stirring for 1 hour.

8. The method of claim 1, wherein step d) comprises stirring for up to 16 hours.

9. The method of claim 1, wherein the method further comprises washing the collected microparticles.

10. The method of claim 1, wherein the collected microparticles are uniform in size.

11. The method of claim 1, wherein the collected microparticles have a standard deviation in size of less than 15 μm.

12. The method of claim 1, wherein printing solution further comprises nanoparticles, an anti-inflammatory agent, or a combination thereof.

13. A method to fabricate a chemically crosslinked collagen structure, wherein the method comprises:
    a) combining an oil and either sorbitan monooleate or sorbitan monostearate and stirring to create a printing solution;
    b) adding a collagen bioink composition dropwise to the printing solution to create a combined solution, wherein the collagen bioink composition comprises collagen, a polar solvent, and a stabilizing divalent ion chelating agent, wherein the collagen bioink fibrilizes when introduced into the printing solution;
c) stirring the combined solution;
d) increasing the temperature of the combined solution to 37° C. while continuing stirring; and
e) centrifuging the combined solution to collect the microparticles, wherein the combined solution is substantially free of crosslinker;
and further comprising incubating the chemically uncrosslinked collagen microparticles with a crosslinker and a functionalized nanoparticle.

14. The method of claim 13, wherein the functionalized nanoparticle comprises gold, silver, silicon carbide, silicon, silica, or a combination thereof.

15. The method of claim 14, wherein the crosslinker is EDC/NHS (1-ethyl-3-(3-dimethylaminopropyl) carbodiimide/N-hydroxysuccinimide) or genipin.

16. The method of claim 13, wherein the functionalized nanoparticle comprises gold.

17. The method of claim 13, wherein the crosslinker has a concentration of from about 2 mM to about 10 mM.

* * * * *